US012583902B2

(12) United States Patent
Esteves et al.

(10) Patent No.: US 12,583,902 B2
(45) Date of Patent: Mar. 24, 2026

(54) DNA-BINDING DOMAIN TRANSACTIVATORS AND USES THEREOF

(71) Applicant: University of Massachusetts, Westborough, MA (US)

(72) Inventors: Miguel Sena Esteves, Worcester, MA (US); Scot A. Wolfe, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 1223 days.

(21) Appl. No.: 17/433,269

(22) PCT Filed: Feb. 24, 2020

(86) PCT No.: PCT/US2020/019546
§ 371 (c)(1),
(2) Date: Aug. 24, 2021

(87) PCT Pub. No.: WO2020/176426
PCT Pub. Date: Sep. 3, 2020

(65) Prior Publication Data
US 2022/0185862 A1 Jun. 16, 2022

Related U.S. Application Data

(60) Provisional application No. 62/810,005, filed on Feb. 25, 2019.

(51) Int. Cl.
| | |
|---|---|
| *C07K 14/705* | (2006.01) |
| *A61K 38/00* | (2006.01) |
| *C12N 9/22* | (2006.01) |
| *C12N 15/11* | (2006.01) |
| *C12N 15/86* | (2006.01) |

(52) U.S. Cl.
CPC .............. *C07K 14/705* (2013.01); *C12N 9/22* (2013.01); *C12N 15/11* (2013.01); *C12N 15/86* (2013.01); *A61K 38/00* (2013.01); *C07K 2319/71* (2013.01); *C07K 2319/80* (2013.01); *C07K 2319/81* (2013.01); *C12N 2310/20* (2017.05); *C12N 2750/14143* (2013.01)

(58) Field of Classification Search
CPC .............. C07K 14/705; C07K 2319/71; C07K 2319/80; C07K 2319/81; C12N 9/22; C12N 15/11; C12N 15/86; C12N 2310/20; C12N 2750/14143; C12N 15/63; C12N 15/113; A61K 38/00; A61K 48/00; A61P 25/08
See application file for complete search history.

(56) References Cited

U.S. PATENT DOCUMENTS

| | | | |
|---|---|---|---|
| 2003/0082561 A1 | 5/2003 | Sera | |
| 2005/0202498 A1 | 9/2005 | Kim et al. | |
| 2015/0064236 A1 * | 3/2015 | Bancel ................... | A61K 47/34 |
| | | | 435/69.6 |
| 2017/0204407 A1 * | 7/2017 | Gilbert ............... | C12N 15/1082 |
| 2018/0064827 A1 | 3/2018 | Conway et al. | |
| 2019/0024118 A1 | 1/2019 | Tagliatela et al. | |
| 2019/0024120 A1 | 1/2019 | Tagliatela et al. | |
| 2019/0127713 A1 | 5/2019 | Gersbach et al. | |
| 2019/0225955 A1 * | 7/2019 | Liu ......................... | A61P 35/00 |
| 2023/0279405 A1 | 9/2023 | Esteves et al. | |

FOREIGN PATENT DOCUMENTS

| | | | | |
|---|---|---|---|---|
| CA | 3042358 A1 | 5/2017 | | |
| CN | 1836048 A | 9/2006 | | |
| CN | 102939377 A | 2/2013 | | |
| CN | 109068620 A | 12/2018 | | |
| JP | 2018-513681 A | 5/2018 | | |
| JP | 2018088888 A | * | 6/2018 | |
| WO | WO-2002042459 A2 | * | 5/2002 | |
| WO | WO 2004/108883 A2 | 12/2004 | | |
| WO | WO 2007/061759 A1 | 5/2007 | | |
| WO | WO 2011/008260 A2 | 1/2011 | | |
| WO | WO 2016/161207 A1 | 10/2016 | | |
| WO | WO 2017/053729 A1 | 3/2017 | | |
| WO | WO 2017/053753 A1 | 3/2017 | | |
| WO | WO-2017180915 A2 | * | 10/2017 | ......... A61K 48/0058 |
| WO | WO 2018/049079 A1 | 3/2018 | | |
| WO | WO 2018/148256 A1 | 8/2018 | | |
| WO | WO 2018/187363 A1 | 10/2018 | | |
| WO | WO 2019/109051 A1 | 6/2019 | | |
| WO | WO 2019/199867 A1 | 10/2019 | | |
| WO | WO 2019/224864 A1 | 11/2019 | | |
| WO | WO 2020/097121 A1 | 5/2020 | | |

(Continued)

OTHER PUBLICATIONS

Partial European Search Report for Application No. 21847156.3, mailed Jul. 11, 2024.
Extended European Search Report for Application No. 21847156.3, mailed Oct. 2, 2024.
International Search Report and Written Opinion for Application No. PCT/US2021/042949, mailed Nov. 10, 2021.
International Preliminary Report on Patentability for Application No. PCT/US2021/042949, mailed Feb. 2, 2023.
Inglis et al., Transcriptomic and epigenomic dynamics associated with development of human iPSC-derived GABAergic interneurons. Hum Mol Genet. Aug. 29, 2020;29(15):2579-2595. doi: 10.1093/hmg/ddaa150.

(Continued)

*Primary Examiner* — Neil P Hammell
*Assistant Examiner* — Kyle T Rega
(74) *Attorney, Agent, or Firm* — Wolf, Greenfield & Sacks, P.C.

(57) ABSTRACT

In some aspects, the disclosure relates to recombinant adeno-associated viruses (rAAVs) comprising a nucleic acid encoding a fusion protein comprising a DNA-binding domain and a transcriptional regulator domain and methods of using the same. In some embodiments, expression of the fusion protein results in modified expression of a target gene in a cell.

15 Claims, 10 Drawing Sheets

Specification includes a Sequence Listing.

(56) References Cited

FOREIGN PATENT DOCUMENTS

| WO | WO 2020/176426 A1 | 9/2020 |
| WO | WO 2020/243651 A1 | 12/2020 |

OTHER PUBLICATIONS

Yu et al., Convergent Transcriptional Programs Regulate cAMP Levels in C. elegans GABAergic Motor Neurons. Dev Cell. Oct. 23, 2017;43(2):212-226.e7. doi: 10.1016/j.devcel.2017.09.013. Epub Oct. 12, 2017.

Extended European Search Report for Application No. 20762996.5, mailed Nov. 10, 2022.

Alwin et al., Custom Zinc-Finger Nucleases for Use in Human Cells. Mol Ther. Oct. 2005; 12(4):610-7. doi: 10.1016/j.ymthe.2005.06.094.

Bae et al., Human zinc fingers as building blocks in the construction of artificial transcription factors. Nat Biotechnol. Mar. 2003;21(3):275-80. doi: 10.1038/nbt796. Epub Feb. 18, 2003.

Gersbach et al., Synthetic Zinc Finger Proteins: The Advent of Targeted Gene Regulation and Genome Modification Technologies. Acc Chem Res. Aug. 19, 2014;47(8):2309-18. doi: 10.1021/ar500039w. Epub May 30, 2014.

EP 20762996.5, Nov. 10, 2022, Extended European Search Report.

International Search Report and Written Opinion for Application No. PCT/US2020/019546, mailed Jun. 11, 2020.

International Preliminary Report on Patentability for Application No. PCT/US2020/019546, mailed Sep. 2, 2021.

Bolukbasi et al., DNA-binding-domain fusions enhance the targeting range and precision of Cas9. Nat Methods. Dec. 2015;12(12):1150-6. doi: 10.1038/nmeth.3624. Epub Oct. 19, 2015.

Broekman et al., Adeno-associated virus vectors serotyped with AAV8 capsid are more efficient than AAV-1 or -2 serotypes for widespread gene delivery to the neonatal mouse brain. Neuroscience. 2006;138(2):501-10. doi: 10.1016/j.neuroscience.2005.11.057. Epub Jan. 18, 2006.

Chen et al., Tumor necrosis factor-a enhances voltage-gated Na? currents in primary culture of mouse cortical neurons. J Neuroinflammation. Jun. 26, 2015;12:126. doi: 10.1186/s12974-015-0349-x. 10 pages.

Gruntman et al., Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230. doi: 10.1089/hum.2017.037.

Han et al., Autistic-like behaviour in Sonla+/− mice and rescue by enhanced GABA-mediated neurotransmission. Nature. Sep. 20, 2012;489(7416):385-90. doi: 10.1038/nature11356. Epub Aug. 22, 2012.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Kalume et al., Reduced sodium current in Purkinje neurons from Nav1.1 mutant mice: implications for ataxia in severe myoclonic epilepsy in infancy. J Neurosci. Oct. 10, 2007;27(41):11065-74. doi: 10.1523/JNEUROSCI.2162-07.2007.

Kalume et al., Sudden unexpected death in a mouse model of Dravet syndrome. J Clin Invest. Apr. 2013;123(4):1798-808. doi: 10.1172/JCI66220. Epub Mar. 25, 2013.

Keeler et al., Cellular Analysis of Silencing the Huntington's Disease Gene Using AAV9 Mediated Delivery of Artificial Micro RNA into the Striatum of Q140/Q140 Mice. J Huntingtons Dis. Oct. 1, 2016;5(3):239-248. doi: 10.3233/JHD-160215.

Meng et al., Targeted gene inactivation in zebrafish using engineered zinc-finger nucleases. Nat Biotechnol. Jun. 2008;26(6):695-701. doi: 10.1038/nbt1398. Epub May 25, 2008.

Oakley et al., Temperature- and age-dependent seizures in a mouse model of severe myoclonic epilepsy in infancy. Proc Natl Acad Sci U S A. Mar. 10, 2009;106(10):3994-9. doi: 10.1073/pnas.0813330106. Epub Feb. 20, 2009.

Stoica et al., Adeno-associated virus-delivered artificial microRNA extends survival and delays paralysis in an amyotrophic lateral sclerosis mouse model. Ann Neurol. Apr. 2016;79(4):687-700. doi: 10.1002/ana.24618. Epub Mar. 11, 2016. Author Manuscript. 24 pages.

Sun et al., A deleterious Nav1.1 mutation selectively impairs telencephalic inhibitory neurons derived from Dravet Syndrome patients. Elife. Jul. 26, 2016;5:e13073. doi: 10.7554/eLife.13073.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Yu et al., Reduced sodium current in GABAergic interneurons in a mouse model of severe myoclonic epilepsy in infancy. Nat Neurosci. Sep. 2006;9(9):1142-9. doi: 10.1038/nn1754. Epub Aug. 20, 2006. Erratum in: Nat Neurosci. Jan. 2007;10(1):134.

Zhu et al., Using defined finger-finger interfaces as units of assembly for constructing zinc-finger nucleases. Nucleic Acids Res. Feb. 1, 2013;41(4):2455-65. doi: 10.1093/nar/gks1357. Epub Jan. 8, 2013.

Corton et al., Alterations in the GALA DNA-binding domain can affect transcriptional activation independent of DNA binding. J Biol Chem. May 29, 1998;273(22):13776-80. doi: 10.1074/jbc.273.22.13776.

Dahmann et al., Drosophilia: Methods and Protocols. Second Edition. 1993. Humana Press, eds. 361 pages. DOI 10.1007/978-1-4939-6371-3.

* cited by examiner

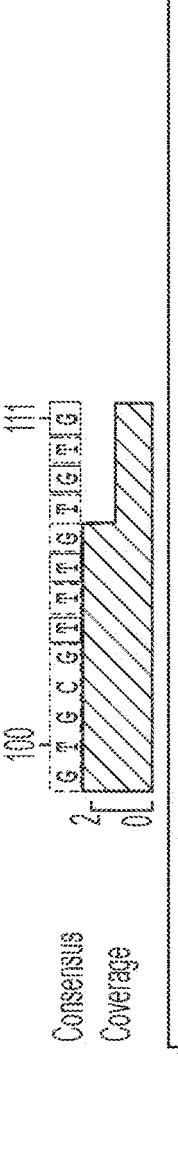
FIG. 1C

Reverse strand

Human  AATTTCCATGACTCTTTTTCCAAGGAATAACT-GGAATGAATAAACT------TAAAATCAAGATGAAACAATTAGATGGCTTACCTGATTAAAAGGAAAATTATCCATCTGCAGTGA
Mouse  TATTTCCGTGGGCTCTTCTCCCCAAGGATTACCCAAGGTAAGAATTCACCACCAAGAGAGATCACAATGAGATAATCAGATGGCTTACCTGATAAAAGGAAAATTATCCATCTGCAGTGA Human  GGAAACAGCCATCACCCAAGACGAGATGATAACAATGTGCCTTCAGTTGCAATTGTTCAGATTCCTTCTTCTGCAAAAGTGTCAAGTA-TTTACAGGGCTGCAGTCTCACTGGGGCAGAA
Mouse  GGAGCAACACATCTCCCAGCACCAGTC---------CGCACCCTTCCGTTGCAACGATTCAGATTCCTTCTTCTGCAAAAGTGCTTCACAAGGGCTGCAGCCTCATAGGGGCAGAA Human  CACCACAGACACCACAACACCACAACCAACGGCACACATTACACAACACCTCTGCCAGTATCCTCTCGGCTTCATCCTCCCTCACTCTATGGTACCTAAATACAAATCAGCAAATA
Mouse  CACCAC--GTACACAAACACACGCA------CACCACACACCACCAGAGACCCTCTGCCAGTATCCTCTCGGCTTCATCCTCCCTCACTCTATGGTACCTAAATACAAATCAGCAAATA Human  GCTTGTTTCAAAAAAAAA-------AAAAAAAAGTCAAGACCACCTTACATTACATCGGCCATCTAGTGGCTAAATATTAAACACTTTCTCACAATCCAGATTTATGATTTCTTCCTCAA
Mouse  GCTTGTTTTAAAAAAAAAAGAAAAAAAGAAAAACAAAAACCGGAGACAGAAAAAGCCGAGCACCACTAAGTTACACTGTAGTGCTACATCCTAATAGGTTCACAGCCTGGATTCTGTTCTTTCTCAA Human  CCTCTTTTCTCTCAGCCCTTTTCCTTTCTTCTCTGTAATCCCCAGTATTGCTTCTCC---TTGCTTCTCTTTCATTCCCTATTGTATAATAATATATGATCCAAGAGG
Mouse  CCGCTTCCTTTCGGTTCCTTTCCTTTCTTTTTCCTCTTTATTTTGGTTTTTATTACTTCCCATGTTATACTCCGC-CTAACACGGAACTATTGACTTAAAGATT Human  AAAAGGTTTCGAAAGTAATAATATAGCAATTTCAAGTAGTACTTGAAAAAACTTAGCCATTAATTTAGTTGAAACTGTTACTTTAATCCTAATATG
Mouse  AAAACAATCAGAACTCGGACACTGGACAGCCGGTGCTTTTAAGT------TAAAAAAAAAGTGCTAATTTGTTGTTGTAAATGTTACTTTATTTTCTCTATT Conserved region of interest for ZFP design in bold
*GAGTGAGCCGAGGATGAGCCGAGCCGAGAGGATGAGGAGAGATACTGCGAGAGGTC*

FIG. 2

FIG. 3 tttttttttttttttGAAACAAGCTATT

TGCTGATTTGTATTAGGTACCATAGAG·TGA·GGC·GAG·GAT·GAAGCCGAGAGAGGATACTGCAGAGGTCTTCTGGTGCAtgtgtgtatgtgtcgttgttgtgtg

FIG. 4A

| | | |
|---|---|---|
| F1 | GAA | QRGNLVR |
| F2 | GAT | LSFNLTR |
| F3 | GAG | RSDNLTR |
| F4 | GGC | DRSHLAR |
| F5 | TGA | QKAHLTA |
| F6 | GAG | RSDNLTR |

FQCRICMRNFS QRGNLVR HIRTHTGEKPI
FACDICGRKFA LSFNLTR HTKIHTGSQKPI
FQCRICMRNFS RSDNLTR HIRTHTGEKPI
FACDICGRKFA DRSHLAR HTKIHTGSQKPI
FQCRICMRNFS QKAHLTA HIRTHTGEKPI
FACDICGRKFA RSDNLTR HTKIHLRQKD

FIG. 4C

CGACCA

FIG. 4D tttttttttttttttCAAACAAGCTATT
TGCTGATTTGTATTAGCTACCATAGAGTGAGGC*GAG*GAT*GAA*GCC*GAGAGGATACTGCAGAGCTGTCGCTGCAtgtgtgt-atgtgtgcgtttgtgtg

FIG. 5A

F1  GAGa  RSSNLTR
F2  GCC   DKRTLTR (PMID 25593323)
F3  GAA   QRGNLVR
F4  GAT   LSFNLTR
F5  GAG   RSDNLTR
F6  GGC   DRSHLAR

FIG. 5B

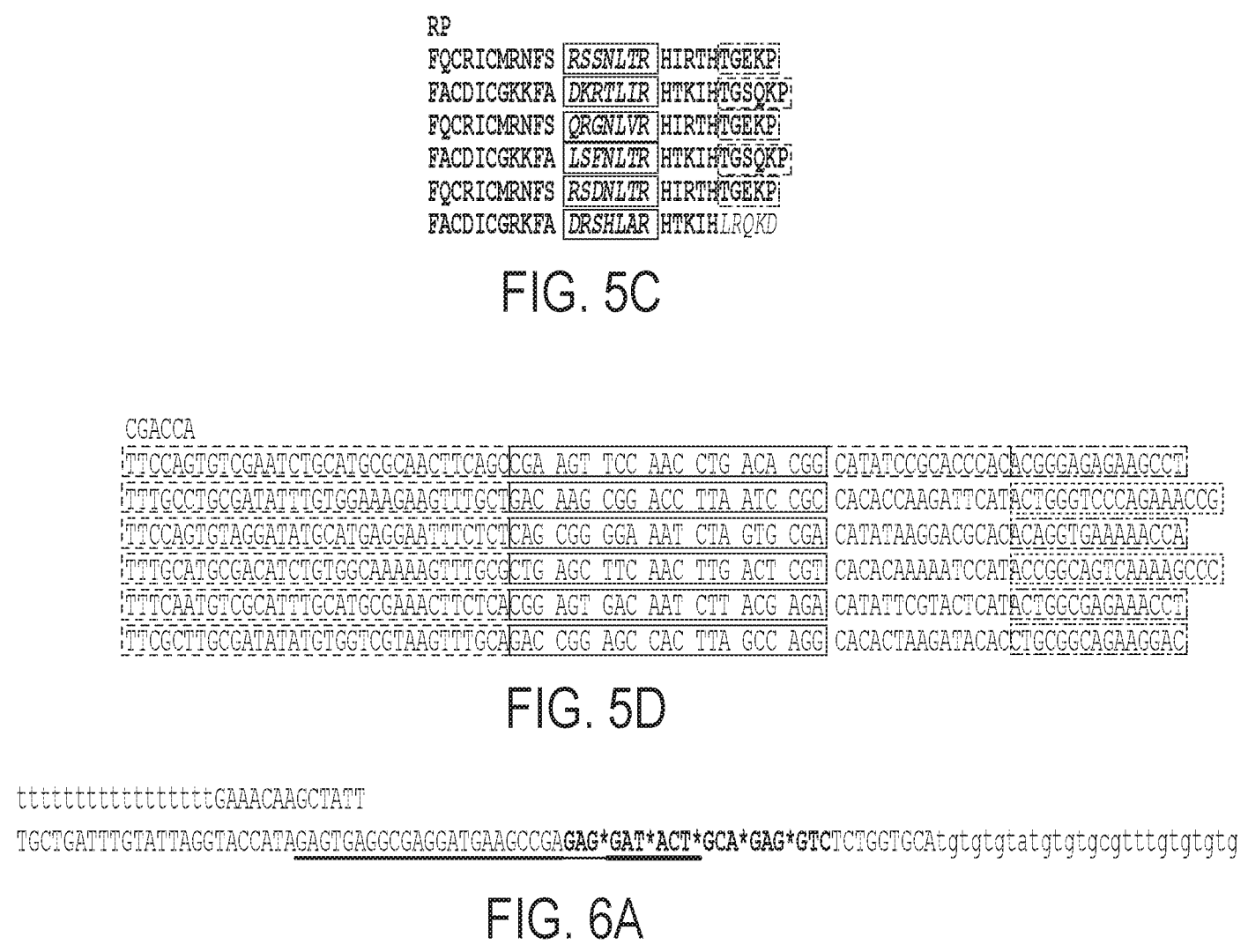

RP
FQCRICMRNFS | RSSNLIR | HIRTHTGEKP
FACDICGKKFA | DKRTLIR | HTKIHTGSQKP
FQCRICMRNFS | QRGNLVR | HIRTHTGEKP
FACDICGKKFA | LSPNLIR | HTKIHTGSQKP
FQCRICMRNFS | RSDNLIR | HIRTHTGEKP
FACDICGRKFA | DRSHLAR | HTKIHLRQKD

FIG. 5C

CGACCA
TTTCCAGTGTCGAATTGCCATGCGCAACTTCAGCCGA AGT TCC AAC CTG ACA CGG CATATCCGCACCACCCACGGGCGACGAGAAGCCT
TTTGCCTGCGATATTTGTGGAAAGAAGAGTTGCTTGAC AAG CGG ACC TTA ATC CGC CACACCAAGATTCATACTCGGTCCCAGAAACCG
TTTCCAGTGTCGAGGATATGCCATGCGCAACTTCTTCAG CGG GGA AAT CTA GTG CGA CATTATAAGGACGCACAGCTGAAAAACCA
TTTTGCATGCCACACTCTGCCAAAAGTTCGGCTG AGC TTC AAC TTG ACT CGT CACACAAAAATCCATACCCGCACGTCAAAAGCCC
TTTTCAATGTCGCATTTGCCATGCGCAACTTCTCAGG AGT GAC AAT CTT ACG AGA CATATTCGTACTCATACTGCCAGAAACCT
TTTGGCTTGCCAATATTGTGGTCGTAAGTTTGCAGAC CGG CAC TTA GCC AGG CACACTAAGATACACCTTGGCGAGAAGGAC

FIG. 5D ttttttttttttttttttGAAACAAGCTATT
TGCCTGATTTGTATTAGGTACCATAGAGAGTGAGGCGAGGATGAAGCCGAGAG*GAT*ACT*GCA*GAG*GTCTCTGGTGCAtgtgtgtatgtgtgcgtttgtgtg

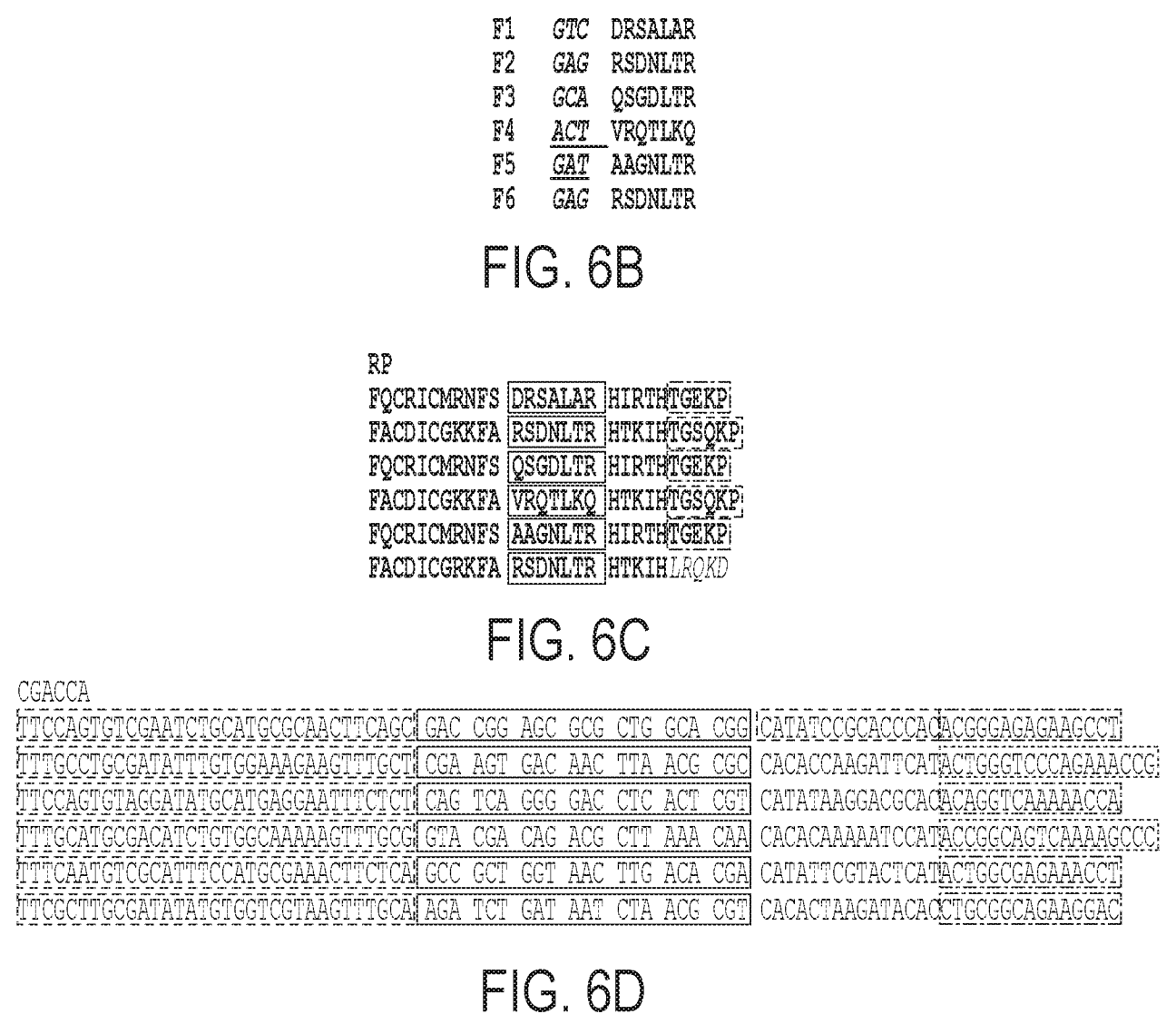

| F1 | GTC | DRSALAR |
|----|-----|---------|
| F2 | GAG | RSDNLTR |
| F3 | GCA | QSGDLTR |
| F4 | ACT | VRQTLKQ |
| F5 | GAT | AAGNLTR |
| F6 | GAG | RSDNLTR |

| FQCRICMRNFS | DRSALAR | HIRTHTGEKP |
| FACDICGKKFA | RSDNLTR | HTKIHTGSQKP |
| FQCRICMRNFS | QSGDLTR | HIRTHTGEKP |
| FACDICGKKFA | VRQTLKQ | HTKIHTGSQKP |
| FQCRICMRNFS | AAGNLTR | HIRTHTGEKP |
| FACDICGRKFA | RSDNLTR | HTKIHLRQKD |

FIG. 6D

SEQUENCE LISTING

<160> NUMBER OF SEQ ID NOS: 121

<210> SEQ ID NO 1
<211> LENGTH: 672
<212> TYPE: DNA
<213> ORGANISM: Homo sapiens

<400> SEQUENCE: 1

```
aatttccatg gactcttttt ccaaaggaat aactggaatg aataaactta aaatcaagat      60
gaaacaatta gatggcttac ctgattaaaa ggaaaattat ccatctgcag tgaggaacag     120
catcacccaa agacgagatg ataacaatgt gccttcagtt gcaattgttc agttccttct     180
tgcaaaaggt gtcaaagtat ttacaagggc tgcagtctca ctggggcaga acacacagac     240
acacaaacac acacaaacgc acacatacac acatgcacca gagacctctg cagtatcctc     300
tcggcttcat cctcgcctca ctctatggta cctaatacaa atcagcaaat agcttgtttc     360
aaaaaaaaaa aaaagtcaag acagcacctt acattacatc gccatctagt ggctaaatat     420
taaacacttt ctcacaatcc agattgatga tttcttcctc aacctctttt ctctcagctt     480
ttttcctttc ttctctgtaa tctcccagta ttgcttctcc ttgcttctct ttcattccct     540
attgctatat aatatcatga acctaatgac tcaaagagga aaaggtttga aagtaaatat     600
agctattttc aagtagtact tgaaaaactt agcattattt tagtttgaaa ctgttacttt     660
```

-continued

```
attcctaata tg                                                    672

<210> SEQ ID NO 2
<211> LENGTH: 669
<212> TYPE: DNA
<213> ORGANISM: Mus musculus

<400> SEQUENCE: 2
tatttccgtg ggctcttctc cccaaggatt taccaggtaa gaattcacca ccaaagaaga    60
tcacaatgag ataatcagat ggcttacctg ataaaaagga aaattatcca tctgcagtca   120
ggagcaacat ctccccacga cgagtccgca ccttccgttg caacgattca gattccttct   180
tgcaaaaggt gaccaagtgc ttcacaaggg ctgcagcctc ataggggaga acacacgtac   240
acaaacacac gcacacacac acacacatgc accagagacc tctgcagtat cctctggctt   300
catcctcgcc tcactctatg gtacctaata caaatcagca aatagcttgt tttaaaaaaa   360
agaaagaaaa aaagcggaga cagcacctaa cgttacagtg ccatctagtg gctacatcgt   420
aaataggttc tcacagcctg gatttctgtg ttctttctca accgcttcct tctggttcct   480
ttttcttttt tcctctttat tttggtttta ttacttcctc agatgccttt ttttcattcc   540
cctttgctct gcctacatgg aactattgac ttaaagatta aaacaatcag aactggagag   600
cgttgctttt aagttaaaaa aaaaaaggtt gctaattttg tttgtaaatg ttactttatt   660
ttctctatt                                                          669

<210> SEQ ID NO 3
<211> LENGTH: 130
<212> TYPE: DNA
<213> ORGANISM: Artificial Sequence
<220> FEATURE:
<223> OTHER INFORMATION: Synthetic

<400> SEQUENCE: 3
tttttttttt tttttttgaa acaagctatt tgctgatttg tattaggtac catagagtga    60
ggcgaggatg aagccgagag gatactgcag aggtctctgg tgcatgtgtg tatgtgtgcg   120
tttgtgtgtg                                                         130

<210> SEQ ID NO 4
<211> LENGTH: 41
<212> TYPE: DNA
<213> ORGANISM: Artificial Sequence
<220> FEATURE:
<223> OTHER INFORMATION: Synthetic

<400> SEQUENCE: 4
gagtgaggcg aggatgaagc cgagaggata ctgcagaggt c                       41

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
gagtgaggcg aggatgaa                                                 18

<210> SEQ ID NO 6
<211> LENGTH: 18
<212> TYPE: DNA
<213> ORGANISM: Artificial Sequence
```

-continued

```
<220> FEATURE:
<223> OTHER INFORMATION: Synthetic

<400> SEQUENCE: 6
ggcgaggatg aagccgag                                                    18

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
gaggatactg cagaggtc                                                    18

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Glu Gly Glu Asp Glu
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Gly Glu Asp Glu Ala Glu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Glu Asp Thr Ala Glu Val
1               5

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagcggggaa acctggtgag g                                                21

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
```

```
ctgagcttca atctaaccag a                                    21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
cggagtgaca acttaacgcg g                                    21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
gaccggtctc accttgcccg a                                    21

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
cagaaggccc atttgactgc c                                    21

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
cggtcggaca acctcacacg c                                    21

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Gln Arg Gly Asn Leu Val Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Leu Ser Phe Asn Leu Thr Arg
1               5

<210> SEQ ID NO 19
```

-continued

```
<211> LENGTH: 7
<212> TYPE: PRT
<213> ORGANISM: Artificial Sequence
<220> FEATURE:
<223> OTHER INFORMATION: Synthetic

<400> SEQUENCE: 19

Arg Ser Asp Asn Leu Thr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Asp Arg Ser His Leu Ala Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic

<400> SEQUENCE: 21

Gln Lys Ala His Leu Thr Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

Arg Ser Asp Asn Leu Thr Arg
1               5

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
cgaagttcca acctgacacg g                                                    21

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gacaagcgga ccttaatccg c                                                    21

<210> SEQ ID NO 25
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 25
cagcggggaa atctagtgcg a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
ctgagcttca acttgactcg t                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
cggagtgaca atcttacgag a                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
gaccggagcc acttagccag g                                              21

<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

Arg Ser Ser Asn Leu Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Asp Lys Arg Thr Leu Ile Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic

<400> SEQUENCE: 31
```

```
Gln Arg Gly Asn Leu Val Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Leu Ser Phe Asn Leu Thr Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Arg Ser Asp Asn Leu Thr Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Asp Arg Ser His Leu Ala Arg
1               5

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
gaccggagcg cgctggcacg g                                        21

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
cgaagtgaca acttaacgcg c                                        21

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
cagtcagggg acctcactcg t                                        21
```

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
gtacgacaga cgcttaaaca a                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
gccgctggta acttgacacg a                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
agatctgata atctaacgcg t                                              21

<210> SEQ ID NO 41
<211> LENGTH: 7
<212> TYPE: PRT
<213> ORGANISM: Artificial Sequence
<220> FEATURE:
<223> OTHER INFORMATION: Synthetic

<400> SEQUENCE: 41

Asp Arg Ser Ala Leu Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic

<400> SEQUENCE: 42

Arg Ser Asp Asn Leu Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Gln Ser Gly Asp Leu Thr Arg
1               5

<210> SEQ ID NO 44
<211> LENGTH: 7
<212> TYPE: PRT
<213> ORGANISM: Artificial Sequence

```
<220> FEATURE:
<223> OTHER INFORMATION: Synthetic

<400> SEQUENCE: 44

Val Arg Gln Thr Leu Lys Gln
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic

<400> SEQUENCE: 45

Ala Ala Gly Asn Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Arg Ser Asp Asn Leu Thr Arg
1               5

<210> SEQ ID NO 47
<211> LENGTH: 1569
<212> TYPE: DNA
<213> ORGANISM: Artificial Sequence
<220> FEATURE:
<223> OTHER INFORMATION: Synthetic

<400> SEQUENCE: 47
gaggccagcg gttccggacg ggctgacgca ttggacgatt ttgatctgga tatgctggga        60
agtgacgccc tcgatgattt tgaccttgac atgcttggtt cggatgccct tgatgacttt       120
gacctcgaca tgctcggcag tgacgccctt gatgatttcg acctggacat gctgattaac       180
tctagaagtt ccggatctag ccagtacctg cccgacaccg acgaccggca ccggatcgag       240
gaaaagcgga agcggaccta cgagacattc aagagcatca tgaagaagtc ccccttcagc       300
ggccccaccg accctagacc tccacctaga agaatcgccg tgcccagcag atccagcgcc       360
agcgtgccaa aacctgcccc ccagccttac ccccttcacca gcagcctgag caccatcaac       420
tacgacgagt tccctaccat ggtgttcccc agcggccaga tctctcaggc ctctgctctg       480
gctccagccc ctcctcaggt gctgcctcag gctcctgctc ctgcaccagc tccagccatg       540
gtgtctgcac tggctcaggc accagcaccc gtgcctgtgc tggctcctgg acctccacag       600
gctgtggctc caccagcccc taaacctaca caggccggcg agggcacact gtctgaagct       660
ctgctgcagc tgcagttcga cgacgaggat ctgggagccc tgctgggaaa cagcaccgat       720
cctgccgtgt tcaccgacct ggccagcgtg gacaacagcg agttccagca gctgctgaac       780
cagggcatcc ctgtggcccc tcacaccacc gagcccatgc tgatggaata ccccgaggcc       840
atcacccggc tcgtgacagg cgctcagagg cctcctgatc cagctcctgc ccctctggga       900
gcaccaggcc tgcctaatgg actgctgtct ggcgacgagg acttcagctc tatcgccgat       960
atggatttct cagccttgct gggctctggc agcggcagcc gggattccag ggaagggatg      1020
tttttgccga agcctgaggc cggctccgct attagtgacg tgtttgaggg ccgcgaggtg      1080
```

-continued

```
tgccagccaa aacgaatccg gccatttcat cctccaggaa gtccatgggc caaccgccca      1140
ctccccgcca gcctcgcacc aacaccaacc ggtccagtac atgagccagt cgggtcactg      1200
accccggcac cagtccctca gccactggat ccagcgcccg cagtgactcc cgaggccagt      1260
cacctgttgg aggatcccga tgaagagacg agccaggctg tcaaagccct tcgggagatg      1320
gccgatactg tgattcccca gaaggaagag gctgcaatct gtggccaaat ggacctttcc      1380
catccgcccc caaggggcca tctggatgag ctgacaacca cacttgagtc catgaccgag      1440
gatctgaacc tggactcacc cctgaccccg gaattgaacg agattctgga taccttcctg      1500
aacgacgagt gcctcttgca tgccatgcat atcagcacag gactgtccat cttcgacaca      1560
tctctgttt                                                              1569
```

```
<210> SEQ ID NO 48
<211> LENGTH: 523
<212> TYPE: PRT
<213> ORGANISM: Artificial Sequence
<220> FEATURE:
<223> OTHER INFORMATION: Synthetic

<400> SEQUENCE: 48

Glu Ala Ser Gly Ser Gly Arg Ala Asp Ala Leu Asp Asp Phe Asp Leu
1               5                   10                  15

Asp Met Leu Gly Ser Asp Ala Leu Asp Asp Phe Asp Leu Asp Met Leu
            20                  25                  30

Gly Ser Asp Ala Leu Asp Asp Phe Asp Leu Asp Met Leu Gly Ser Asp
        35                  40                  45

Ala Leu Asp Asp Phe Asp Leu Asp Met Leu Ile Asn Ser Arg Ser Ser
    50                  55                  60

Gly Ser Ser Gln Tyr Leu Pro Asp Thr Asp Asp Arg His Arg Ile Glu
65                  70                  75                  80

Glu Lys Arg Lys Arg Thr Tyr Glu Thr Phe Lys Ser Ile Met Lys Lys
                85                  90                  95

Ser Pro Phe Ser Gly Pro Thr Asp Pro Arg Pro Pro Arg Arg Ile
            100                 105                 110

Ala Val Pro Ser Arg Ser Ser Ala Ser Val Pro Lys Pro Ala Pro Gln
        115                 120                 125

Pro Tyr Pro Phe Thr Ser Ser Leu Ser Thr Ile Asn Tyr Asp Glu Phe
        130                 135                 140

Pro Thr Met Val Phe Pro Ser Gly Gln Ile Ser Gln Ala Ser Ala Leu
145                 150                 155                 160

Ala Pro Ala Pro Pro Gln Val Leu Pro Gln Ala Pro Ala Pro Ala Pro
                165                 170                 175

Ala Pro Ala Met Val Ser Ala Leu Ala Gln Ala Pro Ala Pro Val Pro
                180                 185                 190

Val Leu Ala Pro Gly Pro Pro Gln Ala Val Ala Pro Ala Pro Lys
                195                 200                 205

Pro Thr Gln Ala Gly Glu Gly Thr Leu Ser Glu Ala Leu Leu Gln Leu
        210                 215                 220

Gln Phe Asp Asp Glu Asp Leu Gly Ala Leu Leu Gly Asn Ser Thr Asp
225                 230                 235                 240

Pro Ala Val Phe Thr Asp Leu Ala Ser Val Asp Asn Ser Glu Phe Gln
                245                 250                 255

Gln Leu Leu Asn Gln Gly Ile Pro Val Ala Pro His Thr Thr Glu Pro
                260                 265                 270
```

-continued

```
Met Leu Met Glu Tyr Pro Glu Ala Ile Thr Arg Leu Val Thr Gly Ala
        275                 280                 285

Gln Arg Pro Pro Asp Pro Ala Pro Ala Pro Leu Gly Ala Pro Gly Leu
        290                 295                 300

Pro Asn Gly Leu Leu Ser Gly Asp Glu Asp Phe Ser Ser Ile Ala Asp
305                 310                 315                 320

Met Asp Phe Ser Ala Leu Leu Gly Ser Gly Ser Gly Ser Arg Asp Ser
                325                 330                 335

Arg Glu Gly Met Phe Leu Pro Lys Pro Glu Ala Gly Ser Ala Ile Ser
                340                 345                 350

Asp Val Phe Glu Gly Arg Glu Val Cys Gln Pro Lys Arg Ile Arg Pro
                355                 360                 365

Phe His Pro Pro Gly Ser Pro Trp Ala Asn Arg Pro Leu Pro Ala Ser
        370                 375                 380

Leu Ala Pro Thr Pro Thr Gly Pro Val His Glu Pro Val Gly Ser Leu
385                 390                 395                 400

Thr Pro Ala Pro Val Pro Gln Pro Leu Asp Pro Ala Pro Ala Val Thr
                405                 410                 415

Pro Glu Ala Ser His Leu Leu Glu Asp Pro Asp Glu Glu Thr Ser Gln
                420                 425                 430

Ala Val Lys Ala Leu Arg Glu Met Ala Asp Thr Val Ile Pro Gln Lys
                435                 440                 445

Glu Glu Ala Ala Ile Cys Gly Gln Met Asp Leu Ser His Pro Pro Pro
        450                 455                 460

Arg Gly His Leu Asp Glu Leu Thr Thr Thr Leu Glu Ser Met Thr Glu
465                 470                 475                 480

Asp Leu Asn Leu Asp Ser Pro Leu Thr Pro Glu Leu Asn Glu Ile Leu
                485                 490                 495

Asp Thr Phe Leu Asn Asp Glu Cys Leu Leu His Ala Met His Ile Ser
                500                 505                 510

Thr Gly Leu Ser Ile Phe Asp Thr Ser Leu Phe
        515                 520
```

<210> SEQ ID NO 49
<211> LENGTH: 6027
<212> TYPE: DNA
<213> ORGANISM: Homo sapiens

<400> SEQUENCE: 49

```
atggaacaga ccgtgctggt gccgccgggc ccggatagct ttaacttttt tacccgcgaa      60
agcctggcgg cgattgaacg ccgcattgcg gaagaaaaag cgaaaaaccc gaaaccggat     120
aaaaaagatg atgatgaaaa cggcccgaaa ccgaacagcg atctggaagc gggcaaaaac     180
ctgccgttta tttatggcga tattccgccg gaaatggtga cgaaccgct ggaagatctg      240 gatccgtatt atattaacaa aaaaacctt attgtgctga caaaggcaa agcgattttt       300 cgctttagcg cgaccagcgc gctgtatatt ctgacccgt ttaacccgct cgcaaaatt       360 gcgattaaaa ttctggtgca tagcctgttt agcatgctga ttatgtgcac cattctgacc     420
aactgcgtgt ttatgaccat gagcaacccg ccggattgga ccaaaaacgt ggaatatacc     480
tttaccggca tttatacctt tgaaagcctg attaaaatta ttgcgcgcgg ctttttgcctg     540 gaagatttta cctttctgcg cgatccgtgg aactggctgg attttaccgt gattaccttt     600
gcgtatgtga ccgaatttgt ggatctgggc aacgtgagcg cgctgcgcac ctttcgcgtg     660
```

-continued

```
ctgcgcgcgc tgaaaaccat tagcgtgatt ccgggcctga aaaccattgt gggcgcgctg      720
attcagagcg tgaaaaaact gagcgatgtg atgattctga ccgtgttttg cctgagcgtg      780
tttgcgctga ttggcctgca gctgtttatg ggcaacctgc gcaacaaatg cattcagtgg      840
ccgccgacca acgcgagcct ggaagaacat agcattgaaa aaaacattac cgtgaactat      900
aacggcaccc tgattaacga aaccgtgttt gaatttgatt ggaaaagcta tattcaggat      960
agccgctatc attattttct ggaaggcttt ctggatgcgc tgctgtgcgg caacagcagc     1020
gatgcgggcc agtgcccgga aggctatatg tgcgtgaaag cgggccgcaa cccgaactat     1080
ggctatacca gctttgatac ctttagctgg gcgtttctga gcctgtttcg cctgatgacc     1140
caggattttt gggaaaacct gtatcagctg accctgcgcg cggcgggcaa aacctatatg     1200
attttttttg tgctggtgat ttttctgggc agctttttatc tgattaacct gattctggcg     1260
gtggtggcga tggcgtatga agaacagaac caggcgaccc tggaagaagc ggaacagaaa     1320
gaagcggaat ttcagcagat gattgaacag ctgaaaaaac agcaggaagc ggcgcagcag     1380
gcggcgaccg cgaccgcgag cgaacatagc cgcgaaccga gcgcggcggg ccgcctgagc     1440
gatagcagca gcgaagcgag caaactgagc agcaaaagcg cgaaagaacg ccgcaaccgc     1500
cgcaaaaaac gcaaacagaa agaacagagc ggcggcgaag aaaaagatga agatgaattt     1560
cagaaaagcg aaagcgaaga tagcattcgc cgcaaaggct ttcgctttag cattgaaggc     1620
aaccgcctga cctatgaaaa acgctatagc agcccgcatc agagcctgct gagcattcgc     1680
ggcagcctgt ttagcccgcg ccgcaacagc cgcaccagcc tgtttagctt tcgcggccgc     1740
gcgaaagatg tgggcagcga aaacgatttt gcggatgatg aacatagcac ctttgaagat     1800
aacgaaagcc gccgcgatag cctgtttgtg ccgcgccgcc atggcgaacg ccgcaacagc     1860
aacctgagcc agaccagccg cagcagccgc atgctggcgg tgtttccggc gaacggcaaa     1920
atgcatagca ccgtggattg caacggcgtg gtgagcctgg tgggcggccc gagcgtgccg     1980
accagcccgg tgggccagct gctgccggaa gtgattattg ataaaccggc gaccgatgat     2040
aacggcacca ccaccgaaac cgaaatgcgc aaacgccgca gcagcagctt tcatgtgagc     2100
atggattttc tggaagatcc gagccagcgc cagcgcgcga tgagcattgc gagcattctg     2160
accaacaccg tggaagaact ggaagaaagc cgccagaaat gcccgccgtg ctggtataaa     2220
tttagcaaca ttttttctgat ttgggattgc agccgtatt ggctgaaagt gaaacatgtg     2280
gtgaacctgg tggtgatgga tccgtttgtg gatctggcga ttaccatttg cattgtgctg     2340
aacaccctgt ttatggcgat ggaacattat ccgatgaccg atcattttaa caacgtgctg     2400
accgtgggca acctggtgtt taccggcatt tttaccgcgg aaatgtttct gaaaattatt     2460
gcgatggatc cgtattatta tttttcaggaa ggctggaaca tttttgatgg ctttattgtg     2520
accctgagcc tggtggaact gggcctggcg aacgtggaag cctgagcgt gctgcgcagc     2580 tttcgcctgc tgcgcgtgtt taaactggcg aaaagctggc cgaccctgaa catgctgatt     2640
aaaattattg gcaacagcgt gggcgcgctg ggcaacctga ccctggtgct ggcgattatt     2700
gtgtttattt ttgcggtggt gggcatgcag ctgtttggca aaagctataa agattgcgtg     2760
tgcaaaattg cgagcgattg ccagctgccg cgctggcata tgaacgattt ttttcatagc     2820
tttctgattg tgtttcgcgt gctgtgcggc gaatggattg aaaaccatgtg ggattgcatg     2880 gaagtggcgg gccaggcgat gtgcctgacc gtgtttatga tggtgatggt gattggcaac     2940
ctggtggtgc tgaacctgtt tctggcgctg ctgctgagca gctttagcgc ggataacctg     3000
gcggcgaccg atgatgataa cgaaatgaac aacctgcaga ttgcggtgga tcgcatgcat     3060
```

-continued

```
aaaggcgtgg cgtatgtgaa acgcaaaatt tatgaattta ttcagcagag ctttattcgc   3120
aaacagaaaa ttctggatga aattaaaccg ctggatgatc tgaacaacaa aaaagatagc   3180
tgcatgagca accataccgc ggaaattggc aaagatctgg attatctgaa agatgtgaac   3240
ggcaccacca gcggcattgg caccggcagc agcgtggaaa aatatattat tgatgaaagc   3300
gattatatga gctttattaa caacccgagc ctgaccgtga ccgtgccgat tgcggtgggc   3360
gaaagcgatt ttgaaaacct gaacaccgaa gattttagca gcgaaagcga tctggaagaa   3420
agcaaagaaa aactgaacga aagcagcagc agcagcgaag cagcaccgt ggatattggc    3480 gcgccggtgg aagaacagcc ggtggtggaa ccggaagaaa ccctggaacc ggaagcgtgc   3540
tttaccgaag gctgcgtgca gcgctttaaa tgctgccaga ttaacgtgga agaaggccgc   3600
ggcaaacagt ggtggaacct cgcgccgcacc tgctttcgca ttgtggaaca taactggttt   3660 gaaacctta ttgtgtttat gattctgctg agcagcggcg cgctggcgtt tgaagatatt    3720
tatattgatc agcgcaaaac cattaaaacc atgctggaat atgcggataa agtgtttacc   3780
tatattttta ttctggaaat gctgctgaaa tgggtggcgt atggctatca gacctatttt   3840
accaacgcgt ggtgctggct ggattttctg attgtggatg tgagcctggt gagcctgacc   3900
gcgaacgcgc tgggctatag cgaactgggc gcgattaaaa gcctgcgcac cctgcgcgcg   3960
ctgcgcccgc tgcgcgcgct gagccgcttt gaaggcatgc gcgtggtggt gaacgcgctg   4020
ctgggcgcga ttccgagcat tatgaacgtg ctgctggtgt gcctgatttt ttggctgatt   4080
tttagcatta tgggcgtgaa cctgtttgcg ggcaaatttt atcattgcat taacaccacc   4140
accggcgatc gctttgatat tgaagatgtg aacaaccata ccgattgcct gaaactgatt   4200
gaacgcaacg aaaccgcgcg ctggaaaaac gtgaaagtga actttgataa cgtgggcttt   4260
ggctatctga gcctgctgca ggtggcgacc tttaaaggct ggatggatat tatgtatgcg   4320
gcggtggata gccgcaacgt ggaactgcag ccgaaatatg aagaaagcct gtatatgtat   4380
ctgtattttg tgattttttat tattttttggc agctttttta ccctgaacct gtttattggc   4440
gtgattattg ataactttaa ccagcagaaa aaaaaatttg gcggccagga tatttttatg   4500
accgaagaac agaaaaaata ttataacgcg atgaaaaaac tgggcagcaa aaaaccgcag   4560
aaaccgattc cgcgcccggg caacaaattt cagggcatgg tgtttgattt tgtgacccgc   4620
caggtgtttg atattagcat tatgattctg atttgcctga acatggtgac catgatggtg   4680
gaaaccgatg atcagagcga atatgtgacc accattctga ccgcgcattaa cctggtgttt   4740 attgtgctgt ttaccggcga atgcgtgctg aaactgatta gcctgcgcca ttattattttt   4800 accattggct ggaacatttt tgattttgtg gtggtgattc tgagcattgt gggcatgtttt   4860 ctggcggaac tgattgaaaa atattttgtg agcccgaccc tgtttcgcgt gattcgcctg   4920
gcgcgcattg ccgcattct cgcctgatt aaaggcgcga aaggcattcg caccctgctg    4980
tttgcgctga tgatgagcct gccggcgctg tttaacattg cctgctgct gtttctggtg   5040 atgtttattt atgcgatttt tggcatgagc aactttgcgt atgtgaaacg cgaagtgggc   5100
attgatgata tgtttaactt tgaaaccttt ggcaacagca tgatttgcct gtttcagatt   5160
accaccagcg cgggctggga tggcctgctg cgcgccgattc tgaacagcaa accgccggat   5220
tgcgatccga acaaagtgaa cccgggcagc agcgtgaaag cgattgcgg caacccgagc    5280 gtgggcattt tttttttttgt gagctatatt attattagct ttctggtggt ggtgaacatg   5340
tatattgcgg tgattctgga aaactttagc gtggcgaccg aagaaagcgc ggaaccgctg   5400
```

```
agcgaagatg attttgaaat gtttttatgaa gtgtgggaaa aatttgatcc ggatgcgacc    5460
cagtttatgg aatttgaaaa actgagccag tttgcggcgg cgctggaacc gccgctgaac    5520
ctgccgcagc cgaacaaact gcagctgatt gcgatggatc tgccgatggt gagcggcgat    5580
cgcattcatt gcctggatat tctgtttgcg tttaccaaac gcgtgctggg cgaaagcggc    5640
gaaatggatg cgctgcgcat tcagatggaa gaacgcttta tggcgagcaa cccgagcaaa    5700
gtgagctatc agccgattac caccaccctg aaacgcaaac aggaagaagt gagcgcggtg    5760
attattcagc gcgcgtatcg ccgccatctg ctgaaacgca ccgtgaaaca ggcgagcttt    5820
acctataaca aaacaaaat taaaggcggc gcgaacctgc tgattaaaga agatatgatt    5880
attgatcgca ttaacgaaaa cagcattacc gaaaaaaccg atctgaccat gagcaccgcg    5940
gcgtgcccgc cgagctatga tcgcgtgacc aaaccgattg tggaaaaaca tgaacaggaa    6000
ggcaaagatg aaaaagcgaa aggcaaa    6027
```

```
<210> SEQ ID NO 50
<211> LENGTH: 2009
<212> TYPE: PRT
<213> ORGANISM: Homo sapiens

<400> SEQUENCE: 50

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Asp Glu Asn Gly
            35                  40                  45

Pro Lys Pro Asn Ser Asp Leu Glu Ala Gly Lys Asn Leu Pro Phe Ile
        50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
```

-continued

```
                 260                  265                   270

Leu Arg Asn Lys Cys Ile Gln Trp Pro Pro Thr Asn Ala Ser Leu Glu
        275                  280                  285

Glu His Ser Ile Glu Lys Asn Ile Thr Val Asn Tyr Asn Gly Thr Leu
        290                  295                  300

Ile Asn Glu Thr Val Phe Glu Phe Asp Trp Lys Ser Tyr Ile Gln Asp
305                  310                  315                  320

Ser Arg Tyr His Tyr Phe Leu Glu Gly Phe Leu Asp Ala Leu Leu Cys
                325                  330                  335

Gly Asn Ser Ser Asp Ala Gly Gln Cys Pro Glu Gly Tyr Met Cys Val
            340                  345                  350

Lys Ala Gly Arg Asn Pro Asn Tyr Gly Tyr Thr Ser Phe Asp Thr Phe
        355                  360                  365

Ser Trp Ala Phe Leu Ser Leu Phe Arg Leu Met Thr Gln Asp Phe Trp
    370                  375                  380

Glu Asn Leu Tyr Gln Leu Thr Leu Arg Ala Ala Gly Lys Thr Tyr Met
385                  390                  395                  400

Ile Phe Phe Val Leu Val Ile Phe Leu Gly Ser Phe Tyr Leu Ile Asn
                405                  410                  415

Leu Ile Leu Ala Val Val Ala Met Ala Tyr Glu Glu Gln Asn Gln Ala
            420                  425                  430

Thr Leu Glu Glu Ala Glu Gln Lys Glu Ala Glu Phe Gln Gln Met Ile
            435                  440                  445

Glu Gln Leu Lys Lys Gln Gln Glu Ala Ala Gln Gln Ala Ala Thr Ala
    450                  455                  460

Thr Ala Ser Glu His Ser Arg Glu Pro Ser Ala Ala Gly Arg Leu Ser
465                  470                  475                  480

Asp Ser Ser Ser Glu Ala Ser Lys Leu Ser Ser Lys Ser Ala Lys Glu
                485                  490                  495

Arg Arg Asn Arg Arg Lys Lys Arg Lys Gln Lys Glu Gln Ser Gly Gly
            500                  505                  510

Glu Glu Lys Asp Glu Asp Glu Phe Gln Lys Ser Glu Ser Glu Asp Ser
        515                  520                  525

Ile Arg Arg Lys Gly Phe Arg Phe Ser Ile Glu Gly Asn Arg Leu Thr
    530                  535                  540

Tyr Glu Lys Arg Tyr Ser Ser Pro His Gln Ser Leu Leu Ser Ile Arg
545                  550                  555                  560

Gly Ser Leu Phe Ser Pro Arg Arg Asn Ser Arg Thr Ser Leu Phe Ser
                565                  570                  575

Phe Arg Gly Arg Ala Lys Asp Val Gly Ser Glu Asn Asp Phe Ala Asp
            580                  585                  590

Asp Glu His Ser Thr Phe Glu Asp Asn Glu Ser Arg Arg Asp Ser Leu
        595                  600                  605

Phe Val Pro Arg Arg His Gly Glu Arg Arg Asn Ser Asn Leu Ser Gln
    610                  615                  620

Thr Ser Arg Ser Ser Arg Met Leu Ala Val Phe Pro Ala Asn Gly Lys
625                  630                  635                  640

Met His Ser Thr Val Asp Cys Asn Gly Val Val Ser Leu Val Gly Gly
                645                  650                  655

Pro Ser Val Pro Thr Ser Pro Val Gly Gln Leu Leu Pro Glu Val Ile
            660                  665                  670

Ile Asp Lys Pro Ala Thr Asp Asp Asn Gly Thr Thr Thr Glu Thr Glu
        675                  680                  685
```

```
Met Arg Lys Arg Arg Ser Ser Ser Phe His Val Ser Met Asp Phe Leu
    690             695                 700

Glu Asp Pro Ser Gln Arg Gln Arg Ala Met Ser Ile Ala Ser Ile Leu
705             710                 715                 720

Thr Asn Thr Val Glu Glu Leu Glu Glu Ser Arg Gln Lys Cys Pro Pro
            725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
            755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
            805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
            835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
                900                 905                 910

Gly Lys Ser Tyr Lys Asp Cys Val Cys Lys Ile Ala Ser Asp Cys Gln
            915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
                980                 985                 990

Ser Ser Phe Ser Ala Asp Asn Leu  Ala Ala Thr Asp Asp  Asp Asn Glu
            995                 1000                1005

Met Asn Asn Leu Gln Ile Ala  Val Asp Arg Met His  Lys Gly Val
    1010                1015                1020

Ala Tyr Val Lys Arg Lys Ile  Tyr Glu Phe Ile Gln  Gln Ser Phe
    1025                1030                1035

Ile Arg Lys Gln Lys Ile Leu  Asp Glu Ile Lys Pro  Leu Asp Asp
    1040                1045                1050

Leu Asn Asn Lys Lys Asp Ser  Cys Met Ser Asn His  Thr Ala Glu
    1055                1060                1065

Ile Gly Lys Asp Leu Asp Tyr  Leu Lys Asp Val Asn  Gly Thr Thr
    1070                1075                1080

Ser Gly Ile Gly Thr Gly Ser  Ser Val Glu Lys Tyr  Ile Ile Asp
    1085                1090                1095
```

-continued

```
Glu Ser  Asp Tyr Met Ser Phe  Ile Asn Asn Pro Ser  Leu Thr Val
    1100                 1105              1110

Thr Val  Pro Ile Ala Val Gly  Glu Ser Asp Phe Glu  Asn Leu Asn
    1115                 1120              1125

Thr Glu  Asp Phe Ser Ser Glu  Ser Asp Leu Glu Glu  Ser Lys Glu
    1130                 1135              1140

Lys Leu  Asn Glu Ser Ser Ser  Ser Ser Glu Gly Ser  Thr Val Asp
    1145                 1150              1155

Ile Gly  Ala Pro Val Glu Glu  Gln Pro Val Val Glu  Pro Glu Glu
    1160                 1165              1170

Thr Leu  Glu Pro Glu Ala Cys  Phe Thr Glu Gly Cys  Val Gln Arg
    1175                 1180              1185

Phe Lys  Cys Cys Gln Ile Asn  Val Glu Glu Gly Arg  Gly Lys Gln
    1190                 1195              1200

Trp Trp  Asn Leu Arg Arg Thr  Cys Phe Arg Ile Val  Glu His Asn
    1205                 1210              1215

Trp Phe  Glu Thr Phe Ile Val  Phe Met Ile Leu Leu  Ser Ser Gly
    1220                 1225              1230

Ala Leu  Ala Phe Glu Asp Ile  Tyr Ile Asp Gln Arg  Lys Thr Ile
    1235                 1240              1245

Lys Thr  Met Leu Glu Tyr Ala  Asp Lys Val Phe Thr  Tyr Ile Phe
    1250                 1255              1260

Ile Leu  Glu Met Leu Leu Lys  Trp Val Ala Tyr Gly  Tyr Gln Thr
    1265                 1270              1275

Tyr Phe  Thr Asn Ala Trp Cys  Trp Leu Asp Phe Leu  Ile Val Asp
    1280                 1285              1290

Val Ser  Leu Val Ser Leu Thr  Ala Asn Ala Leu Gly  Tyr Ser Glu
    1295                 1300              1305

Leu Gly  Ala Ile Lys Ser Leu  Arg Thr Leu Arg Ala  Leu Arg Pro
    1310                 1315              1320

Leu Arg  Ala Leu Ser Arg Phe  Glu Gly Met Arg Val  Val Val Asn
    1325                 1330              1335

Ala Leu  Leu Gly Ala Ile Pro  Ser Ile Met Asn Val  Leu Leu Val
    1340                 1345              1350

Cys Leu  Ile Phe Trp Leu Ile  Phe Ser Ile Met Gly  Val Asn Leu
    1355                 1360              1365

Phe Ala  Gly Lys Phe Tyr His  Cys Ile Asn Thr Thr  Thr Gly Asp
    1370                 1375              1380

Arg Phe  Asp Ile Glu Asp Val  Asn Asn His Thr Asp  Cys Leu Lys
    1385                 1390              1395

Leu Ile  Glu Arg Asn Glu Thr  Ala Arg Trp Lys Asn  Val Lys Val
    1400                 1405              1410

Asn Phe  Asp Asn Val Gly Phe  Gly Tyr Leu Ser Leu  Leu Gln Val
    1415                 1420              1425

Ala Thr  Phe Lys Gly Trp Met  Asp Ile Met Tyr Ala  Ala Val Asp
    1430                 1435              1440

Ser Arg  Asn Val Glu Leu Gln  Pro Lys Tyr Glu Glu  Ser Leu Tyr
    1445                 1450              1455

Met Tyr  Leu Tyr Phe Val Ile  Phe Ile Ile Phe Gly  Ser Phe Phe
    1460                 1465              1470

Thr Leu  Asn Leu Phe Ile Gly  Val Ile Ile Asp Asn  Phe Asn Gln
    1475                 1480              1485

Gln Lys  Lys Lys Phe Gly Gly  Gln Asp Ile Phe Met  Thr Glu Glu
```

-continued

```
        1490              1495              1500

Gln Lys Lys Tyr Tyr Asn Ala Met Lys Lys Leu Gly Ser Lys Lys
    1505              1510              1515

Pro Gln Lys Pro Ile Pro Arg Pro Gly Asn Lys Phe Gln Gly Met
    1520              1525              1530

Val Phe Asp Phe Val Thr Arg Gln Val Phe Asp Ile Ser Ile Met
    1535              1540              1545

Ile Leu Ile Cys Leu Asn Met Val Thr Met Met Val Glu Thr Asp
    1550              1555              1560

Asp Gln Ser Glu Tyr Val Thr Thr Ile Leu Ser Arg Ile Asn Leu
    1565              1570              1575

Val Phe Ile Val Leu Phe Thr Gly Glu Cys Val Leu Lys Leu Ile
    1580              1585              1590

Ser Leu Arg His Tyr Tyr Phe Thr Ile Gly Trp Asn Ile Phe Asp
    1595              1600              1605

Phe Val Val Val Ile Leu Ser Ile Val Gly Met Phe Leu Ala Glu
    1610              1615              1620

Leu Ile Glu Lys Tyr Phe Val Ser Pro Thr Leu Phe Arg Val Ile
    1625              1630              1635

Arg Leu Ala Arg Ile Gly Arg Ile Leu Arg Leu Ile Lys Gly Ala
    1640              1645              1650

Lys Gly Ile Arg Thr Leu Leu Phe Ala Leu Met Met Ser Leu Pro
    1655              1660              1665

Ala Leu Phe Asn Ile Gly Leu Leu Leu Phe Leu Val Met Phe Ile
    1670              1675              1680

Tyr Ala Ile Phe Gly Met Ser Asn Phe Ala Tyr Val Lys Arg Glu
    1685              1690              1695

Val Gly Ile Asp Asp Met Phe Asn Phe Glu Thr Phe Gly Asn Ser
    1700              1705              1710

Met Ile Cys Leu Phe Gln Ile Thr Thr Ser Ala Gly Trp Asp Gly
    1715              1720              1725

Leu Leu Ala Pro Ile Leu Asn Ser Lys Pro Pro Asp Cys Asp Pro
    1730              1735              1740

Asn Lys Val Asn Pro Gly Ser Ser Val Lys Gly Asp Cys Gly Asn
    1745              1750              1755

Pro Ser Val Gly Ile Phe Phe Phe Val Ser Tyr Ile Ile Ile Ser
    1760              1765              1770

Phe Leu Val Val Val Asn Met Tyr Ile Ala Val Ile Leu Glu Asn
    1775              1780              1785

Phe Ser Val Ala Thr Glu Glu Ser Ala Glu Pro Leu Ser Glu Asp
    1790              1795              1800

Asp Phe Glu Met Phe Tyr Glu Val Trp Glu Lys Phe Asp Pro Asp
    1805              1810              1815

Ala Thr Gln Phe Met Glu Phe Glu Lys Leu Ser Gln Phe Ala Ala
    1820              1825              1830

Ala Leu Glu Pro Pro Leu Asn Leu Pro Gln Pro Asn Lys Leu Gln
    1835              1840              1845

Leu Ile Ala Met Asp Leu Pro Met Val Ser Gly Asp Arg Ile His
    1850              1855              1860

Cys Leu Asp Ile Leu Phe Ala Phe Thr Lys Arg Val Leu Gly Glu
    1865              1870              1875

Ser Gly Glu Met Asp Ala Leu Arg Ile Gln Met Glu Glu Arg Phe
    1880              1885              1890
```

```
Met Ala Ser Asn Pro Ser Lys Val Ser Tyr Gln Pro Ile Thr Thr
    1895              1900              1905

Thr Leu Lys Arg Lys Gln Glu Glu Val Ser Ala Val Ile Ile Gln
    1910              1915              1920

Arg Ala Tyr Arg Arg His Leu Leu Lys Arg Thr Val Lys Gln Ala
    1925              1930              1935

Ser Phe Thr Tyr Asn Lys Asn Lys Ile Lys Gly Gly Ala Asn Leu
    1940              1945              1950

Leu Ile Lys Glu Asp Met Ile Ile Asp Arg Ile Asn Glu Asn Ser
    1955              1960              1965

Ile Thr Glu Lys Thr Asp Leu Thr Met Ser Thr Ala Ala Cys Pro
    1970              1975              1980

Pro Ser Tyr Asp Arg Val Thr Lys Pro Ile Val Glu Lys His Glu
    1985              1990              1995

Gln Glu Gly Lys Asp Glu Lys Ala Lys Gly Lys
    2000              2005
```

```
<210> SEQ ID NO 51
<211> LENGTH: 1470
<212> TYPE: DNA
<213> ORGANISM: Homo sapiens

<400> SEQUENCE: 51
atggatctgc tggtggatga actgtttgcg gatatgaacg cggatggcgc gagcccgccg      60
ccgccgcgcc cggcgggcgg cccgaaaaac accccggcgg cgccgccgct gtatgcgacc     120
ggccgcctga gccaggcgca gctgatgccg agcccgccga tgccggtgcc gccggcggcg     180
ctgtttaacc gcctgctgga tgatctgggc tttagcgcgg gcccggcgct gtgcaccatg     240
ctggatacct ggaacgaaga tctgtttagc gcgctgccga ccaacgcgga tctgtatcgc     300
gaatgcaaat ttctgagcac cctgccgagc gatgtggtgg aatggggcga tgcgtatgtg     360
ccggaacgca cccagattga tattcgcgcg catggcgatg tggcgtttcc gaccctgccg     420
gcgacccgcg atggcctggg cctgtattat gaagcgctga gccgcttttt tcatgcggaa     480
ctgcgcgcgc gcgaagaaag ctatcgcacc gtgctggcga cttttgcag cgcgctgtat     540 cgctatctgc gcgcgagcgt gcgccagctg catcgccagg cgcatatgcg cggccgcgat     600
cgcgatctgg cgaaatgct gcgcgcgacc attgcggatc gctattatcg cgaaaccgcg     660
cgcctggcgc gcgtgctgtt tctgcatctg tatctgtttc tgacccgcga aattctgtgg     720
gcggcgtatg cggaacagat gatgcgcccg gatctgtttg attgcctgtg ctgcgatctg     780
gaaagctggc gccagctggc gggcctgttt cagccgttta tgtttgtgaa cggcgcgctg     840
accgtgcgcg gcgtgccgat tgaagcgcgc gcctgcgcg aactgaacca tattcgcgaa     900
catctgaacc tgccgctggt gcgcagcgcg gcgaccgaag aaccgggcgc gccgctgacc     960
accccgccga ccctgcatgg caaccaggcg cgcgcgagcg ctatttat ggtgctgatt     1020 cgcgcgaaac tggatagcta tagcagcttt accaccagcc gagcgaagc ggtgatgcgc     1080 gaacatgcgt atagccgcgc gcgcaccaaa aacaactatg cagcaccat tgaaggcctg     1140 ctggatctgc ggatgatga tgcgccggaa gaagcgggcc tggcggcgcc gcgcctgagc     1200
tttctgccgg cgggccatac ccgccgcctg agcaccgcgc gccgaccga tgtgagcctg     1260 ggcgatgaac tgcatctgga tggcgaagat gtggcgatgg cgcatgcgga tgcgctggat     1320
gattttgatc tggatatgct gggcgatggc gatagcccgg gcccgggctt taccccgcat     1380
```

-continued

```
gatagcgcgc cgtatggcgc gctggatatg gcggattttg aatttgaaca gatgtttacc          1440
gatgcgctgg gcattgatga atatggcggc                                            1470
```

<210> SEQ ID NO 52
<211> LENGTH: 490
<212> TYPE: PRT
<213> ORGANISM: Homo sapiens

<400> SEQUENCE: 52

```
Met Asp Leu Leu Val Asp Glu Leu Phe Ala Asp Met Asn Ala Asp Gly
1               5                   10                  15

Ala Ser Pro Pro Pro Arg Pro Ala Gly Gly Pro Lys Asn Thr Pro
            20                  25                  30

Ala Ala Pro Pro Leu Tyr Ala Thr Gly Arg Leu Ser Gln Ala Gln Leu
        35                  40                  45

Met Pro Ser Pro Pro Met Pro Val Pro Pro Ala Ala Leu Phe Asn Arg
    50                  55                  60

Leu Leu Asp Asp Leu Gly Phe Ser Ala Gly Pro Ala Leu Cys Thr Met
65                  70                  75                  80

Leu Asp Thr Trp Asn Glu Asp Leu Phe Ser Ala Leu Pro Thr Asn Ala
                85                  90                  95

Asp Leu Tyr Arg Glu Cys Lys Phe Leu Ser Thr Leu Pro Ser Asp Val
            100                 105                 110

Val Glu Trp Gly Asp Ala Tyr Val Pro Glu Arg Thr Gln Ile Asp Ile
            115                 120                 125

Arg Ala His Gly Asp Val Ala Phe Pro Thr Leu Pro Ala Thr Arg Asp
        130                 135                 140

Gly Leu Gly Leu Tyr Tyr Glu Ala Leu Ser Arg Phe Phe His Ala Glu
145                 150                 155                 160

Leu Arg Ala Arg Glu Glu Ser Tyr Arg Thr Val Leu Ala Asn Phe Cys
                165                 170                 175

Ser Ala Leu Tyr Arg Tyr Leu Arg Ala Ser Val Arg Gln Leu His Arg
            180                 185                 190

Gln Ala His Met Arg Gly Arg Asp Arg Asp Leu Gly Glu Met Leu Arg
            195                 200                 205

Ala Thr Ile Ala Asp Arg Tyr Tyr Arg Glu Thr Ala Arg Leu Ala Arg
        210                 215                 220

Val Leu Phe Leu His Leu Tyr Leu Phe Leu Thr Arg Glu Ile Leu Trp
225                 230                 235                 240

Ala Ala Tyr Ala Glu Gln Met Met Arg Pro Asp Leu Phe Asp Cys Leu
                245                 250                 255

Cys Cys Asp Leu Glu Ser Trp Arg Gln Leu Ala Gly Leu Phe Gln Pro
            260                 265                 270

Phe Met Phe Val Asn Gly Ala Leu Thr Val Arg Gly Val Pro Ile Glu
            275                 280                 285

Ala Arg Arg Leu Arg Glu Leu Asn His Ile Arg Glu His Leu Asn Leu
        290                 295                 300

Pro Leu Val Arg Ser Ala Ala Thr Glu Glu Pro Gly Ala Pro Leu Thr
305                 310                 315                 320

Thr Pro Pro Thr Leu His Gly Asn Gln Ala Arg Ala Ser Gly Tyr Phe
                325                 330                 335

Met Val Leu Ile Arg Ala Lys Leu Asp Ser Tyr Ser Ser Phe Thr Thr
            340                 345                 350

Ser Pro Ser Glu Ala Val Met Arg Glu His Ala Tyr Ser Arg Ala Arg
```

```
          355              360              365
Thr Lys Asn Asn Tyr Gly Ser Thr Ile Glu Gly Leu Leu Asp Leu Pro
         370              375              380

Asp Asp Asp Ala Pro Glu Glu Ala Gly Leu Ala Ala Pro Arg Leu Ser
385              390              395              400

Phe Leu Pro Ala Gly His Thr Arg Arg Leu Ser Thr Ala Pro Pro Thr
                   405              410              415

Asp Val Ser Leu Gly Asp Glu Leu His Leu Asp Gly Glu Asp Val Ala
                   420              425              430

Met Ala His Ala Asp Ala Leu Asp Asp Phe Asp Leu Asp Met Leu Gly
                   435              440              445

Asp Gly Asp Ser Pro Gly Pro Gly Phe Thr Pro His Asp Ser Ala Pro
         450              455              460

Tyr Gly Ala Leu Asp Met Ala Asp Phe Glu Phe Glu Gln Met Phe Thr
465              470              475              480

Asp Ala Leu Gly Ile Asp Glu Tyr Gly Gly
                   485              490

<210> SEQ ID NO 53
<211> LENGTH: 2570
<212> TYPE: DNA
<213> ORGANISM: Homo sapiens

<400> SEQUENCE: 53
agcgcgcagg cgcggccgga ttccgggcag tgacgcgacg gcgggccgcg cggcgcattt      60
ccgcctctgg cgaatggctc gtctgtagtg cacgccgcgg gcccagctgc accccggcc     120 ccgcccccgg accccggcc atggacgaac tgttcccct catcttcccg gcagagccag       180
cccaggcctc tggcccctat gtggagatca ttgagcagcc caagcagcgg ggcatgcgct     240
tccgctacaa gtgcgagggg cgctccgcgg gcagcatccc aggcgagagg agcacagata     300
ccaccaagac ccacccacc atcaagatca atggctacac aggaccaggg acagtgcgca       360
tctccctggt caccaaggac cctcctcacc ggcctcaccc ccacgagctt gtaggaaagg     420
actgccggga tggcttctat gaggctgagc tctgcccgga ccgctgcatc cacagtttcc     480
agaacctggg aatccagtgt gtgaagaagc gggacctgga gcaggctatc agtcagcgca     540
tccagaccaa caacaacccc ttccaagaag agcagcgtgg ggactacgac ctgaatgctg     600
tgcggctctg cttccaggtg acagtgcggg acccatcagg caggcccctc cgcctgccgc     660
ctgtcctttc tcatcccatc tttgacaatc gtgcccccaa cactgccgag ctcaagatct     720
gccgagtgaa ccgaaactct ggcagctgcc tcggtgggga tgagatcttc ctactgtgtg     780
acaaggtgca gaaagaggac attgaggtgt atttcacggg accaggctgg gaggcccgag     840
gctccttttc gcaagctgat gtgcaccgac aagtggccat tgtgttccgg acccctccct     900
acgcagaccc cagcctgcag gctcctgtgc gtgtctccat gcagctgcgg cggccttccg     960
accgggagct cagtgagccc atggaattcc agtacctgcc agatacagac gatcgtcacc    1020
ggattgagga gaaacgtaaa aggacatatg agaccttcaa gagcatcatg aagaagagtc    1080
ctttcagcgg acccaccgac ccccggcctc cacctcgacg cattgctgtg ccttcccgca    1140
gctcagcttc tgtccccaag ccagcacccc agccctatcc ctttacgtca tccctgagca    1200
ccatcaacta tgatgagttt cccaccatgg tgtttccttc tgggcagatc agccaggcct    1260
cggccttggc cccggcccct ccccaagtcc tgccccaggc tccagcccct gcccctgctc    1320
cagccatggt atcagctctg gcccaggccc cagcccctgt cccagtccta gccccaggcc    1380
```

```
ctcctcaggc tgtggcccca cctgcccca agcccaccca ggctggggaa ggaacgctgt   1440
cagaggccct gctgcagctg cagtttgatg atgaagacct gggggccttg cttggcaaca   1500
gcacagaccc agctgtgttc acagacctgg catccgtcga caactccgag tttcagcagc   1560
tgctgaacca gggcatacct gtggcccccc acacaactga gcccatgctg atggagtacc   1620
ctgaggctat aactcgccta gtgacagggg cccagaggcc ccccgaccca gctcctgctc   1680
cactgggggc cccgggggctc cccaatggcc tcctttcagg agatgaagac ttctcctcca   1740
ttgcggacat ggacttctca gccctgctga gtcagatcag ctcctaaggg ggtgacgcct   1800
gccctcccca gagcactggg ttgcagggga ttgaagccct ccaaaagcac ttacggattc   1860 tggtgggggtg tgttccaact gcccccaact ttgtggatgt cttccttgga gggggggagcc   1920 atattttatt ctttttattgt cagtatctgt atctctctct ctttttggag gtgcttaagc   1980
agaagcatta acttctctgg aaagggggga gctggggaaa ctcaaacttt tccctgtcc   2040 tgatggtcag ctcccttctc tgtagggaac tctgggggtcc cccatcccca tcctccagct   2100
tctggtactc tcctagagac agaagcaggc tggaggtaag gcctttgagc ccacaaagcc   2160
ttatcaagtg tcttccatca tggattcatt acagcttaat caaaataacg ccccagatac   2220
cagcccctgt atggcactgg cattgtccct gtgcctaaca ccagcgtttg aggggctggc   2280
cttcctgccc tacagaggtc tctgccggct ctttccttgc tcaaccatgg ctgaaggaaa   2340
ccagtgcaac agcactggct ctctccagga tccagaaggg gtttggtctg ggacttcctt   2400
gctctccctc ttctcaagtg ccttaatagt agggtaagtt gttaagagtg ggggagagca   2460
ggctggcagc tctccagtca ggaggcatag tttttactga acaatcaaag cacttggact   2520 cttgctctttt ctactctgaa ctaataaatc tgttgccaag ctggctagaa            2570

<210> SEQ ID NO 54
<211> LENGTH: 548
<212> TYPE: PRT
<213> ORGANISM: Homo sapiens

<400> SEQUENCE: 54

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Glu Glu
    130                 135                 140

Gln Arg Gly Asp Tyr Asp Leu Asn Ala Val Arg Leu Cys Phe Gln Val
145                 150                 155                 160
```

```
Thr Val Arg Asp Pro Ser Gly Arg Pro Leu Arg Leu Pro Pro Val Leu
            165                 170             175

Ser His Pro Ile Phe Asp Asn Arg Ala Pro Asn Thr Ala Glu Leu Lys
            180             185                 190

Ile Cys Arg Val Asn Arg Asn Ser Gly Ser Cys Leu Gly Gly Asp Glu
            195             200             205

Ile Phe Leu Leu Cys Asp Lys Val Gln Lys Glu Asp Ile Glu Val Tyr
            210             215             220

Phe Thr Gly Pro Gly Trp Glu Ala Arg Gly Ser Phe Ser Gln Ala Asp
225             230             235             240

Val His Arg Gln Val Ala Ile Val Phe Arg Thr Pro Pro Tyr Ala Asp
            245             250             255

Pro Ser Leu Gln Ala Pro Val Arg Val Ser Met Gln Leu Arg Arg Pro
            260             265             270

Ser Asp Arg Glu Leu Ser Glu Pro Met Glu Phe Gln Tyr Leu Pro Asp
            275             280             285

Thr Asp Asp Arg His Arg Ile Glu Glu Lys Arg Lys Arg Thr Tyr Glu
290             295             300

Thr Phe Lys Ser Ile Met Lys Lys Ser Pro Phe Ser Gly Pro Thr Asp
305             310             315             320

Pro Arg Pro Pro Pro Arg Arg Ile Ala Val Pro Ser Arg Ser Ser Ala
            325             330             335

Ser Val Pro Lys Pro Ala Pro Gln Pro Tyr Pro Phe Thr Ser Ser Leu
            340             345             350

Ser Thr Ile Asn Tyr Asp Glu Phe Pro Thr Met Val Phe Pro Ser Gly
            355             360             365

Gln Ile Ser Gln Ala Ser Ala Leu Ala Pro Ala Pro Pro Gln Val Leu
            370             375             380

Pro Gln Ala Pro Ala Pro Ala Pro Ala Pro Ala Met Val Ser Ala Leu
385             390             395             400

Ala Gln Ala Pro Ala Pro Val Pro Val Leu Ala Pro Gly Pro Pro Gln
            405             410             415

Ala Val Ala Pro Pro Ala Pro Lys Pro Thr Gln Ala Gly Glu Gly Thr
            420             425             430

Leu Ser Glu Ala Leu Leu Gln Leu Gln Phe Asp Asp Glu Asp Leu Gly
            435             440             445

Ala Leu Leu Gly Asn Ser Thr Asp Pro Ala Val Phe Thr Asp Leu Ala
            450             455             460

Ser Val Asp Asn Ser Glu Phe Gln Gln Leu Leu Asn Gln Gly Ile Pro
465             470             475             480

Val Ala Pro His Thr Thr Glu Pro Met Leu Met Glu Tyr Pro Glu Ala
            485             490             495

Ile Thr Arg Leu Val Thr Gly Ala Gln Arg Pro Pro Asp Pro Ala Pro
            500             505             510

Ala Pro Leu Gly Ala Pro Gly Leu Pro Asn Gly Leu Leu Ser Gly Asp
            515             520             525

Glu Asp Phe Ser Ser Ile Ala Asp Met Asp Phe Ser Ala Leu Leu Ser
            530             535             540

Gln Ile Ser Ser
545
```

<210> SEQ ID NO 55
<211> LENGTH: 1815
<212> TYPE: DNA

<213> ORGANISM: Homo sapiens

<400> SEQUENCE: 55

```
atgcgcccga aaaaagatgg cctggaagat tttctgcgcc tgaccccgga aattaaaaaa        60
cagctgggca gcctggtgag cgattattgc aacgtgctga acaaagaatt taccgcgggc       120
agcgtggaaa ttaccctgcg cagctataaa atttgcaaag cgtttattaa cgaagcgaaa       180
gcgcatggcc gcgaatgggg cggcctgatg cgaccctga acatttgcaa cttttgggcg       240
attctgcgca acaaccgcgt cgcgccgccgc gcggaaaacg cgggcaacga tgcgtgcagc       300
attgcgtgcc cgattgtgat cgcgtatgtg ctggatcatc tgattgtggt gaccgatcgc       360
ttttttattc aggcgccgag caaccgcgtg atgattccgg cgaccattgg caccgcgatg       420
tataaactgc tgaaacatag ccgcgtgcgc gcgtatacct atagcaaagt gctgggcgtg       480
gatcgcgcgg cgattatggc gagcggcaaa caggtggtgg aacatctgaa ccgcatggaa       540
aaagaaggcc tgctgagcag caaatttaaa gcgtttttgca aatgggtgtt tacctatccg       600
gtgctggaag aaatgtttca gaccatggtg agcagcaaaa ccggccatct gaccgatgat       660
gtgaaagatg tgcgcgcgct gattaaaacc ctgccgcgcg cgagctatag cagccatgcg       720
ggccagcgca gctatgtgag cggcgtgctg ccggcgtgcc tgctgagcac caaaagcaaa       780
gcggtggaaa ccccgattct ggtgagcggc gcggatcgca tggatgaaga actgatgggc       840
aacgatggcg gcgcgagcca taccgaagcg cgctatagcg aaagcggcca gtttcatgcg       900
tttaccgatg aactggaaag cctgccgagc ccgaccatgc cgctgaaacc gggcgcgcag       960
agcgcggatt cgggcgatag cagcagcagc agcagcgata cgggcaacag cgataccgaa      1020
cagagcgaac gcgaagaagc gcgcgcggaa cgccgcgcc tgcgcgcgcc gaaaagccgc      1080
cgcaccagcc gcccgaaccg cggccagacc ccgtgcccga caacgcggc ggaaccggaa      1140
cagccgtgga ttgcggcggt gcatcaggaa agcgatgaac gcccgatttt tccgcatccg      1200
agcaaaccga cctttctgcc gccggtgaaa cgcaaaaaag gcctgcgcga tagccgcgaa      1260
ggcatgtttc tgccgaaacc ggaagcgggc agcgcgatta gcgatgtgtt tgaaggccgc      1320
gaagtgtgcc agccgaaacg cattcgcccg tttcatccgc cgggcagccc gtgggcgaac      1380
cgcccgctgc cggcgagcct ggcgccgacc ccgaccggcc cggtgcatga accggtgggc      1440
agcctgaccc cggcgccggt gccgcagccg ctggatccgg cgccggcggt gacccgggaa      1500
gcgagccatc tgctggaaga tccggatgaa gaaaccagcc aggcggtgaa agcgctgcgc      1560
gaaatggcgg ataccgtgat tccgcagaaa gaagaagcgg cgatttgcgg ccagatggat      1620
ctgagccatc cgccgccgcg cggccatctg gatgaactga ccaccaccct ggaaagcatg      1680
accgaagatc tgaacctgga tagcccgctg accccggaac tgaacgaaat tctggatacc      1740
tttctgaacg atgaatgcct gctgcatgcg atgcatatta gcaccggcct gagcattttt      1800
gataccagcc tgtttt                                                       1815
```

<210> SEQ ID NO 56
<211> LENGTH: 605
<212> TYPE: PRT
<213> ORGANISM: Artificial Sequence
<220> FEATURE:
<223> OTHER INFORMATION: Synthetic

<400> SEQUENCE: 56

```
Met Arg Pro Lys Lys Asp Gly Leu Glu Asp Phe Leu Arg Leu Thr Pro
1               5                   10                  15
```

```
Glu Ile Lys Lys Gln Leu Gly Ser Leu Val Ser Asp Tyr Cys Asn Val
            20                  25                  30

Leu Asn Lys Glu Phe Thr Ala Gly Ser Val Glu Ile Thr Leu Arg Ser
            35                  40                  45

Tyr Lys Ile Cys Lys Ala Phe Ile Asn Glu Ala Lys Ala His Gly Arg
        50                  55                  60

Glu Trp Gly Gly Leu Met Ala Thr Leu Asn Ile Cys Asn Phe Trp Ala
65                  70                  75                  80

Ile Leu Arg Asn Asn Arg Val Arg Arg Ala Glu Asn Ala Gly Asn
                85                  90                  95

Asp Ala Cys Ser Ile Ala Cys Pro Ile Val Met Arg Tyr Val Leu Asp
                100                 105                 110

His Leu Ile Val Val Thr Asp Arg Phe Phe Ile Gln Ala Pro Ser Asn
            115                 120                 125

Arg Val Met Ile Pro Ala Thr Ile Gly Thr Ala Met Tyr Lys Leu Leu
        130                 135                 140

Lys His Ser Arg Val Arg Ala Tyr Thr Tyr Ser Lys Val Leu Gly Val
145                 150                 155                 160

Asp Arg Ala Ala Ile Met Ala Ser Gly Lys Gln Val Val Glu His Leu
                165                 170                 175

Asn Arg Met Glu Lys Glu Gly Leu Leu Ser Ser Lys Phe Lys Ala Phe
            180                 185                 190

Cys Lys Trp Val Phe Thr Tyr Pro Val Leu Glu Glu Met Phe Gln Thr
        195                 200                 205

Met Val Ser Ser Lys Thr Gly His Leu Thr Asp Asp Val Lys Asp Val
    210                 215                 220

Arg Ala Leu Ile Lys Thr Leu Pro Arg Ala Ser Tyr Ser Ser His Ala
225                 230                 235                 240

Gly Gln Arg Ser Tyr Val Ser Gly Val Leu Pro Ala Cys Leu Leu Ser
                245                 250                 255

Thr Lys Ser Lys Ala Val Glu Thr Pro Ile Leu Val Ser Gly Ala Asp
            260                 265                 270

Arg Met Asp Glu Glu Leu Met Gly Asn Asp Gly Gly Ala Ser His Thr
            275                 280                 285

Glu Ala Arg Tyr Ser Glu Ser Gly Gln Phe His Ala Phe Thr Asp Glu
    290                 295                 300

Leu Glu Ser Leu Pro Ser Pro Thr Met Pro Leu Lys Pro Gly Ala Gln
305                 310                 315                 320

Ser Ala Asp Cys Gly Asp Ser Ser Ser Ser Ser Asp Ser Gly Asn
                325                 330                 335

Ser Asp Thr Glu Gln Ser Glu Arg Glu Glu Ala Arg Ala Glu Ala Pro
            340                 345                 350

Arg Leu Arg Ala Pro Lys Ser Arg Arg Thr Ser Arg Pro Asn Arg Gly
            355                 360                 365

Gln Thr Pro Cys Pro Ser Asn Ala Ala Glu Pro Glu Gln Pro Trp Ile
    370                 375                 380

Ala Ala Val His Gln Glu Ser Asp Glu Arg Pro Ile Phe Pro His Pro
385                 390                 395                 400

Ser Lys Pro Thr Phe Leu Pro Pro Val Lys Arg Lys Lys Gly Leu Arg
                405                 410                 415

Asp Ser Arg Glu Gly Met Phe Leu Pro Lys Pro Glu Ala Gly Ser Ala
            420                 425                 430

Ile Ser Asp Val Phe Glu Gly Arg Glu Val Cys Gln Pro Lys Arg Ile
```

-continued

```
            435              440              445

Arg Pro Phe His Pro Pro Gly Ser Pro Trp Ala Asn Arg Pro Leu Pro
    450              455              460

Ala Ser Leu Ala Pro Thr Pro Thr Gly Pro Val His Glu Pro Val Gly
465              470              475              480

Ser Leu Thr Pro Ala Pro Val Pro Gln Pro Leu Asp Pro Ala Pro Ala
             485              490              495

Val Thr Pro Glu Ala Ser His Leu Leu Glu Asp Pro Asp Glu Glu Thr
             500              505              510

Ser Gln Ala Val Lys Ala Leu Arg Glu Met Ala Asp Thr Val Ile Pro
             515              520              525

Gln Lys Glu Glu Ala Ala Ile Cys Gly Gln Met Asp Leu Ser His Pro
    530              535              540

Pro Pro Arg Gly His Leu Asp Glu Leu Thr Thr Thr Leu Glu Ser Met
545              550              555              560

Thr Glu Asp Leu Asn Leu Asp Ser Pro Leu Thr Pro Glu Leu Asn Glu
             565              570              575

Ile Leu Asp Thr Phe Leu Asn Asp Glu Cys Leu Leu His Ala Met His
             580              585              590

Ile Ser Thr Gly Leu Ser Ile Phe Asp Thr Ser Leu Phe
             595              600              605

<210> SEQ ID NO 57
<211> LENGTH: 172
<212> TYPE: PRT
<213> ORGANISM: Artificial Sequence
<220> FEATURE:
<223> OTHER INFORMATION: Synthetic

<400> SEQUENCE: 57

Arg Pro Phe Gln Cys Arg Ile Cys Met Arg Asn Phe Ser Gln Arg Gly
1               5               10               15

Asn Leu Val Arg His Ile Arg Thr His Thr Gly Glu Lys Pro Phe Ala
             20               25               30

Cys Asp Ile Cys Gly Lys Lys Phe Ala Leu Ser Phe Asn Leu Thr Arg
             35               40               45

His Thr Lys Ile His Thr Gly Ser Gln Lys Pro Phe Gln Cys Arg Ile
    50               55               60

Cys Met Arg Asn Phe Ser Arg Ser Asp Asn Leu Thr Arg His Ile Arg
65               70               75               80

Thr His Thr Gly Glu Lys Pro Phe Ala Cys Asp Ile Cys Gly Lys Lys
             85               90               95

Phe Ala Asp Arg Ser His Leu Ala Arg His Thr Lys Ile His Thr Gly
             100              105              110

Ser Gln Lys Pro Phe Gln Cys Arg Ile Cys Met Arg Asn Phe Ser Gln
             115              120              125

Lys Ala His Leu Thr Ala His Ile Arg Thr His Thr Gly Glu Lys Pro
    130              135              140

Phe Ala Cys Asp Ile Cys Gly Arg Lys Phe Ala Arg Ser Asp Asn Leu
145              150              155              160

Thr Arg His Thr Lys Ile His Leu Arg Gln Lys Asp
             165              170

<210> SEQ ID NO 58
<211> LENGTH: 516
<212> TYPE: DNA
```

-continued

```
<213> ORGANISM: Artificial Sequence
<220> FEATURE:
<223> OTHER INFORMATION: Synthetic

<400> SEQUENCE: 58
cgaccattcc agtgtcgaat ctgcatgcgc aacttcagcc agcggggaaa cctggtgagg      60
catatccgca cccacacggg agagaagcct tttgcctgcg atatttgtgg aaagaagttt     120
gctctgagct tcaatctaac cagacacacc aagattcata ctgggtccca gaaaccgttc     180
cagtgtagga tatgcatgag gaatttctct cggagtgaca acttaacgcg gcatataagg     240
acgcacacag gtgaaaaacc atttgcatgc gacatctgtg gcaaaaagtt tgcggaccgg     300
tctcaccttg cccgacacac aaaaatccat accggcagtc aaaagccctt tcaatgtcgc     360
atttgcatgc gaaacttctc acagaaggcc catttgactg cccatattcg tactcatact     420
ggcgagaaac ctttcgcttg cgatatatgt ggtcgtaagt ttgcacggtc ggacaacctc     480
acacgccaca ctaagataca cctgcggcag aaggac                               516

<210> SEQ ID NO 59
<211> LENGTH: 172
<212> TYPE: PRT
<213> ORGANISM: Artificial Sequence
<220> FEATURE:
<223> OTHER INFORMATION: Synthetic

<400> SEQUENCE: 59

Arg Pro Phe Gln Cys Arg Ile Cys Met Arg Asn Phe Ser Arg Ser Ser
1               5                   10                  15

Asn Leu Thr Arg His Ile Arg Thr His Thr Gly Glu Lys Pro Phe Ala
            20                  25                  30

Cys Asp Ile Cys Gly Lys Lys Phe Ala Asp Lys Arg Thr Leu Ile Arg
        35                  40                  45

His Thr Lys Ile His Thr Gly Ser Gln Lys Pro Phe Gln Cys Arg Ile
    50                  55                  60

Cys Met Arg Asn Phe Ser Gln Arg Gly Asn Leu Val Arg His Ile Arg
65                  70                  75                  80

Thr His Thr Gly Glu Lys Pro Phe Ala Cys Asp Ile Cys Gly Lys Lys
                85                  90                  95

Phe Ala Leu Ser Phe Asn Leu Thr Arg His Thr Lys Ile His Thr Gly
            100                 105                 110

Ser Gln Lys Pro Phe Gln Cys Arg Ile Cys Met Arg Asn Phe Ser Arg
        115                 120                 125

Ser Asp Asn Leu Thr Arg His Ile Arg Thr His Thr Gly Glu Lys Pro
    130                 135                 140

Phe Ala Cys Asp Ile Cys Gly Arg Lys Phe Ala Asp Arg Ser His Leu
145                 150                 155                 160

Ala Arg His Thr Lys Ile His Leu Arg Gln Lys Asp
                165                 170

<210> SEQ ID NO 60
<211> LENGTH: 516
<212> TYPE: DNA
<213> ORGANISM: Artificial Sequence
<220> FEATURE:
<223> OTHER INFORMATION: Synthetic

<400> SEQUENCE: 60
cgaccattcc agtgtcgaat ctgcatgcgc aacttcagcc gaagttccaa cctgacacgg      60
```

-continued

```
catatccgca cccacacggg agagaagcct tttgcctgcg atatttgtgg aaagaagttt      120
gctgacaagc ggaccttaat ccgccacacc aagattcata ctgggtccca gaaaccgttc      180
cagtgtagga tatgcatgag gaatttctct cagcggggaa atctagtgcg acatataagg      240
acgcacacag gtgaaaaacc atttgcatgc gacatctgtg gcaaaaagtt tgcgctgagc      300
ttcaacttga ctcgtcacac aaaaatccat accggcagtc aaaagccctt tcaatgtcgc      360
atttgcatgc gaaacttctc acggagtgac aatcttacga gacatattcg tactcatact      420
ggcgagaaac ctttcgcttg cgatatatgt ggtcgtaagt ttgcagaccg gagccactta      480
gccaggcaca ctaagataca cctgcggcag aaggac                                516
```

```
<210> SEQ ID NO 61
<211> LENGTH: 172
<212> TYPE: PRT
<213> ORGANISM: Artificial Sequence
<220> FEATURE:
<223> OTHER INFORMATION: Synthetic

<400> SEQUENCE: 61

Arg Pro Phe Gln Cys Arg Ile Cys Met Arg Asn Phe Ser Asp Arg Ser
1               5                   10                  15

Ala Leu Ala Arg His Ile Arg Thr His Thr Gly Glu Lys Pro Phe Ala
                20                  25                  30

Cys Asp Ile Cys Gly Lys Lys Phe Ala Arg Ser Asp Asn Leu Thr Arg
            35                  40                  45

His Thr Lys Ile His Thr Gly Ser Gln Lys Pro Phe Gln Cys Arg Ile
        50                  55                  60

Cys Met Arg Asn Phe Ser Gln Ser Gly Asp Leu Thr Arg His Ile Arg
65                  70                  75                  80

Thr His Thr Gly Glu Lys Pro Phe Ala Cys Asp Ile Cys Gly Lys Lys
                85                  90                  95

Phe Ala Val Arg Gln Thr Leu Lys Gln His Thr Lys Ile His Thr Gly
                100                 105                 110

Ser Gln Lys Pro Phe Gln Cys Arg Ile Cys Met Arg Asn Phe Ser Ala
            115                 120                 125

Ala Gly Asn Leu Thr Arg His Ile Arg Thr His Thr Gly Glu Lys Pro
        130                 135                 140

Phe Ala Cys Asp Ile Cys Gly Arg Lys Phe Ala Arg Ser Asp Asn Leu
145                 150                 155                 160

Thr Arg His Thr Lys Ile His Leu Arg Gln Lys Asp
                165                 170
```

```
<210> SEQ ID NO 62
<211> LENGTH: 516
<212> TYPE: DNA
<213> ORGANISM: Artificial Sequence
<220> FEATURE:
<223> OTHER INFORMATION: Synthetic

<400> SEQUENCE: 62
```

```
cgaccattcc agtgtcgaat ctgcatgcgc aacttcagcg accggagcgc gctggcacgg       60
catatccgca cccacacggg agagaagcct tttgcctgcg atatttgtgg aaagaagttt      120
gctcgaagtg acaacttaac gcgccacacc aagattcata ctgggtccca gaaaccgttc      180
cagtgtagga tatgcatgag gaatttctct cagtcagggg acctcactcg tcatataagg      240
acgcacacag gtgaaaaacc atttgcatgc gacatctgtg gcaaaaagtt tgcggtacga      300
```

-continued

```
cagacgctta aacaacacac aaaaatccat accggcagtc aaaagccctt tcaatgtcgc      360
atttgcatgc gaaacttctc agccgctggt aacttgacac gacatattcg tactcatact      420
ggcgagaaac ctttcgcttg cgatatatgt ggtcgtaagt ttgcaagatc tgataatcta      480
acgcgtcaca ctaagataca cctgcggcag aaggac                                516
```

```
<210> SEQ ID NO 63
<211> LENGTH: 28
<212> TYPE: PRT
<213> ORGANISM: Artificial Sequence
<220> FEATURE:
<223> OTHER INFORMATION: Synthetic

<400> SEQUENCE: 63

Phe Gln Cys Arg Ile Cys Met Arg Asn Phe Ser Gln Arg Gly Asn Leu
1               5                   10                  15

Val Arg His Ile Arg Thr His Thr Gly Glu Lys Pro
            20                  25
```

```
<210> SEQ ID NO 64
<211> LENGTH: 29
<212> TYPE: PRT
<213> ORGANISM: Artificial Sequence
<220> FEATURE:
<223> OTHER INFORMATION: Synthetic

<400> SEQUENCE: 64

Phe Ala Cys Asp Ile Cys Gly Lys Lys Phe Ala Leu Ser Phe Asn Leu
1               5                   10                  15

Thr Arg His Thr Lys Ile His Thr Gly Ser Gln Lys Pro
            20                  25
```

```
<210> SEQ ID NO 65
<211> LENGTH: 28
<212> TYPE: PRT
<213> ORGANISM: Artificial Sequence
<220> FEATURE:
<223> OTHER INFORMATION: Synthetic

<400> SEQUENCE: 65

Phe Gln Cys Arg Ile Cys Met Arg Asn Phe Ser Arg Ser Asp Asn Leu
1               5                   10                  15

Thr Arg His Ile Arg Thr His Thr Gly Glu Lys Pro
            20                  25
```

```
<210> SEQ ID NO 66
<211> LENGTH: 29
<212> TYPE: PRT
<213> ORGANISM: Artificial Sequence
<220> FEATURE:
<223> OTHER INFORMATION: Synthetic

<400> SEQUENCE: 66

Phe Ala Cys Asp Ile Cys Gly Lys Lys Phe Ala Asp Arg Ser His Leu
1               5                   10                  15

Ala Arg His Thr Lys Ile His Thr Gly Ser Gln Lys Pro
            20                  25
```

```
<210> SEQ ID NO 67
<211> LENGTH: 28
<212> TYPE: PRT
<213> ORGANISM: Artificial Sequence
<220> FEATURE:
<223> OTHER INFORMATION: Synthetic
```

-continued

<400> SEQUENCE: 67

Phe Gln Cys Arg Ile Cys Met Arg Asn Phe Ser Gln Lys Ala His Leu
1               5                   10                  15

Thr Ala His Ile Arg Thr His Thr Gly Glu Lys Pro
            20                  25

<210> SEQ ID NO 68
<211> LENGTH: 28
<212> TYPE: PRT
<213> ORGANISM: Artificial Sequence
<220> FEATURE:
<223> OTHER INFORMATION: Synthetic

<400> SEQUENCE: 68

Phe Ala Cys Asp Ile Cys Gly Arg Lys Phe Ala Arg Ser Asp Asn Leu
1               5                   10                  15

Thr Arg His Thr Lys Ile His Leu Arg Gln Lys Asp
            20                  25

<210> SEQ ID NO 69
<211> LENGTH: 28
<212> TYPE: PRT
<213> ORGANISM: Artificial Sequence
<220> FEATURE:
<223> OTHER INFORMATION: Synthetic

<400> SEQUENCE: 69

Phe Gln Cys Arg Ile Cys Met Arg Asn Phe Ser Arg Ser Ser Asn Leu
1               5                   10                  15

Thr Arg His Ile Arg Thr His Thr Gly Glu Lys Pro
            20                  25

<210> SEQ ID NO 70
<211> LENGTH: 29
<212> TYPE: PRT
<213> ORGANISM: Artificial Sequence
<220> FEATURE:
<223> OTHER INFORMATION: Synthetic

<400> SEQUENCE: 70

Phe Ala Cys Asp Ile Cys Gly Lys Lys Phe Ala Asp Lys Arg Thr Leu
1               5                   10                  15

Ile Arg His Thr Lys Ile His Thr Gly Ser Gln Lys Pro
            20                  25

<210> SEQ ID NO 71
<211> LENGTH: 28
<212> TYPE: PRT
<213> ORGANISM: Artificial Sequence
<220> FEATURE:
<223> OTHER INFORMATION: Synthetic

<400> SEQUENCE: 71

Phe Gln Cys Arg Ile Cys Met Arg Asn Phe Ser Gln Arg Gly Asn Leu
1               5                   10                  15

Val Arg His Ile Arg Thr His Thr Gly Glu Lys Pro
            20                  25

<210> SEQ ID NO 72
<211> LENGTH: 29
<212> TYPE: PRT
<213> ORGANISM: Artificial Sequence
<220> FEATURE:

<223> OTHER INFORMATION: Synthetic

<400> SEQUENCE: 72

Phe Ala Cys Asp Ile Cys Gly Lys Lys Phe Ala Leu Ser Phe Asn Leu
1               5                   10                  15

Thr Arg His Thr Lys Ile His Thr Gly Ser Gln Lys Pro
            20                  25

<210> SEQ ID NO 73
<211> LENGTH: 28
<212> TYPE: PRT
<213> ORGANISM: Artificial Sequence
<220> FEATURE:
<223> OTHER INFORMATION: Synthetic

<400> SEQUENCE: 73

Phe Gln Cys Arg Ile Cys Met Arg Asn Phe Ser Arg Ser Asp Asn Leu
1               5                   10                  15

Thr Arg His Ile Arg Thr His Thr Gly Glu Lys Pro
            20                  25

<210> SEQ ID NO 74
<211> LENGTH: 28
<212> TYPE: PRT
<213> ORGANISM: Artificial Sequence
<220> FEATURE:
<223> OTHER INFORMATION: Synthetic

<400> SEQUENCE: 74

Phe Ala Cys Asp Ile Cys Gly Arg Lys Phe Ala Asp Arg Ser His Leu
1               5                   10                  15

Ala Arg His Thr Lys Ile His Leu Arg Gln Lys Asp
            20                  25

<210> SEQ ID NO 75
<211> LENGTH: 28
<212> TYPE: PRT
<213> ORGANISM: Artificial Sequence
<220> FEATURE:
<223> OTHER INFORMATION: Synthetic

<400> SEQUENCE: 75

Phe Gln Cys Arg Ile Cys Met Arg Asn Phe Ser Asp Arg Ser Ala Leu
1               5                   10                  15

Ala Arg His Ile Arg Thr His Thr Gly Glu Lys Pro
            20                  25

<210> SEQ ID NO 76
<211> LENGTH: 29
<212> TYPE: PRT
<213> ORGANISM: Artificial Sequence
<220> FEATURE:
<223> OTHER INFORMATION: Synthetic

<400> SEQUENCE: 76

Phe Ala Cys Asp Ile Cys Gly Lys Lys Phe Ala Arg Ser Asp Asn Leu
1               5                   10                  15

Thr Arg His Thr Lys Ile His Thr Gly Ser Gln Lys Pro
            20                  25

<210> SEQ ID NO 77
<211> LENGTH: 28
<212> TYPE: PRT
<213> ORGANISM: Artificial Sequence

```
<220> FEATURE:
<223> OTHER INFORMATION: Synthetic

<400> SEQUENCE: 77

Phe Gln Cys Arg Ile Cys Met Arg Asn Phe Ser Gln Ser Gly Asp Leu
1               5                   10                  15

Thr Arg His Ile Arg Thr His Thr Gly Glu Lys Pro
            20                  25

<210> SEQ ID NO 78
<211> LENGTH: 29
<212> TYPE: PRT
<213> ORGANISM: Artificial Sequence
<220> FEATURE:
<223> OTHER INFORMATION: Synthetic

<400> SEQUENCE: 78

Phe Ala Cys Asp Ile Cys Gly Lys Lys Phe Ala Val Arg Gln Thr Leu
1               5                   10                  15

Lys Gln His Thr Lys Ile His Thr Gly Ser Gln Lys Pro
            20                  25

<210> SEQ ID NO 79
<211> LENGTH: 28
<212> TYPE: PRT
<213> ORGANISM: Artificial Sequence
<220> FEATURE:
<223> OTHER INFORMATION: Synthetic

<400> SEQUENCE: 79

Phe Gln Cys Arg Ile Cys Met Arg Asn Phe Ser Ala Ala Gly Asn Leu
1               5                   10                  15

Thr Arg His Ile Arg Thr His Thr Gly Glu Lys Pro
            20                  25

<210> SEQ ID NO 80
<211> LENGTH: 28
<212> TYPE: PRT
<213> ORGANISM: Artificial Sequence
<220> FEATURE:
<223> OTHER INFORMATION: Synthetic

<400> SEQUENCE: 80

Phe Ala Cys Asp Ile Cys Gly Arg Lys Phe Ala Arg Ser Asp Asn Leu
1               5                   10                  15

Thr Arg His Thr Lys Ile His Leu Arg Gln Lys Asp
            20                  25

<210> SEQ ID NO 81
<211> LENGTH: 4104
<212> TYPE: DNA
<213> ORGANISM: Artificial Sequence
<220> FEATURE:
<223> OTHER INFORMATION: Synthetic

<400> SEQUENCE: 81
atggacaaga agtactccat tgggctcgct atcggtacca acagcgtcgg ctgggccgtc      60
attacggacg agtacaaggt gccgagcaaa aaattcaaag ttctgggcaa taccgatcgc     120
cacagcataa agaagaacct cattggagcc ctcctgttcg actccgggga gacggccgaa     180
gccacgcggc tcaaaagaac agcacggcgc agatataccc gcagaaagaa tcggatctgc     240
tacctgcagg agatctttag taatgagatg gctaaggtgg atgactcttt cttccatagg     300
```

```
ctggaggagt cctttttggt ggaggaggat aaaaagcacg agcgccaccc aatctttggc      360
aatatcgtgg acgaggtggc gtaccatgaa aagtacccaa ccatatatca tctgaggaag      420
aagctggtag acagtactga taaggctgac ttgcggttga tctatctcgc gctggcgcac      480
atgatcaaat ttcggggaca cttcctcatc gagggggacc tgaacccaga caacagcgat      540
gtcgacaaac tctttatcca actggttcag acttacaatc agcttttcga ggagaacccg      600
atcaacgcat ccggcgttga cgccaaagca atcctgagcg ctaggctgtc caaatcccgg      660
cggctcgaaa acctcatcgc acagctccct ggggagaaga agaacggcct gtttggtaat      720
cttatcgccc tgtcactcgg gctgaccccc aactttaaat ctaacttcga cctggccgaa      780
gatgccaagc tgcaactgag caaagacacc tacgatgatg atctcgacaa tctgctggcc      840
cagatcggcg accagtacgc agaccttttt ttggcggcaa agaacctgtc agacgccatt      900
ctgctgagtg atattctgcg agtgaacacg gagatcacca aagctccgct gagcgctagt      960
atgatcaagc gctatgatga gcaccaccaa gacttgactt tgctgaaggc ccttgtcaga     1020
cagcaactgc ctgagaagta caaggaaatt ttcttcgatc agtctaaaaa tggctacgcc     1080
ggatacattg acggcggagc aagccaggag gaattttaca aatttattaa gcccatcttg     1140
gaaaaaatgg acggcaccga ggagctgctg gtaaagctga acagagaaga tctgttgcgc     1200
aaacagcgca cttttcgacaa tggaagcatc ccccaccaga ttcacctggg cgaactgcac     1260
gctatcctca ggcggcaaga ggatttctac ccctttttga aagataacag ggaaaagatt     1320
gagaaaatcc tcacatttcg gataccctac tatgtaggcc ccctcgctcg gggaaattcc     1380
agattcgcgt ggatgactcg caaatcagaa gagaccatca ctccctggaa cttcgaggaa     1440
gtcgtggata aggggcctc tgcccagtcc ttcatcgaaa ggatgactaa ctttgataaa     1500
aatctgccta cgaaaaggt gcttcctaaa cactctctgc tgtacgagta cttcacagtt     1560
tataacgagc tcaccaaggt caaatacgtc acagaaggga tgagaaagcc agcattcctg     1620
tctggagagc agaagaaagc tatcgtggac ctcctcttca agacgaaccg gaaagttacc     1680
gtgaaacagc tcaaagaaga ctatttcaaa aagattgaat gtttcgactc tgttgaaatc     1740
agcggagtgg aggatcgctt caacgcatcc ctgggaacgt atcacgatct cctgaaaatc     1800
attaaagaca aggacttcct ggacaatgag gagaacgagg acattcttga ggacattgtc     1860 ctcacccta cgttgtttga agatagggag atgattgaag aacgcttgaa aacttacgct     1920
catctcttcg acgacaaagt catgaaacag ctcaagagac gccgatatac aggatggggg     1980
cggctgtcaa gaaaactgat caatggcatc cgagacaagc agagtggaaa gacaatcctg     2040
gattttctta agtccgatgg atttgccaac cggaacttca tgcagttgat ccatgatgac     2100
tctctcacct ttaaggagga catccagaaa gcacaagttt ctggccaggg ggacagtctt     2160
cacgagcaca tcgctaatct tgcaggtagc ccagctatca aaaagggaat actgcagacc     2220
gttaaggtcg tggatgaact cgtcaaagta atgggaaggc ataagcccga gaatatcgtt     2280
atcgagatgg cccgagagaa ccaaactacc cagaagggac agaagaacag tagggaaagg     2340
atgaagagga ttgaagaggg tataaaagaa ctggggtccc aaatccttaa ggaacaccca     2400
gttgaaaaca cccagcttca gaatgagaag ctctacctgt actacctgca gaacggcagg     2460
gacatgtacg tggatcagga actggacatc aaccggttgt ccgactacga cgtggatgct     2520
atcgtgcccc aaagctttct caaagatgat tctattgata taaagtgtt gacaagatcc     2580 gataaaaata gagggaagag tgataacgtc ccctcagaag aagttgtcaa gaaaatgaaa     2640
aattattggc ggcagctgct gaacgccaaa ctgatcacac aacggaagtt cgataatctg     2700
```

-continued

```
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga aagttattac tctgaagtct    2880
aagctggtct cagatttcag aaaggacttt cagtttttata aggtgagaga gatcaacaat    2940
taccaccatg cgcatgatgc ctacctgaat gcagtggtag cactgcact tatcaaaaaa    3000 tatcccaagc tggaatctga atttgtttac ggagactata agtgtacga tgttaggaaa    3060 atgatcgcaa agtctgagca ggaaataggc aaggccaccg ctaagtactt cttttacagc    3120
aatattatga attttttcaa gaccgagatt acactggcca atggagagat cggaagcga    3180 ccacttatcg aaacaaacgg agaaacagga gaaatcgtgt gggacaaggg tagggatttc    3240
gcgacagtcc gcaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatccagct tcgagaaaaa ccccatcgac    3540
tttctcgaag cgaaaggata taaagaggtc aaaaaagacc tcatcattaa gctgcccaag    3600
tactctctct ttgagcttga aaacggccgg aaacgaatgc tcgctagtgc gggcgagctg    3660
cagaaaggta acgagctggc actgccctct aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgagttctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agac    4104
```

```
<210> SEQ ID NO 82
<211> LENGTH: 1368
<212> TYPE: PRT
<213> ORGANISM: Artificial Sequence
<220> FEATURE:
<223> OTHER INFORMATION: Synthetic

<400> SEQUENCE: 82

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110
```

```
His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
        515                 520                 525
```

-continued

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
```

```
945                950                955                960
Lys Leu Val Ser Asp Phe Arg Lys Asp Phe Gln Phe Tyr Lys Val Arg
               965                970                975

Glu Ile Asn Asn Tyr His His Ala His Asp Ala Tyr Leu Asn Ala Val
           980                985                990

Val Gly Thr Ala Leu Ile Lys Lys  Tyr Pro Lys Leu Glu  Ser Glu Phe
           995                1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350
```

```
Gly Leu  Tyr Glu Thr Arg Ile  Asp Leu Ser Gln Leu  Gly Gly Asp
    1355                1360                1365
```

```
<210> SEQ ID NO 83
<211> LENGTH: 97
<212> TYPE: DNA
<213> ORGANISM: Artificial Sequence
<220> FEATURE:
<223> OTHER INFORMATION: Synthetic

<400> SEQUENCE: 83
gaggtaccat agagtgaggc ggttttagag ctagaaatag caagttaaaa taaggctagt      60
ccgttatcaa cttgaaaaag tggcaccgag tcggtgc                               97

<210> SEQ ID NO 84
<211> LENGTH: 97
<212> TYPE: RNA
<213> ORGANISM: Artificial Sequence
<220> FEATURE:
<223> OTHER INFORMATION: Synthetic

<400> SEQUENCE: 84
gagguaccau agagugaggc gguuuuagag cuagaaauag caaguuaaaa uaaggcuagu      60
ccguuaucaa cuugaaaaag uggcaccgag ucggugc                               97

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
gaggtaccat agagtgaggc g                                                21

<210> SEQ ID NO 86
<211> LENGTH: 21
<212> TYPE: RNA
<213> ORGANISM: Artificial Sequence
<220> FEATURE:
<223> OTHER INFORMATION: Synthetic

<400> SEQUENCE: 86
gagguaccau agagugaggc g                                                21

<210> SEQ ID NO 87
<211> LENGTH: 99
<212> TYPE: DNA
<213> ORGANISM: Artificial Sequence
<220> FEATURE:
<223> OTHER INFORMATION: Synthetic

<400> SEQUENCE: 87
accgaggcga ggatgaagcc gaggttttag agctagaaat agcaagttaa aataaggcta      60
gtccgttatc aacttgaaaa agtggcaccg agtcggtgc                             99

<210> SEQ ID NO 88
<211> LENGTH: 99
<212> TYPE: RNA
<213> ORGANISM: Artificial Sequence
<220> FEATURE:
<223> OTHER INFORMATION: Synthetic

<400> SEQUENCE: 88
```

-continued

```
accgaggcga ggaugaagcc gagguuuuag agcuagaaau agcaaguuaa aauaaggcua      60
guccguuauc aacuugaaaa aguggcaccg agucggugc                              99
```

```
<210> SEQ ID NO 89
<211> LENGTH: 23
<212> TYPE: DNA
<213> ORGANISM: Artificial Sequence
<220> FEATURE:
<223> OTHER INFORMATION: Synthetic

<400> SEQUENCE: 89
accgaggcga ggatgaagcc gag                                               23
```

```
<210> SEQ ID NO 90
<211> LENGTH: 23
<212> TYPE: RNA
<213> ORGANISM: Artificial Sequence
<220> FEATURE:
<223> OTHER INFORMATION: Synthetic

<400> SEQUENCE: 90
accgaggcga ggaugaagcc gag                                               23
```

```
<210> SEQ ID NO 91
<211> LENGTH: 100
<212> TYPE: DNA
<213> ORGANISM: Artificial Sequence
<220> FEATURE:
<223> OTHER INFORMATION: Synthetic

<400> SEQUENCE: 91
accgaagccg agaggatact gcaggtttta gagctagaaa tagcaagtta aaataaggct      60
agtccgttat caacttgaaa aagtggcacc gagtcggtgc                            100
```

```
<210> SEQ ID NO 92
<211> LENGTH: 100
<212> TYPE: RNA
<213> ORGANISM: Artificial Sequence
<220> FEATURE:
<223> OTHER INFORMATION: Synthetic

<400> SEQUENCE: 92
accgaagccg agaggauacu gcagguuuua gagcuagaaa uagcaaguua aaauaaggcu      60
aguccguuau caacuugaaa aaguggcacc gagucggugc                            100
```

```
<210> SEQ ID NO 93
<211> LENGTH: 24
<212> TYPE: DNA
<213> ORGANISM: Artificial Sequence
<220> FEATURE:
<223> OTHER INFORMATION: Synthetic

<400> SEQUENCE: 93
accgaagccg agaggatact gcag                                              24
```

```
<210> SEQ ID NO 94
<211> LENGTH: 24
<212> TYPE: RNA
<213> ORGANISM: Artificial Sequence
<220> FEATURE:
<223> OTHER INFORMATION: Synthetic

<400> SEQUENCE: 94
```

-continued

```
accgaagccg agaggauacu gcag                                          24

<210> SEQ ID NO 95
<211> LENGTH: 1569
<212> TYPE: DNA
<213> ORGANISM: Artificial Sequence
<220> FEATURE:
<223> OTHER INFORMATION: Synthetic

<400> SEQUENCE: 95
gacgcattgg acgattttga tctggatatg ctgggaagtg acgccctcga tgattttgac      60
cttgacatgc ttggttcgga tgcccttgat gactttgacc tcgacatgct cggcagtgac     120
gcccttgatg atttcgacct ggacatgctg attaactcta gaagttccgg atctccgaaa     180
aagaaacgca aagttggtag ccagtacctg cccgacaccg acgaccggca ccggatcgag     240
gaaaagcgga agcggaccta cgagacattc aagagcatca tgaagaagtc ccccttcagc     300
ggccccaccg accctagacc tccacctaga agaatcgccg tgcccagcag atccagcgcc     360
agcgtgccaa aacctgcccc ccagccttac cccttcacca gcagcctgag caccatcaac     420
tacgacgagt ccctaccat ggtgttcccc agcggccaga tctctcaggc ctctgctctg     480
gctccagccc ctcctcaggt gctgcctcag gctcctgctc ctgcaccagc tccagccatg     540
gtgtctgcac tggctcaggc accagcaccc gtgcctgtgc tggctcctgg acctccacag     600
gctgtggctc accagccccc taaacctaca caggccggcg agggcacact gtctgaagct     660
ctgctgcagc tgcagttcga cgacgaggat ctgggagccc tgctgggaaa cagcaccgat     720
cctgccgtgt tcaccgacct ggccagcgtg acaacagcg agttccagca gctgctgaac     780
cagggcatcc ctgtggcccc tcacaccacc gagcccatgc tgatggaata ccccgaggcc     840
atcacccggc tcgtgacagg cgctcagagg cctcctgatc cagctcctgc ccctctggga     900
gcaccaggcc tgcctaatgg actgctgtct ggcgacgagg acttcagctc tatcgccgat     960
atggatttct cagccttgct gggctctggc agcggcagcc gggattccag ggaagggatg    1020
tttttgccga agcctgaggc cggctccgct attagtgacg tgtttgaggg ccgcgaggtg    1080
tgccagccaa aacgaatccg gccatttcat cctccaggaa gtccatgggc caaccgccca    1140 ctcccccgcca gcctcgcacc aacaccaacc ggtccagtac atgagccagt cgggtcactg    1200
accccggcac cagtccctca gccactggat ccagcgcccg cagtgactcc cgaggccagt    1260
cacctgttgg aggatcccga tgaagagacg agccaggctg tcaaagccct tcgggagatg    1320
gccgatactg tgattcccca gaaggaagag gctgcaatct gtggccaaat ggacctttcc    1380
catccgcccc caaggggcca tctggatgag ctgacaacca cacttgagtc catgaccgag    1440
gatctgaacc tggactcacc cctgaccccg gaattgaacg agattctgga taccttcctg    1500
aacgacgagt gcctcttgca tgccatgcat atcagcacag gactgtccat cttcgacaca    1560
tctctgtttt                                                          1569

<210> SEQ ID NO 96
<211> LENGTH: 523
<212> TYPE: PRT
<213> ORGANISM: Artificial Sequence
<220> FEATURE:
<223> OTHER INFORMATION: Synthetic

<400> SEQUENCE: 96

Asp Ala Leu Asp Asp Phe Asp Leu Asp Met Leu Gly Ser Asp Ala Leu
1               5                   10                  15
```

-continued

```
Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
            35                  40                  45

Met Leu Ile Asn Ser Arg Ser Ser Gly Ser Pro Lys Lys Arg Lys
    50                  55                  60

Val Gly Ser Gln Tyr Leu Pro Asp Thr Asp Asp Arg His Arg Ile Glu
65                  70                  75                  80

Glu Lys Arg Lys Arg Thr Tyr Glu Thr Phe Lys Ser Ile Met Lys Lys
                85                  90                  95

Ser Pro Phe Ser Gly Pro Thr Asp Pro Arg Pro Pro Arg Arg Ile
            100                 105                 110

Ala Val Pro Ser Arg Ser Ser Ala Ser Val Pro Lys Pro Ala Pro Gln
            115                 120                 125

Pro Tyr Pro Phe Thr Ser Ser Leu Ser Thr Ile Asn Tyr Asp Glu Phe
    130                 135                 140

Pro Thr Met Val Phe Pro Ser Gly Gln Ile Ser Gln Ala Ser Ala Leu
145                 150                 155                 160

Ala Pro Ala Pro Pro Gln Val Leu Pro Gln Ala Pro Ala Pro Ala Pro
            165                 170                 175

Ala Pro Ala Met Val Ser Ala Leu Ala Gln Ala Pro Ala Pro Val Pro
            180                 185                 190

Val Leu Ala Pro Gly Pro Pro Gln Ala Val Ala Pro Pro Ala Pro Lys
            195                 200                 205

Pro Thr Gln Ala Gly Glu Gly Thr Leu Ser Glu Ala Leu Leu Gln Leu
    210                 215                 220

Gln Phe Asp Asp Glu Asp Leu Gly Ala Leu Leu Gly Asn Ser Thr Asp
225                 230                 235                 240

Pro Ala Val Phe Thr Asp Leu Ala Ser Val Asp Asn Ser Glu Phe Gln
            245                 250                 255

Gln Leu Leu Asn Gln Gly Ile Pro Val Ala Pro His Thr Thr Glu Pro
            260                 265                 270

Met Leu Met Glu Tyr Pro Glu Ala Ile Thr Arg Leu Val Thr Gly Ala
            275                 280                 285

Gln Arg Pro Pro Asp Pro Ala Pro Ala Pro Leu Gly Ala Pro Gly Leu
    290                 295                 300

Pro Asn Gly Leu Leu Ser Gly Asp Glu Asp Phe Ser Ser Ile Ala Asp
305                 310                 315                 320

Met Asp Phe Ser Ala Leu Leu Gly Ser Gly Ser Gly Ser Arg Asp Ser
            325                 330                 335

Arg Glu Gly Met Phe Leu Pro Lys Pro Glu Ala Gly Ser Ala Ile Ser
            340                 345                 350

Asp Val Phe Glu Gly Arg Glu Val Cys Gln Pro Lys Arg Ile Arg Pro
            355                 360                 365

Phe His Pro Pro Gly Ser Pro Trp Ala Asn Arg Pro Leu Pro Ala Ser
    370                 375                 380

Leu Ala Pro Thr Pro Thr Gly Pro Val His Glu Pro Val Gly Ser Leu
385                 390                 395                 400

Thr Pro Ala Pro Val Pro Gln Pro Leu Asp Pro Ala Pro Ala Val Thr
            405                 410                 415

Pro Glu Ala Ser His Leu Leu Glu Asp Pro Asp Glu Glu Thr Ser Gln
            420                 425                 430

Ala Val Lys Ala Leu Arg Glu Met Ala Asp Thr Val Ile Pro Gln Lys
```

```
              435                    440                    445
Glu Glu Ala Ala Ile Cys Gly Gln Met Asp Leu Ser His Pro Pro Pro
    450                    455                    460

Arg Gly His Leu Asp Glu Leu Thr Thr Thr Leu Glu Ser Met Thr Glu
465                    470                    475                    480

Asp Leu Asn Leu Asp Ser Pro Leu Thr Pro Glu Leu Asn Glu Ile Leu
                    485                    490                    495

Asp Thr Phe Leu Asn Asp Glu Cys Leu Leu His Ala Met His Ile Ser
                500                    505                    510

Thr Gly Leu Ser Ile Phe Asp Thr Ser Leu Phe
            515                    520
```

<210> SEQ ID NO 97
<211> LENGTH: 1939
<212> TYPE: PRT
<213> ORGANISM: Artificial Sequence
<220> FEATURE:
<223> OTHER INFORMATION: Synthetic

<400> SEQUENCE: 97

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
```

-continued

```
              275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
    690                 695                 700
```

-continued

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110
```

```
Arg Asn Ser Asp Lys Leu Ile  Ala Arg Lys Lys Asp  Trp Asp Pro
    1115            1120                 1125

Lys Lys Tyr Gly Gly Phe Asp  Ser Pro Thr Val Ala  Tyr Ser Val
    1130            1135                 1140

Leu Val Val Ala Lys Val Glu  Lys Gly Lys Ser Lys  Lys Leu Lys
    1145            1150                 1155

Ser Val Lys Glu Leu Leu Gly  Ile Thr Ile Met Glu  Arg Ser Ser
    1160            1165                 1170

Phe Glu Lys Asn Pro Ile Asp  Phe Leu Glu Ala Lys  Gly Tyr Lys
    1175            1180                 1185

Glu Val Lys Lys Asp Leu Ile  Ile Lys Leu Pro Lys  Tyr Ser Leu
    1190            1195                 1200

Phe Glu Leu Glu Asn Gly Arg  Lys Arg Met Leu Ala  Ser Ala Gly
    1205            1210                 1215

Glu Leu Gln Lys Gly Asn Glu  Leu Ala Leu Pro Ser  Lys Tyr Val
    1220            1225                 1230

Asn Phe Leu Tyr Leu Ala Ser  His Tyr Glu Lys Leu  Lys Gly Ser
    1235            1240                 1245

Pro Glu Asp Asn Glu Gln Lys  Gln Leu Phe Val Glu  Gln His Lys
    1250            1255                 1260

His Tyr Leu Asp Glu Ile Ile  Glu Gln Ile Ser Glu  Phe Ser Lys
    1265            1270                 1275

Arg Val Ile Leu Ala Asp Ala  Asn Leu Asp Lys Val  Leu Ser Ala
    1280            1285                 1290

Tyr Asn Lys His Arg Asp Lys  Pro Ile Arg Glu Gln  Ala Glu Asn
    1295            1300                 1305

Ile Ile His Leu Phe Thr Leu  Thr Asn Leu Gly Ala  Pro Ala Ala
    1310            1315                 1320

Phe Lys Tyr Phe Asp Thr Thr  Ile Asp Arg Lys Arg  Tyr Thr Ser
    1325            1330                 1335

Thr Lys Glu Val Leu Asp Ala  Thr Leu Ile His Gln  Ser Ile Thr
    1340            1345                 1350

Gly Leu Tyr Glu Thr Arg Ile  Asp Leu Ser Gln Leu  Gly Gly Asp
    1355            1360                 1365

Gly Thr Gly Gly Pro Pro Lys  Lys Lys Arg Lys Val  Ala Ala Ala
    1370            1375                 1380

Ser Arg Tyr Pro Arg Gly Asp  Ala Leu Asp Asp Phe  Asp Leu Asp
    1385            1390                 1395

Met Leu Gly Ser Asp Ala Leu  Asp Asp Phe Asp Leu  Asp Met Leu
    1400            1405                 1410

Gly Ser Asp Ala Leu Asp Asp  Phe Asp Leu Asp Met  Leu Gly Ser
    1415            1420                 1425

Asp Ala Leu Asp Asp Phe Asp  Leu Asp Met Leu Ile  Asn Ser Arg
    1430            1435                 1440

Ser Ser Gly Ser Pro Lys Lys  Lys Arg Lys Val Gly  Ser Gln Tyr
    1445            1450                 1455

Leu Pro Asp Thr Asp Asp Arg  His Arg Ile Glu Glu  Lys Arg Lys
    1460            1465                 1470

Arg Thr Tyr Glu Thr Phe Lys  Ser Ile Met Lys Lys  Ser Pro Phe
    1475            1480                 1485

Ser Gly Pro Thr Asp Pro Arg  Pro Pro Pro Arg Arg  Ile Ala Val
    1490            1495                 1500

Pro Ser Arg Ser Ser Ala Ser  Val Pro Lys Pro Ala  Pro Gln Pro
```

-continued

```
        1505              1510              1515

Tyr Pro  Phe Thr Ser Ser Leu  Ser Thr Ile Asn Tyr  Asp Glu Phe
    1520              1525              1530

Pro Thr  Met Val Phe Pro Ser  Gly Gln Ile Ser Gln  Ala Ser Ala
    1535              1540              1545

Leu Ala  Pro Ala Pro Pro Gln  Val Leu Pro Gln Ala  Pro Ala Pro
    1550              1555              1560

Ala Pro  Ala Pro Ala Met Val  Ser Ala Leu Ala Gln  Ala Pro Ala
    1565              1570              1575

Pro Val  Pro Val Leu Ala Pro  Gly Pro Pro Gln Ala  Val Ala Pro
    1580              1585              1590

Pro Ala  Pro Lys Pro Thr Gln  Ala Gly Glu Gly Thr  Leu Ser Glu
    1595              1600              1605

Ala Leu  Leu Gln Leu Gln Phe  Asp Asp Glu Asp Leu  Gly Ala Leu
    1610              1615              1620

Leu Gly  Asn Ser Thr Asp Pro  Ala Val Phe Thr Asp  Leu Ala Ser
    1625              1630              1635

Val Asp  Asn Ser Glu Phe Gln  Gln Leu Leu Asn Gln  Gly Ile Pro
    1640              1645              1650

Val Ala  Pro His Thr Thr Glu  Pro Met Leu Met Glu  Tyr Pro Glu
    1655              1660              1665

Ala Ile  Thr Arg Leu Val Thr  Gly Ala Gln Arg Pro  Pro Asp Pro
    1670              1675              1680

Ala Pro  Ala Pro Leu Gly Ala  Pro Gly Leu Pro Asn  Gly Leu Leu
    1685              1690              1695

Ser Gly  Asp Glu Asp Phe Ser  Ser Ile Ala Asp Met  Asp Phe Ser
    1700              1705              1710

Ala Leu  Leu Gly Ser Gly Ser  Gly Ser Arg Asp Ser  Arg Glu Gly
    1715              1720              1725

Met Phe  Leu Pro Lys Pro Glu  Ala Gly Ser Ala Ile  Ser Asp Val
    1730              1735              1740

Phe Glu  Gly Arg Glu Val Cys  Gln Pro Lys Arg Ile  Arg Pro Phe
    1745              1750              1755

His Pro  Pro Gly Ser Pro Trp  Ala Asn Arg Pro Leu  Pro Ala Ser
    1760              1765              1770

Leu Ala  Pro Thr Pro Thr Gly  Pro Val His Glu Pro  Val Gly Ser
    1775              1780              1785

Leu Thr  Pro Ala Pro Val Pro  Gln Pro Leu Asp Pro  Ala Pro Ala
    1790              1795              1800

Val Thr  Pro Glu Ala Ser His  Leu Leu Glu Asp Pro  Asp Glu Glu
    1805              1810              1815

Thr Ser  Gln Ala Val Lys Ala  Leu Arg Glu Met Ala  Asp Thr Val
    1820              1825              1830

Ile Pro  Gln Lys Glu Glu Ala  Ala Ile Cys Gly Gln  Met Asp Leu
    1835              1840              1845

Ser His  Pro Pro Pro Arg Gly  His Leu Asp Glu Leu  Thr Thr Thr
    1850              1855              1860

Leu Glu  Ser Met Thr Glu Asp  Leu Asn Leu Asp Ser  Pro Leu Thr
    1865              1870              1875

Pro Glu  Leu Asn Glu Ile Leu  Asp Thr Phe Leu Asn  Asp Glu Cys
    1880              1885              1890

Leu Leu  His Ala Met His Ile  Ser Thr Gly Leu Ser  Ile Phe Asp
    1895              1900              1905
```

-continued

Thr Ser  Leu Phe Pro Lys Lys  Lys Arg Lys Val Arg  Ser Lys Arg
    1910                  1915             1920

Pro Ala  Ala Thr Lys Lys Ala  Gly Gln Ala Lys Lys  Lys Lys Leu
    1925                  1930             1935

Asp

<210> SEQ ID NO 98
<211> LENGTH: 112
<212> TYPE: DNA
<213> ORGANISM: Artificial Sequence
<220> FEATURE:
<223> OTHER INFORMATION: Synthetic

<400> SEQUENCE: 98
gaaacaagct atttgctgat ttgtattagg taccatagag tgaggcgagg atgaagccga     60
gaggatactg cagaggtctc tggtgcaatg tgtgtatgtg tgcgtttgtg tg            112

<210> SEQ ID NO 99
<211> LENGTH: 71
<212> TYPE: DNA
<213> ORGANISM: Artificial Sequence
<220> FEATURE:
<223> OTHER INFORMATION: Synthetic

<400> SEQUENCE: 99
gaaacaagct atttgctgat ttgtattagg taccatagag tgaggcgagg atgaagccga     60
gaggatactg c                                                          71

<210> SEQ ID NO 100
<211> LENGTH: 112
<212> TYPE: DNA
<213> ORGANISM: Artificial Sequence
<220> FEATURE:
<223> OTHER INFORMATION: Synthetic

<400> SEQUENCE: 100
gaaacaagct atttgctgat ttgtattagg taccatagag tgaggcgagg atgaagccga     60
gaggatactg cagaggtctc tggtgcaatg tgtgtatgtg tgcgtttgtg tg            112

<210> SEQ ID NO 101
<211> LENGTH: 108
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t

<400> SEQUENCE: 101
gaaacaagct atttgctgat ttgtattagg taccatagag tgaggcgagg angaagccga     60
gaggatactg cagaggtctc tggtgcaatg tgtgtatgtg tgcgtttg               108

<210> SEQ ID NO 102
<211> LENGTH: 84
<212> TYPE: DNA
<213> ORGANISM: Artificial Sequence
<220> FEATURE:
<223> OTHER INFORMATION: Synthetic

<400> SEQUENCE: 102

-continued

```
ttccagtgtc gaatctgcat gcgcaacttc agccagcggg gaaacctggt gaggcatatc        60
cgcacccaca cgggagagaa gcct                                               84

<210> SEQ ID NO 103
<211> LENGTH: 87
<212> TYPE: DNA
<213> ORGANISM: Artificial Sequence
<220> FEATURE:
<223> OTHER INFORMATION: Synthetic

<400> SEQUENCE: 103
tttgcctgcg atatttgtgg aaagaagttt gctctgagct tcaatctaac cagacacacc        60
aagattcata ctgggtccca gaaaccg                                            87

<210> SEQ ID NO 104
<211> LENGTH: 85
<212> TYPE: DNA
<213> ORGANISM: Artificial Sequence
<220> FEATURE:
<223> OTHER INFORMATION: Synthetic

<400> SEQUENCE: 104
ttccagtgta ggatatgcat gaggaatttc tctcggagtg acaacttaac gcggcatata        60
aggacgcaca caggtgaaaa aacaa                                              85

<210> SEQ ID NO 105
<211> LENGTH: 87
<212> TYPE: DNA
<213> ORGANISM: Artificial Sequence
<220> FEATURE:
<223> OTHER INFORMATION: Synthetic

<400> SEQUENCE: 105
tttgcatgcg acatctgtgg caaaaagttt gcggaccggt ctcaccttgc ccgacacaca        60
aaaatccata ccggcagtca aaagccc                                            87

<210> SEQ ID NO 106
<211> LENGTH: 84
<212> TYPE: DNA
<213> ORGANISM: Artificial Sequence
<220> FEATURE:
<223> OTHER INFORMATION: Synthetic

<400> SEQUENCE: 106
tttcaatgtc gcatttgcat gcgaaacttc tcacagaagg cccatttgac tgcccatatt        60
cgtactcata ctggcgagaa acct                                               84

<210> SEQ ID NO 107
<211> LENGTH: 84
<212> TYPE: DNA
<213> ORGANISM: Artificial Sequence
<220> FEATURE:
<223> OTHER INFORMATION: Synthetic

<400> SEQUENCE: 107
ttcgcttgcg atatatgtgg tcgtaagttt gcacggtcgg acaacctcac acgccacact        60
aagatacacc tgcggcagaa ggac                                               84

<210> SEQ ID NO 108
<211> LENGTH: 85
<212> TYPE: DNA
<213> ORGANISM: Artificial Sequence
```

-continued

```
<220> FEATURE:
<223> OTHER INFORMATION: Synthetic

<400> SEQUENCE: 108
ttccagtgtc gaatctgcat gcgcaacttc agcccgaatg tccaacctga cacggcatat      60
ccgcacccac acgggagaga agcct                                            85

<210> SEQ ID NO 109
<211> LENGTH: 87
<212> TYPE: DNA
<213> ORGANISM: Artificial Sequence
<220> FEATURE:
<223> OTHER INFORMATION: Synthetic

<400> SEQUENCE: 109
tttgcctgcg atatttgtgg aaagaagttt gctgacaagc ggaccttaat ccgccacacc      60
aagattcata ctgggtccca gaaaccg                                          87

<210> SEQ ID NO 110
<211> LENGTH: 84
<212> TYPE: DNA
<213> ORGANISM: Artificial Sequence
<220> FEATURE:
<223> OTHER INFORMATION: Synthetic

<400> SEQUENCE: 110
ttccagtgta ggatatgcat gaggaatttc tctcagcggg gaaatctagt gcgacatata      60
aggacgcaca caggtgaaaa acca                                             84

<210> SEQ ID NO 111
<211> LENGTH: 87
<212> TYPE: DNA
<213> ORGANISM: Artificial Sequence
<220> FEATURE:
<223> OTHER INFORMATION: Synthetic

<400> SEQUENCE: 111
tttgcatgcg acatctgtgg caaaaagttt gcgctgagct tcaacttgac tcgtcacaca      60
aaaatccata ccggcagtca aaagccc                                          87

<210> SEQ ID NO 112
<211> LENGTH: 84
<212> TYPE: DNA
<213> ORGANISM: Artificial Sequence
<220> FEATURE:
<223> OTHER INFORMATION: Synthetic

<400> SEQUENCE: 112
tttcaatgtc gcatttgcat gcgaaacttc tcacggagtg acaatcttac gagacatatt      60
cgtactcata ctggcgagaa acct                                             84

<210> SEQ ID NO 113
<211> LENGTH: 84
<212> TYPE: DNA
<213> ORGANISM: Artificial Sequence
<220> FEATURE:
<223> OTHER INFORMATION: Synthetic

<400> SEQUENCE: 113
ttcgcttgcg atatatgtgg tcgtaagttt gcagaccgga gccacttagc caggcacact      60
aagatacacc tgcggcagaa ggac                                             84
```

-continued

```
<210> SEQ ID NO 114
<211> LENGTH: 84
<212> TYPE: DNA
<213> ORGANISM: Artificial Sequence
<220> FEATURE:
<223> OTHER INFORMATION: Synthetic

<400> SEQUENCE: 114
ttccagtgtc gaatctgcat gcgcaacttc agcgaccgga gcgcgctggc acggcatatc      60
cgcacccaca cgggagagaa gcct                                             84

<210> SEQ ID NO 115
<211> LENGTH: 87
<212> TYPE: DNA
<213> ORGANISM: Artificial Sequence
<220> FEATURE:
<223> OTHER INFORMATION: Synthetic

<400> SEQUENCE: 115
tttgcctgcg atatttgtgg aaagaagttt gctcgaagtg acaacttaac gcgccacacc      60
aagattcata ctgggtccca gaaaccg                                          87

<210> SEQ ID NO 116
<211> LENGTH: 84
<212> TYPE: DNA
<213> ORGANISM: Artificial Sequence
<220> FEATURE:
<223> OTHER INFORMATION: Synthetic

<400> SEQUENCE: 116
ttccagtgta ggatatgcat gaggaatttc tctcagtcag gggacctcac tcgtcatata      60
aggacgcaca caggtgaaaa acca                                             84

<210> SEQ ID NO 117
<211> LENGTH: 87
<212> TYPE: DNA
<213> ORGANISM: Artificial Sequence
<220> FEATURE:
<223> OTHER INFORMATION: Synthetic

<400> SEQUENCE: 117
tttgcatgcg acatctgtgg caaaaagttt gcggtacgac agacgcttaa acaacacaca      60
aaaatccata ccggcagtca aaagccc                                          87

<210> SEQ ID NO 118
<211> LENGTH: 84
<212> TYPE: DNA
<213> ORGANISM: Artificial Sequence
<220> FEATURE:
<223> OTHER INFORMATION: Synthetic

<400> SEQUENCE: 118
tttcaatgtc gcatttgcat gcgaaacttc tcagccgctg gtaacttgac acgacatatt      60
cgtactcata ctggcgagaa acct                                             84

<210> SEQ ID NO 119
<211> LENGTH: 84
<212> TYPE: DNA
<213> ORGANISM: Artificial Sequence
<220> FEATURE:
<223> OTHER INFORMATION: Synthetic

<400> SEQUENCE: 119
```

143                                                                     144

-continued

```
ttcgcttgcg atatatgtgg tcgtaagttt gcaagatctg ataatctaac gcgtcacact       60
aagatacacc tgcggcagaa ggac                                              84

<210> SEQ ID NO 120
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 120

Thr Gly Glu Lys Pro
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 121

Thr Gly Ser Gln Lys Pro
1               5
```

DNA-BINDING DOMAIN TRANSACTIVATORS AND USES THEREOF

RELATED APPLICATION

This application is a national stage filing under 35 U.S.C. § 371 of international application PCT/US2020/019546, filed Feb. 24, 2020, which claims priority under 35 U.S.C. § 119(e) to U.S. provisional patent application Ser. No. 62/810,005, filed Feb. 25, 2019, the entire contents of each of which are incorporated herein by reference.

REFERENCE TO AN ELECTRONIC SEQUENCE LISTING

The contents of the electronic sequence listing (U012070106US01-SEQ-KZM.txt; Size: 127,996 bytes; and Date of Creation: Aug. 24, 2021) is herein incorporated by reference in its entirety.

BACKGROUND

The regulation of target gene expression has emerged as a major area of biomedical research. Upregulation of gene expression can correct haploinsufficient conditions resulting from decreased gene expression. Haploinsufficiency typically results when one or more loss of function mutations are present in at least one copy of a gene. AAV-based approaches of gene augmentation for treatment of diseases associated with haploinsufficiency are hampered by the packaging capacity of traditional rAAV vectors.

SUMMARY

Aspects of the disclosure relate to isolated nucleic acids and recombinant AAV vectors for gene delivery. The disclosure is based, in part, on compositions (e.g., rAAV vectors and rAAVs) and methods for regulating the expression of target genes, wherein the target gene is haploinsufficient, such as SCN1A. In some embodiments, the disclosure provides fusion proteins comprising a DNA binding domain, such as a Cys2-His2 Zinc Finger protein (ZFP), and a transcriptional regulator domain. In some embodiments, compositions described by the disclosure comprise a fusion protein comprising a DNA binding domain (e.g., a ZFP, a Transcriptional activator-like effector (TALE) domain, etc.) fused to a transcriptional regulator domain. In some embodiments, fusion proteins described by the disclosure increase the expression of a target gene (e.g., SCN1A), and are therefore useful for treating diseases characterized by deficient expression of the target gene (e.g., diseases associated with haploinsufficiency of a target gene) in a cell or subject as compared to a normal cell or subject.

Accordingly, in some aspects, the disclosure provides an isolated nucleic acid comprising a transgene configured to express at least one DNA binding domain fused to at least one transcriptional regulator domain, wherein the DNA binding domain binds to a target gene or a regulatory region (e.g., an enhancer sequence, a promoter sequence, a repressor sequence, etc.) of a target gene (e.g. in a subject or a cell), wherein the target gene encodes a voltage-gated sodium channel (e.g., Na$_v$1.1). In some embodiments, a target gene is a SCN1A gene. In some embodiments, a transgene is flanked by adeno-associated virus (AAV) inverted terminal repeats (ITRs). In some embodiments, the at least one DNA binding domain binds to a target gene (e.g., in a subject or a cell) and the transcriptional regulator domain modifies, e.g., upregulates, the expression of a target gene.

In some aspects, the disclosure provides a recombinant AAV (rAAV) comprising: a nucleic acid comprising a transgene encoding at least one DNA binding domain fused to at least one transcriptional regulator domain, wherein the DNA binding domain binds to a target gene or a regulatory region of a target gene (e.g. in a subject or a cell), wherein the target gene encodes a voltage-gated sodium channel (e.g., Nav1.1) and at least one capsid protein. In some embodiments, a target gene is a SCN1A gene. In some embodiments, a transgene is flanked by AAV inverted terminal repeats (ITRs).

In some embodiments, at least one DNA binding domain binds to a target gene (e.g., in a subject or a cell) and the transcriptional regulator domain modifies, e.g., upregulates, the expression of a target gene in the subject.

In some embodiments, at least one DNA binding domain binds to an untranslated region of a target gene. In some embodiments, a DNA binding domain binds to a regulatory region of the target gene, optionally an enhancer sequence, a promoter sequence, and/or a repressor sequence.

In some embodiments, a DNA binding domain binds between 2 and 2000 bp upstream or 2 and 2000 bp upstream or downstream of a regulatory region (e.g., an enhancer sequence, a promoter sequence, a repressor sequence, etc.) of a target gene.

In some embodiments, at least one DNA binding domain encodes a zinc finger protein (ZFP), a transcription-activator like effector (TALE), a dCas protein (e.g., dCas9 or dCas12a), and/or a homeodomain. In some embodiments, at least one DNA binding domain binds to a nucleic acid sequence set forth in any one of SEQ ID NOs: 5-7. In some embodiments, the at least one DNA binding domain is a zinc finger protein comprising a recognition helix encoded by a nucleic acid having a sequence set forth in any one of SEQ ID NOs: 11-16, 23-28, or 35-40. In some embodiments, at least one DNA binding domain is a zinc finger protein comprising an amino acid sequence set forth in any one of SEQ ID NOs: 17-22, 29-34, or 41-46.

In some embodiments, the at least one DNA binding domain is a zinc finger protein comprising a recognition helix encoded by a nucleic acid comprising SEQ ID NO: 11, a recognition helix encoded by a nucleic acid comprising SEQ ID NO: 12, a recognition helix encoded by a nucleic acid comprising SEQ ID NO: 13, a recognition helix encoded by a nucleic acid comprising SEQ ID NO: 14, a recognition helix encoded by a nucleic acid comprising SEQ ID NO: 15, and/or a recognition helix encoded by a nucleic acid comprising SEQ ID NO: 16. In some embodiments, the at least one DNA binding domain is a zinc finger protein comprising an amino acid sequence of SEQ ID NO: 57. In some embodiments, a ZFP that binds to a SCN1A gene comprises at least 60%, at least 65%, at least 70%, at least 75%, at least 80%, at least 85%, at least 90%, at least 95%, at least 97%, or at least 99% sequence identity to the amino acid sequence of SEQ ID NO: 57.

In some embodiments, the at least one DNA binding domain is a zinc finger protein comprising a recognition helix encoded by a nucleic acid comprising SEQ ID NO: 23, a recognition helix encoded by a nucleic acid comprising SEQ ID NO: 24, a recognition helix encoded by a nucleic acid comprising SEQ ID NO: 25, a recognition helix encoded by a nucleic acid comprising SEQ ID NO: 26, a recognition helix encoded by a nucleic acid comprising SEQ ID NO: 27, and/or a recognition helix encoded by a nucleic acid comprising SEQ ID NO: 28. In some embodiments, the at least one DNA binding domain is a zinc finger protein comprising an amino acid sequence of SEQ ID NO: 59. In some embodiments, a ZFP that binds to a SCN1A gene comprises at least 60%, at least 65%, at least 70%, at least 75%, at least 80%, at least 85%, at least 90%, at least 95%, at least 97%, or at least 99% sequence identity to the amino acid sequence of SEQ ID NO: 59.

In some embodiments, the at least one DNA binding domain is a zinc finger protein comprising a recognition helix encoded by a nucleic acid comprising SEQ ID NO: 35, a recognition helix encoded by a nucleic acid comprising SEQ ID NO: 36, a recognition helix encoded by a nucleic acid comprising SEQ ID NO: 37, a recognition helix encoded by a nucleic acid comprising SEQ ID NO: 38, a recognition helix encoded by a nucleic acid comprising SEQ ID NO: 39, and/or a recognition helix encoded by a nucleic acid comprising SEQ ID NO: 40. In some embodiments, the at least one DNA binding domain is a zinc finger protein comprising an amino acid sequence of SEQ ID NO: 61. In some embodiments, a ZFP that binds to a SCN1A gene comprises at least 60%, at least 65%, at least 70%, at least 75%, at least 80%, at least 85%, at least 90%, at least 95%, at least 97%, or at least 99% sequence identity to the amino acid sequence of SEQ ID NO: 61.

In some embodiments, the at least one DNA binding domain is a zinc finger protein comprising a recognition helix comprising the amino acid sequence of SEQ ID NO: 17, a recognition helix comprising the amino acid sequence of SEQ ID NO: 18, a recognition helix comprising the amino acid sequence of SEQ ID NO: 19, a recognition helix comprising the amino acid sequence of SEQ ID NO: 20, a recognition helix comprising the amino acid sequence of SEQ ID NO: 21, and/or a recognition helix comprising the amino acid sequence of SEQ ID NO: 22.

In some embodiments, the at least one DNA binding domain is a zinc finger protein comprising a recognition helix comprising SEQ ID NO: 29, a recognition helix comprising SEQ ID NO: 30, a recognition helix comprising SEQ ID NO: 31, a recognition helix comprising SEQ ID NO: 32, a recognition helix comprising SEQ ID NO: 33, and/or a recognition helix comprising SEQ ID NO: 34.

In some embodiments, the at least one DNA binding domain is a zinc finger protein comprising a recognition helix comprising SEQ ID NO: 41, a recognition helix comprising SEQ ID NO: 42, a recognition helix comprising SEQ ID NO: 43, a recognition helix comprising SEQ ID NO: 44, a recognition helix comprising SEQ ID NO: 45, and/or a recognition helix comprising SEQ ID NO: 46.

In some embodiments, the at least one DNA binding domain is a catalytically inactive CRISPR associated protein (Cas protein). In some embodiments, a catalytically inactive Cas protein (or "dead Cas protein") is a dCas9 or dCas12 protein. In some embodiments, a nucleic acid or rAAV further comprises at least one guide nucleic acid (e.g., guide RNA, or gRNA). In some embodiments, the guide nucleic acid comprises a spacer sequence that targets SCN1A. In some embodiments, the guide nucleic acid comprises a spacer sequence having a nucleotide sequence of any one of SEQ ID NO: 85, 86, 89, 90, 93, or 94. In some embodiments, the guide nucleic acid comprises a nucleotide sequence of any one of SEQ ID NO: 83-94. In some embodiments, the guide nucleic acid is encoded by the nucleic acid sequence set forth in any one of SEQ ID NO: 83-94.

In some embodiments, at least one transcriptional regulator domain is a transactivator domain comprising a VP16 domain, VP64 domain, Rta domain, p65 domain, Hsf1 domain, or any combination thereof, such as a VPR domain (VP64+p65+Rta1 domains). In some embodiments, at least one transcriptional regulator domain is encoded by a nucleic acid sequence as set forth in SEQ ID NO: 47. In some embodiments, at least one transactivation domain comprises the amino acid sequence set forth in SEQ ID NO: 48.

In some embodiments, the ITRs which flank the transgene comprise an ITR selected from the group consisting of: AAV1 ITR, AAV2 ITR, AAV3 ITR, AAV4 ITR, AAV5 ITR, AAV6 ITR, AAV8 ITR, AAVrh8 ITR, AAV9 ITR, AAV10 ITR, or AAVrh10 ITR. In some embodiments, the ITR is a ΔTR or an mTR.

In some embodiments, a transgene of an isolated nucleic acid is operably linked to a promoter. In some embodiments, a promoter is a tissue-specific promoter. In some embodiments, a tissue-specific promoter is a neuronal promoter, such as SST, NYP Phosphate-activated glutaminase (PAG), Vesicular glutamate transporter-1 (VGLUT1), Glutamic acid decarboxylase 65 and 57 (GAD65, GAD67), Synapsin I, a-CamKII, Dock10, Prox1, Parvalbumin (PV), Somatostatin (SST), Cholecystokinin (CCK), Calretinin (CR), or Neuropeptide Y (NPY).

In some embodiments, a DNA binding domain of a transgene is fused to a transcriptional regulator domain by a linker domain. In some embodiments, a linker domain is a flexible linker, for example a glycine-rich linker or a glycine-serine linker, or a cleavable linker, such as a photocleavable linker or enzyme (e.g., protease) cleavable linker.

In some embodiments, an isolated nucleic acid comprises a transgene which encodes multiple DNA binding domains, for example, 1, 2, 3, 4, 5, 6, 7, 8, 9, or 10 DNA binding domains. In some embodiments, an isolated nucleic acid comprises a transgene which encodes multiple transcriptional regulator domains, for example 1, 2, 3, 4, 5, 6, 7, 8, 9, or 10 transcriptional regulator domains.

In some embodiments, an isolated nucleic acid or an rAAV is expressed in a cell or subject characterized by aberrant expression or haploinsufficiency (e.g., increased expression, or decreased expression) of a target gene with respect to a normal cell or subject. In some embodiments, an isolated nucleic acid or rAAV is expressed in a cell or subject characterized by deficient (e.g., decreased) expression of a target gene with respect to a normal cell or subject. In some embodiments, a target gene of the isolated nucleic acid or rAAV is SCN1A.

In some embodiments, an AAV capsid serotype is selected from the group consisting of AAV1, AAV2, AAV3, AAV4, AAV5, AAV6, AAV7, AAV8, AAVrh8, AAV9, AAV10, AAVrh10, or AAV.PHPB.

In some aspects, the disclosure provides methods of regulating expression of a target gene. In some embodiments, methods of the disclosure comprise administering an isolated nucleic or rAAV as described herein to a cell or subject that expresses a target gene, wherein the subject is haploinsufficient for the target gene (e.g., haploinsufficient for SCN1A). For example, in some embodiments, expression of a target gene, such as SCN1A, in the cell or subject is deficient (e.g., decreased) with respect to target gene expression in a normal cell or subject. In some embodiments, a cell to which an isolated nucleic acid or rAAV is administered is a neuron. In some embodiments, a neuron is a GABAergic neuron.

In some embodiments, administration of an isolated nucleic acid or rAAV results in target gene expression (e.g., SCN1A expression) that is increased by at least 2-fold, at least 10-fold, at least 20-fold, at least 30-fold, at least 40-fold, at least 50-fold, at least 60-fold, at least 70-fold, at least 80-fold, at least 90-fold, or at least 100-fold relative to a subject that has not been administered an isolated nucleic acid or rAAV. In some embodiments, administration of an isolated nucleic acid or rAAV results in target gene expression (e.g., SCN1A expression) that is increased by at least 2-fold, at least 10-fold, at least 20-fold, at least 30-fold, at least 40-fold, at least 50-fold, at least 60-fold, at least 70-fold, at least 80-fold, at least 90-fold, or at least 100-fold relative to target gene (e.g., SCN1A) expression in the subject prior to being administered the isolated nucleic acid or rAAV.

In some aspects, this disclosure provides a method of regulating gene expression (e.g., expression of SCN1A) in a subject, wherein an isolated nucleic acid or rAAV as described herein is administered to a subject that expresses a target gene. In some embodiments, expression of the target gene in a subject is aberrant (e.g., increased or decreased) with respect to a healthy subject. In some embodiments, a subject is or is suspected of being haploinsufficient with respect to expression of a target gene relative to a healthy subject.

In some embodiments, a subject has or is suspected of having a disease or condition caused by haploinsufficient expression of a target gene. For example a subject that is haploinsufficient for SCN1A expression, in some embodiments, suffers from Dravet syndrome. In some embodiments, an isolated nucleic acid or the rAAV is administered to a subject by intravenous injection, intramuscular injection, inhalation, subcutaneous injection, and/or intracranial injection.

In some aspects, the disclosure provides a composition comprising the isolated nucleic acid or the rAAV as described by the disclosure. In some embodiments, a composition comprises a pharmaceutically acceptable carrier.

In some aspects, the disclosure provides a kit comprising a container housing an isolated nucleic or the rAAV as described by the disclosure. In some embodiments, a kit comprises a container housing a pharmaceutically acceptable carrier. In some embodiments, an isolated nucleic acid or rAAV and a pharmaceutically acceptable carrier are housed in the same container. In some embodiments, a container is a syringe.

In some aspects, the disclosure provides a host cell comprising an isolated nucleic acid or rAAV as described by the disclosure. In some embodiments, a host cell is a eukaryotic cell. In some embodiments, a host cell is a mammalian cell. In some embodiments, a host cell is a human cell, optionally a neuron, for example a GABAergic neuron.

BRIEF DESCRIPTION OF DRAWINGS

FIGS. 1A-1C show chromatographic sequencing data indicating the sequence conservation between the human (HEK) and mouse (HEPG2) SCN1A genes (Consensus sequence—SEQ ID NO: 98; Target sequence—SEQ ID NO: 99; Hep-SCN1A_R4 sequence (top)—SEQ ID NO: 100; Hep-SCN1A_R4 sequence (bottom)—SEQ ID NO: 101.

FIG. 2 shows a sequence alignment of the proximal promoter region of human (SEQ ID NO: 1) and mouse (SEQ ID NO: 2) SCN1A genes, wherein a conserved sequence is highlighted. Within this conserved sequence is a target region of interest for zinc finger protein (ZFP) binding region, which is bolded (SEQ ID NO: 4).

FIG. 3 is a schematic showing the location (SEQ ID NO: 3) of three overlapping target ZFP (ZFP-1, ZFP-2, ZFP-3) (SEQ ID NOs: 5-7) binding sites in the proximal promoter region of the SCN1A gene.

FIGS. 4A-4D shows an alignment of six recognition helix sequences for the individual zinc fingers (Finger 1 through Finger 6; F1-F6) in ZFP-1 which will recognize individual three base regions (DNA triplets denoted in red separated by "•") within the proximal promoter region of the SCN1A gene (SEQ ID NO: 2). FIG. 4A highlights the nucleotide sequence to which zinc fingers 1 through 6 (F1-F6) of ZFP-1 will bind (SEQ ID NO: 3). FIG. 4B shows the three nucleotide sequences recognized by each recognition helix (seven amino acids) of fingers 1 through 6 for ZFP-1 (SEQ ID NOs: 17-22). FIG. 4C shows the amino acid sequences of ZFP-1, which contains 6 fingers, one on each line, wherein the linkers between the fingers are highlighted to designate canonical (TGEKP) and non-canonical (TGSQKP) linker sequences (SEQ ID NOs: 65-70). FIG. 4D shows the nucleotide sequences of ZFP-1 (F1-F6) (SEQ ID NOs: 102-107).

FIGS. 5A-5D shows an alignment of six recognition helix sequences for the individual zinc fingers (Finger 1 through Finger 6; F1-F6) in ZFP-2 which will recognize individual three base regions (DNA triplets denoted in red separated by "*") within the proximal promoter region of the SCN1A gene (SEQ ID NO: 3). FIG. 5A highlights the nucleotide sequence (SEQ ID NO: 3) to zinc fingers 1 through 6 (F1-F6) of ZFP-2 will bind. FIG. 5B shows the first three nucleotides recognized by each recognition helix (seven amino acids) of fingers 1 through 6 for ZFP-2 (SEQ ID NOs: 29-34). FIG. 5C shows the amino acid sequences of ZFP-2, which contains 6 fingers, one on each line (SEQ ID NOs: 69-74), wherein the linkers between the fingers are highlighted to designate canonical (TGEKP) and non-canonical (TGSQKP) linker sequences. FIG. 5D shows the nucleotide sequences of ZFP-2 (F1-F6) (SEQ ID NOs: 108-113).

FIGS. 6A-6D shows an alignment of six recognition helix sequences for the individual zinc fingers (Finger 1 through Finger 6; F1-F6) in ZFP-3 which will recognize individual three base regions (DNA triplets denoted in red separated by "*") within the proximal promoter region of the SCN1A gene (SEQ ID NO: 4). FIG. 6A highlights the nucleotide sequence (SEQ ID NO: 3) to zinc fingers 1 through 6 (F1-F6) of ZFP-3 will bind. FIG. 6B shows the first three nucleotides recognized by each recognition helix (seven amino acids) of fingers 1 through 6 for ZFP-3 (SEQ ID NOs: 41-46). FIG. 6C shows the amino acid sequences of ZFP-3, which contains 6 fingers, one on each line (SEQ ID NOs: 75-80), wherein the linkers between the fingers are highlighted to designate canonical (TGEKP) and non-canonical (TGSQKP) linker sequences. FIG. 6D shows the nucleotide sequences of ZFP-3 (F1-F6) (SEQ ID NOs: 114-119).

Expression levels were normalized to TBP expression levels determined by qRT-PCR in each sample.

Figure 8:
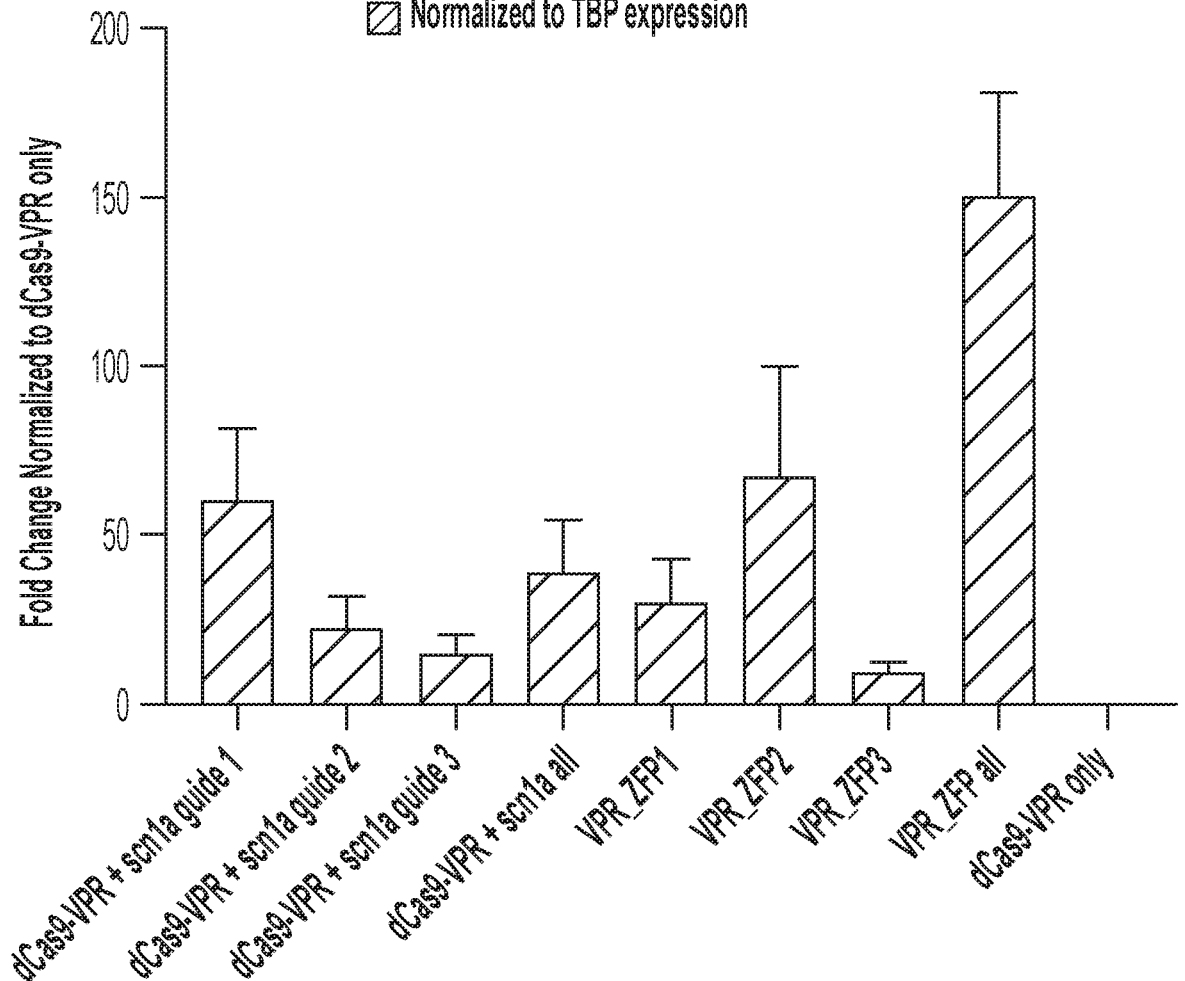

FIG. 8 shows data indicating that the SCN1A-binding ZFPs described in FIGS. 4-6 and Cas9+SCN1A guide RNAs increase SCN1A gene expression in HEK293T cells, as measured by quantitative real-time polymerase chain reaction (qRT-PCR).

DETAILED DESCRIPTION OF INVENTION

Aspects of the disclosure relate to methods and compositions for modulating (e.g., increasing) expression of a target gene in a cell or subject, wherein the target gene is haploinsufficient (i.e., target gene comprises one functional copy). In some embodiments, the target gene is SCN1A.

In some embodiments, the disclosure provides fusion proteins comprising a DNA binding domain, such as a ZFP, and a transcriptional regulator domain. In some embodiments the disclosure provides fusion proteins comprising a DNA binding domain, such as a ZFP, and a transactivator domain (e.g., a VPR domain). In some embodiments, a DNA binding protein binds to a sequence of target gene or a regulatory region of a target gene. In some embodiments, a regulatory region is an enhancer sequence, a promoter sequence, or a repressor sequence. In some embodiments, a promoter sequence may be an internal promoter (e.g., located in an intron of a target gene) or an external promoter (e.g., located upstream of the transcriptional start site of a target gene). In some embodiments, the DNA binding domain of fusion proteins described herein binds a conserved sequence in the promoter region of a target gene (e.g., SCN1A), whereupon the transactivator domain increases gene expression.

In some aspects, the disclosure relates to methods for increasing expression of a target gene (e.g., SCN1A) in a cell or subject. In some embodiments, the target gene contains mutations which render the cell or subject haploinsufficient for the target gene. Therefore, methods and compositions of the disclosure may be utilized, in some embodiments, to treat diseases and disorders associated with haploinsufficiency of a target gene product, for example Dravet syndrome, which typically results from mutations in one copy of the SCN1A gene leading to haploinsufficiency of the voltage-gated sodium channel alpha subunit Nav1.1.

Transactivator Fusion Proteins

Some aspects of the disclosure relate to fusion proteins comprising a DNA binding domain (DBD) and a transactivator domain. As used herein, a fusion protein comprises two or more linked polypeptides that are encoded by two or more separate amino acid sequences. Chimeric proteins, as used herein, are fusion proteins wherein the two or more linked genes are from different species. Fusion proteins are typically recombinantly produced, wherein the genes that encode the fusion protein are in a system that supports the expression of the two or more linked genes and the translation of the resulting mRNAs into recombinant proteins. In some embodiments, fusion proteins are recombinantly produced in prokaryotic or eukaryotic cells. Fusion proteins may be configured in multiple arrangements. For example, one protein (Protein A) is located upstream of a second protein (Protein B). In other fusion protein configurations, Protein B is located upstream of Protein A. In some embodiments, a nucleic acid sequence encoding a DNA binding domain is located upstream of a nucleic acid sequence encoding a transactivator domain, and produces a fusion protein comprising the DBD linked to the transactivator. In some embodiments, a nucleic acid sequence encoding a transactivator domain is located upstream of a nucleic acid sequence encoding a DNA binding domain, and produces a fusion protein comprising the transactivator domain linked to the DNA binding domain. In some embodiments, a fusion protein comprises a transactivator domain located upstream of a DNA binding domain. In some embodiments, a fusion protein comprises a DNA binding domain located upstream of a transactivator domain.

In some embodiments, a fusion protein described by the disclosure comprises a DNA binding domain. As used herein, a "DNA binding domain (DBD)" refers to an independently folded protein comprising at least one structural motif which recognizes double- or single-stranded DNA (dsDNA or ssDNA). Certain DBDs recognize specific sequences (recognition sequence or motif), while other types of DBDs have general affinity for DNA. In some embodiments, a fusion protein described by the disclosure comprises a sequence-specific DBD. In some embodiments, the DBD recognizes (e.g., binds specifically to) a nucleic acid sequence within or neighboring the gene encoding a SCN1A protein (e.g., Nav1.1). Proteins containing DBDs are typically involved in cellular processes such as transcription, replication, repair, and DNA storage. The DBDs in transcription factors recognize specific DNA sequences in the promoter region or in enhancer elements to promote gene expression. Transcription factor DBDs are utilized as fusion proteins in genetic engineering to regulate the expression of target genes and can be mutated to alter the DNA binding specificity or DNA binding affinity and thus regulate the expression of a desired target gene. Examples of DBDs include but are not limited to helix-turn-helix motif, zinc finger motifs (including Cys2-His2 zinc fingers), transcription activator-like effectors (TALEs), winged helix motifs, HMG-boxes, dCas proteins (e.g., dCas9 or dCas12a), homeodomains and OB-fold domains.

In some embodiments, the disclosure relates to zinc finger DBD fusion proteins. As used herein, a "zinc finger protein (ZFP)" refers to a protein which contains at least one structural motif characterized by the coordination of one or more zinc ions which stabilize the protein fold. Zinc fingers are among the most diverse structural motifs found in proteins, and up to 3% of human genes encode zinc fingers. Most ZFPs contain multiple zinc fingers which make tandem contacts with target molecules, including DNA, RNA, and the small protein ubiquitin. "Classical" zinc finger motifs are composed of 2 cysteine amino acids and 2 histidine amino acids ($C_2H_2$) and bind DNA in a sequence-specific manner. These ZFPs, which include transcription factor IIIA (TFIIIA), are typically involved in gene expression. Multiple zinc finger motifs in DNA binding proteins bind and wrap around the outside of a DNA double helix. Due to their relatively small size (e.g., each finger is about 25-40, usually 27-35 amino acids), zinc finger domain fusion proteins are utilized to create DBDs with novel DNA binding specificity. These DBDs can deliver other fused domains (e.g., transcriptional activation or repression domains or epigenetic modification domains) to alter transcription regulation of a target gene. In some embodiments, zinc finger proteins comprise 2 to 8 fingers, wherein each finger contains 27 to 40 amino acids (e.g., 27, 28, 29, 30, 31, 32, 33, 34, 35, 36, 37, 38, 39 or 40 amino acids).

In some embodiments, a ZFP comprises 1, 2, 3, 4, 5, 6, 7, or 8 zinc fingers. Each zinc finger may comprise 25-40, 25-30, 30-35, 35-40, or 40-45 amino acids. In some embodiments, a zinc finger comprises 27-35 amino acids. In some embodiments, a zinc finger comprises 27, 28, 29, 30, 31, 32, 33, 34, or 35 amino acids. A zinc finger may specifically recognize or bind to a target sequence, e.g., a target gene or a regulatory region of a target gene, that is haploinsufficient in a subject. In some embodiments, a zinc finger binds to a target sequence of a SCN1A gene, e.g., a human SCN1A, for example as set forth in SEQ ID NO: 49. In some embodiments, a zinc finger that binds to a target sequence of a SCN1A gene comprises one or more amino acid sequences of SEQ ID NO: 63-80, or a combination thereof. In some embodiments, a zinc finger specifically recognizes or bind to a target sequence comprising a trinucleotide sequence.

In some embodiments, a zinc finger comprises a recognition helix that recognizes or bind to a target sequence, e.g., a target sequence comprising a trinucleotide sequence. In some embodiments, a recognition helix binds to a trinucleotide In some embodiments, a recognition helix comprises 4-10 amino acids. In some embodiments, a recognition helix comprises 4, 6, 7, 8, 9, or 10 amino acids. In some embodiments, a recognition helix binds to a trinucleotide sequence of a SCN1A gene. In some embodiments, a recognition sequence that binds to a SCN1A gene comprises an amino acid sequence of any one of SEQ ID NO: 17-22, 29-34, or 41-46. In some embodiments, a recognition sequence that binds to a SCN1A gene is encoded by any one of SEQ ID NO: 11-16, 23-28, or 35-40. In some embodiments, a zinc finger binds to the same nucleotide sequence as a recognition helix comprising an amino acid sequence of any one of SEQ ID NO: 17-22, 29-34, or 41-46.

In some embodiments, a zinc finger comprises a linker sequence at its C-terminal end that may serve to link or connect said zinc finger to an additional zinc finger. In some embodiments, a linker sequence may be a canonical linker, e.g., comprising an amino acid sequence of TGEKP (SEQ ID NO: 120). In some embodiments, a linker sequence may be a non-canonical linker, e.g., comprising an amino acid sequence of TGSQKP (SEQ ID NO: 121). In some embodiments, a linker sequence may be 2-10 amino acids, e.g., 2, 3, 4, 5, 6, 7, 8, 9, or 10 amino acids.

In some embodiments, a ZFP that binds to a target gene, e.g., a SCN1A gene, comprises six zinc fingers, each of which recognizes or binds to a different trinucleotide sequence of the target gene, e.g., a SCN1A gene. In some embodiments, a ZFP that binds to a SCN1A gene comprises an amino acid sequence of SEQ ID NO: 57. In some embodiments, a ZFP that binds to a SCN1A gene comprises zinc fingers comprising amino acid sequences of SEQ ID NO: 63, 64, 65, 66, 67, and/or 68. In some embodiments, a ZFP that binds to a SCN1A gene comprises recognition helices comprising amino acid sequences of SEQ ID NO: 17, 18, 19, 20, 21, and/or 22. In some embodiments, a ZFP that binds to a SCN1A gene comprises an amino acid sequence of SEQ ID NO: 59. In some embodiments, a ZFP that binds to a SCN1A gene comprises zinc fingers comprising amino acid sequences of SEQ ID NO: 69, 70, 71, 72, 73, and/or 74. In some embodiments, a ZFP that binds to a SCN1A gene comprises recognition helices comprising amino acid sequences of SEQ ID NO: 29, 30, 31, 32, 33, and/or 34. In some embodiments, a ZFP that binds to a SCN1A gene comprises an amino acid sequence of SEQ ID NO: 61. In some embodiments, a ZFP that binds to a SCN1A gene comprises zinc fingers comprising amino acid sequences of SEQ ID NO: 75, 76, 77, 78, 79, and/or 80. In some embodiments, a ZFP that binds to a SCN1A gene comprises recognition helices comprising amino acid sequences of SEQ ID NO: 41, 42 43, 44, 45, and/or 46. In some embodiments, a ZFP that binds to a SCN1A gene comprises at least 60%, at least 65%, at least 70%, at least 75%, at least 80%, at least 85%, at least 90%, at least 95%, at least 97%, or at least 99% sequence identity to SEQ ID NO: 57, 59, or 61, as shown below.

```
(amino acid sequence of ZFP1 protein)
                                  SEQ ID NO: 57
RPFQCRICMRNFSQRGNLVRHIRTHTGEKPFACDICGKKFALSFNLTRHT

KIHTGSQKPFQCRICMRNFSRSDNLTRHIRTHTGEKPFACDICGKKFADR

SHLARHTKIHTGSQKPFQCRICMRNFSQKAHLTAHIRTHTGEKPFACDIC

GRKFARSDNLTRHTKIHLRQKD (amino acid sequence of ZFP2 protein)
                                  SEQ ID NO: 59
RPFQCRICMRNFSRSSNLTRHIRTHTGEKPFACDICGKKFADKRTLIRHT

KIHTGSQKPFQCRICMRNFSQRGNLVRHIRTHTGEKPFACDICGKKFALS

FNLTRHTKIHTGSQKPFQCRICMRNFSRSDNLTRHIRTHTGEKPFACDIC

GRKFADRSHLARHTKIHLRQKD (amino acid sequence of ZFP3 protein)
                                  SEQ ID NO: 61
RPFQCRICMRNFSDRSALARHIRTHTGEKPFACDICGKKFARSDNLTRHT

KNITGSQKPFQCRICMRNFSQSGDLTRHIRTHTGEKPFACDICGKKFAVR

QTLKQHTKIHTGSQKPFQCRICMRNFSAAGNLTRHIRTHTGEKPFACDIC

GRKFARSDNLTRHTKIHLRQKD
```

In some embodiments, DBDs are transcription activator-like effector proteins (TALEs). A TALE may specifically recognize or bind to a target sequence, e.g., a target gene or a regulatory region of a target gene. In some embodiments, a subject is haploinsufficient for the target gene. In some embodiments, a TALE binds to a target sequence of a SCN1A gene, e.g., a human SCN1A as provided in SEQ ID NO: 49. TALE proteins are secreted by bacteria and bind promoter sequences in a host plant to activate the expression of plant genes which aid in bacterial infection. Typically, TALE proteins are manipulated to bind new DNA sequences because the recognize target sequences through a central repeat domain consisting of a variable number of ~30-35 amino acid repeats, wherein each repeat recognizes a single base pair within the target sequence. An array of these repeats are typically necessary to recognize a DNA sequence.

In some embodiments, DBDs are homeodomains. A homeodomain may specifically recognize or bind to a target sequence, e.g., a target gene or a regulatory region of a target gene. In some embodiments, a subject is haploinsufficient for the target gene. In some embodiments, a homeodomain binds to a target sequence of a SCN1A gene, e.g., a human SCN1A as provided in SEQ ID NO: 49. Homeodomains are proteins containing three alpha helices and an N-terminal arm that are responsible for recognizing a target sequence. A homeodomain typically recognizes a small DNA sequence (~4 to 8 base pairs), however these domains can be fused in tandem with other DNA-binding domains (either other homeodomains or zinc finger proteins) to recognize longer extended sequences (12 to 24 base pairs). Therefore, homeodomains can be components of DBD that recognize unique sequences within the human genome.

In some embodiments, the at least one DNA binding domain is a catalytically inactive CRISPR associated protein (Cas protein). A catalytically inactive Cas protein (also known as dCas or "dead Cas protein") is a Cas protein that has been modified or mutated such that it has diminished nuclease activity (e.g., endonuclease activity) or lacks all nuclease activity (e.g., endonuclease activity). In some embodiments, a catalytically inactive Cas protein is a dCas9 or dCas12 protein. In some embodiments, DBDs are dCas proteins (also known as 'dead Cas') such as dCas9 or dCas12a. dCas proteins are mutant variants of CRISPR associated proteins (Cas, e.g., Cas9 or Cas12a) that have been mutated such that they are catalytically inactivated, i.e., incapable of nucleotide cleavage. A dCas may specifically recognize or bind to a target sequence, e.g., a target gene or a regulatory region of a target gene. A complex comprising a dCas protein and a guide nucleic acid (e.g., gRNA) can target and/or bind to specific nucleotide sequences or genes that are complementary to the guide nucleic acid. In some embodiments, a subject is haploinsufficient for the target gene. In some embodiments, a dCas binds to a target sequence of a SCN1A gene, e.g., a human SCN1A as provided in SEQ ID NO: 49. However, dCas proteins retain their ability to recognize and bind to target DNA sequences when bound to a guide nucleic acid (e.g., a guide RNA, gRNA, or sgRNA) that is complementary or partially complementary to said target DNA sequence. In some embodiments, a guide nucleic acid for targeting dCas (e.g., dCas9) proteins to SCN1A comprise a spacer sequence having any one of SEQ ID NO: 85, 86, 89, 90, 93, or 94. In some embodiments, a guide nucleic acid for targeting dCas (e.g., dCas9) proteins to SCN1A comprise a spacer sequence having at least 15 (e.g., at least 16, 17, 18, 19, or 20) consecutive nucleotides of any one of SEQ ID NO: 85, 86, 89, 90, 93, or 94. In some embodiments, a guide nucleic acid for targeting dCas (e.g., dCas9) proteins to SCN1A comprises any one of SEQ ID NO: 83, 84, 87, 88, 91, or 92. In some embodiments, a guide nucleic acid for targeting dCas (e.g., dCas9) proteins to SCN1A comprises or consists of any one of SEQ ID NOs: 83-94. Therefore, dCas endonucleases can be components of DBD that recognize unique sequences within the human genome. In some embodiments, a fusion protein comprises a dCas9 protein and a transactivation domain (e.g., a VPR domain).

The disclosure relates, in some aspects, to DNA binding domains that bind to a gene encoding a voltage-gated sodium channel (e.g., Na$_v$1.1). In some embodiments, a gene that encodes a voltage-gated sodium channel is a SCN1A gene, and comprises the sequence set forth in SEQ ID NO: 49. In some embodiments, a DNA binding domain binds to an untranslated region of a target gene, such as a 3'-untranslated region (3'UTR) or a 5'-untranslated region (5'UTR). In some embodiments, an untranslated region comprises a regulatory sequence, for example an enhancer, a promoter, intronic, or a repressor sequence. In some embodiments, a DNA binding domain is a zinc finger protein comprising the sequences set forth in SEQ ID NOs: 57-62. In some embodiments, a DNA binding domain binds to a nucleic acid sequence set forth in any one of SEQ ID NOs: 5-7.

The number of DNA binding domains encoded by a transgene may vary. In some embodiments, a transgene encodes one DNA binding domain. In some embodiments, a transgene encodes 2 DNA binding domains. In some embodiments, a transgene encodes 3 DNA binding domains. In some embodiments, a transgene encodes 4 DNA binding domains. In some embodiments, a transgene encodes 5 DNA binding domains. In some embodiments, a transgene encodes 6 DNA binding domains. In some embodiments, a transgene encodes 7 DNA binding domains. In some embodiments, a transgene encodes 8 DNA binding domains. In some embodiments, a transgene encodes 9 DNA binding domains. In some embodiments, a transgene encodes 10 DNA binding domains. In some embodiments, a transgene encodes more than 10 (e.g., 20, 30, 50, 100, etc.) DNA binding domains. The DNA binding domains may be the same DNA binding domain (e.g., multiple copies of the same DBD), different DNA binding domains (e.g., each DBD binds a unique sequence), or a combination thereof.

The disclosure relates, in some aspects, to fusion proteins comprising a transactivator domain. As used herein, a "transactivation domain" refers to a scaffold domain in a transcription factor which contains binding sites for other proteins which regulate gene expression, such as transcription co-regulators. In some embodiments, a transactivation domain (also known as transcriptional activation domain) acts in conjunction with a DBD to activate transcription from a promoter or enhancer, either directly through contacting transcription factors, or indirectly through coactivator proteins. Transactivation domains (TADs) are commonly named for their amino acid compositions, wherein the amino acids are either essential for activity or are the most abundant in the TAD. TADs are utilized as fusion proteins in genetic engineering to regulate the expression of target genes and can be mutated to alter the level of transcriptional activation and thus expression of the target gene. Examples of transactivation domains include but are not limited to GAL4, HAP1, VP16, P65, RTA, and GCN4.

In some embodiments, a transactivator domain comprises a VP64 domain. VP64 is an acidic TAD composed of four tandem copies of VP16 protein, which is naturally expressed by herpes simplex virus. When fused to a DBD which binds at or near the promoter of a gene, VP64 acts as a strong transcriptional activator and can thus be utilized to regulate expression of a target gene (e.g., SCN1A). The VP64 domain typically consists of a tetrameric repeat of the minimal activation domain of the herpes simplex protein VP16. In some embodiments, the VP64 domain comprises four repeats of amino acid residues 437-448 in VP16. In some embodiments, a VP16 protein is encoded by a human herpes virus 2 UL48 gene, which comprises the sequence set forth in NCBI Ref. Seq. Accession No: NC_001798.2. In some embodiments, a VP16 gene comprises a nucleotide sequence that is 99% identical, 95% identical, 90% identical, 80% identical, 70% identical, 60% identical, or 50% identical to the amino acid sequence encoded by the nucleic acid sequence set forth in NCBI Ref. Seq Accession No: YP_009137200.1. In some embodiments, a VP16 protein comprises an amino acid sequence that is 99% identical, 95% identical, 90% identical, 80% identical, 70% identical, 60% identical, or 50% identical to the amino acid sequence set forth in NCBI Ref. Seq. Accession No Q69113-1. In some embodiments, a VP16 gene comprises a nucleotide sequence that is 99% identical, 95% identical, 90% identical, 80% identical, 70% identical, 60% identical, or 50% identical to the amino acid sequence encoded by the nucleic acid sequence set forth in SEQ ID NO: 51. In some embodiments, a VP16 protein comprises an amino acid sequence that is 99% identical, 95% identical, 90% identical, 80% identical, 70% identical, 60% identical, or 50% identical to the amino acid sequence set forth in SEQ ID NO: 52.

In some embodiments, a transactivator domain comprises a P65 activation domain. P65 is a subunit of the NF-κβ transcription factor which contains two adjacent acidic TADs at its C-terminus. When fused to a DBD which binds at or near the promoter of a gene, the p65 protein acts as a strong transcriptional activator and can thus be utilized to regulate expression of a target gene, for example as described by Urlinger, et al. "The p65 domain from NF-kappaB is an efficient human activator in the tetracyclineregulatable gene expression system," *Gene,* 2000. In some embodiments, a p65 protein is encoded by a human RELA gene, which comprises the sequence set forth in NCBI Ref. Seq Accession No: NM_001145138.1, NM_001243984.1, NM_001243985.1, or NM_021975.3. In some embodiments, a RELA gene comprises a nucleotide sequence that is 99% identical, 95% identical, 90% identical, 80% identical, 70% identical, 60% identical, or 50% identical to the amino acid sequence encoded by the nucleic acid sequence set forth in any of NCBI Ref. Seq ID Nos: NM_001145138.1, NM_001243984.1, NM_001243985.1, or NM_021975.3. In some embodiments, a p65 protein comprises an amino acid sequence that is 99% identical, 95% identical, 90% identical, 80% identical, 70% identical, 60% identical, or 50% identical to the amino acid sequence set forth in NP_001138610.1, NP_001230913.1, NP_001230914.1, and NP_068110.3. In some embodiments, a RELA gene comprises a nucleotide sequence that is 99% identical, 95% identical, 90% identical, 80% identical, 70% identical, 60% identical, or 50% identical to the amino acid sequence encoded by the nucleic acid sequence set forth in SEQ ID NO: 53. In some embodiments, a p65 protein comprises an amino acid sequence that is 99% identical, 95% identical, 90% identical, 80% identical, 70% identical, 60% identical, or 50% identical to the amino acid sequence set forth in SEQ ID NO: 54.

In some embodiments, a transactivator domain comprises an RTA domain. RTA is a hydrophobic TAD derived from Epstein Barr virus which is a potent transactivation domain which binds to the enhancer region to promote expression of several viral genes. When fused to a DBD which binds at or near the promoter of a gene, the RTA protein acts as a strong transcriptional activator and can thus be utilized to regulate expression of a target gene, for example as described by Miyazawa, et al., "IL-10 promoter transactivation by the viral K-RTA protein involves the host-cell transcription factors, specificity proteins 1 and 3," *Journal of Biological Chemistry,* 2018. In some embodiments, a RTA protein is encoded by an Epstein-Barr virus BRLF1 gene, which comprises the sequence set forth in NCBI Ref. Seq Accession No: YP_041674.1. In some embodiments, a BRLF1 gene comprises a nucleotide sequence that is 99% identical, 95% identical, 90% identical, 80% identical, 70% identical, 60% identical, or 50% identical to the amino acid sequence encoded by the nucleic acid sequence set forth in any of NCBI Ref. Seq ID Nos: YP_041674.1. In some embodiments, a RTA protein comprises an amino acid sequence that is 99% identical, 95% identical, 90% identical, 80% identical, 70% identical, 60% identical, or 50% identical to the amino acid sequence set forth in YP_041674.1. In some embodiments, a BRLF1 gene comprises a nucleotide sequence that is 99% identical, 95% identical, 90% identical, 80% identical, 70% identical, 60% identical, or 50% identical to the amino acid sequence encoded by the nucleic acid sequence set forth in SEQ ID NO: 55. In some embodiments, a RTA protein comprises an amino acid sequence that is 99% identical, 95% identical, 90% identical, 80% identical, 70% identical, 60% identical, or 50% identical to the amino acid sequence set forth in SEQ ID NO: 56.

The disclosure is based, in part, on fusion proteins comprising a hybrid transactivator domain. A "hybrid transactivator domain", as used herein, refers to a fusion protein comprising more than one transcription activating protein or portions thereof (e.g., 2, 3, 4, 5, or more transcription activating proteins, or portions thereof). Hybrid transactivation domains are utilized in genetic engineering to increase the expression of target genes. In some embodiments of the disclosure, a tripartite hybrid transactivation domain comprising the nucleotide sequence for VP64-P65-RTA (VPR), as described in Chavez, et al. "Highly efficient Cas9-mediated transcriptional programming", *Nat Methods,* 2015, (SEQ ID NO: 47) is utilized to increase target gene (e.g. SCN1A) expression.

In some embodiments, fusion proteins described herein may comprise a DBD (e.g., a ZFP) and a transcriptional repressor protein. In some aspects, the disclosure relates to fusion proteins comprising a transcriptional repressor domain. A "transcriptional repressor" protein, as used herein, generally refers to a polypeptide which downregulates the expression of a target gene. Examples of transcriptional repressors include, but are not limited to, KRAB, SMRT/TRAC-2, and NCoR/RIP-13. In some embodiments, such transcriptional repressor fusion proteins are useful for reducing the expression level of a target gene (e.g., a gene that is over-expressed in a gain-of-function disease).

Isolated Nucleic Acids

An isolated nucleic acid sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some aspects, the disclosure relates to isolated nucleic acids (e.g., expression constructs, such as rAAV vectors) that are configured to express one or more ZFP-transactivation domain fusion proteins. In some embodiments, a fusion protein comprises between 1 and 10 (e.g., 1, 2, 3, 4, 5, 6, 7, 8, 9, or 10) DBDs and/or between 1 and 10 (e.g., 1, 2, 3, 4, 5, 6, 7, 8, 9, or 10) transactivator domains. In some embodiments, a fusion protein comprises more than 10 DBS and/or more than 10 transactivator domains.

In some aspects of the disclosure, a DNA binding domains is fused to a transcriptional regulator domain indirectly through a linker. As used herein "a linker" is generally a stretch of polypeptides which structurally join two distinct polypeptides within a single transgene. In some embodiments, a linker is flexible to allow movement of the distinct polypeptides. In some embodiments, a flexible linker comprises glycine residues. In some embodiments, a flexible linker comprises a mixture of glycine and serine residues. In some embodiments, a linker is cleavable, allowing the polypeptides to be separated. In some embodiments, a cleavable linker is cut by a protease. In some embodiments, the protease is trypsin or Factor X.

In some embodiments a linker comprises between 5 and 30 amino acids (e.g., 5, 6, 7, 8, 9, 10, 11, 12, 13, 14, 15, 16, 17, 18, 19, 20, 21, 22, 23, 24, 25, 26, 27, 28, 29, or 30 amino acids). In some embodiments, a linker comprises between 3 and 30 amino acids (e.g., 3, 4, 5, 6, 7, 8, 9, 10, 11, 12, 13, 14, 15, 16, 17, 18, 19, 20, 21, 22, 23, 24, 25, 26, 27, 28, 29, or 30 amino acids). In some embodiments, a linker comprises between 3 and 20 amino acids (e.g., 3, 4 5, 6, 7, 8, 9, 10, 11, 12, 13, 14, 15, 16, 17, 18, 19, or 20 amino acids).

The disclosure is based, in part, on fusion proteins that are engineered to increase expression of a gene encoding a voltage-gated sodium ion channel subunit protein (also referred to as a SCN protein), for example SCN1A. As used herein, "a SCN protein" refers to a sodium ion channel protein which mediates the voltage-dependent sodium ion permeability of excitable membranes, allowing sodium ions to pass through the membrane. Examples of SCN proteins in humans include but are not limited to SCN1A, SCN3A, SCN5A, SCN10A, and SCN11A. In some embodiments, a SCN protein is SCN1A (also referred to as Nav1.1), which encodes a Type 1 $\alpha_1$ ion channel subunit. In some embodiments, a SCN protein is SCN1B protein, which encodes a Type 1 $\beta_1$ ion channel subunit or SCN1C protein. In some embodiments, a SCN protein is a combination of SCN1A, SCN1B, and/or SCN1C proteins. As disclosed herein, a SCN protein can be a portion or a fragment of a SCN protein. In some embodiments, a SCN protein as disclosed herein is a variant of a SCN protein, such as a point mutant or a truncated mutant.

In humans, SCN1A is encoded by the SCN1A gene (Gene ID: 6323, human), which is conserved in chimpanzee, Rhesus monkey, dog, cow, mouse, rat, and chicken. The SCN1A gene in human is primarily expressed in brain, lung, and testis. In some embodiments, SCN1A proteins comprise five structural repeats (I, II, III, IV, Q).

In some embodiments, a SCN1A protein is encoded is encoded by a human SCN1A gene, which comprises the sequence set forth in NCBI Ref. Seq ID No: NM_001165963.2, NM_00165964.2, NM_001202435.2, NM_001353948.1, NM_001353949.1, NM_001353950.1, NM_00135395.1, NM_001353952.1, NM_001353954.1, NM_00353955.1, NM_001353957.1, NM_001353958.1, NM_001353960.1, NM_001353961.1, or NM_006920.5. In some embodiments, a SCN1A protein is encoded by a mouse SCN1A gene, which comprises the sequence set forth in NCBI Ref Seq ID No: NM_001313997.1 or NM_018733.2. In some embodiments, a SCN1A protein comprises an amino acid sequence that is 99% identical, 95% identical, 90% identical, 80% identical, 70% identical, 60% identical, or 50% identical to the amino acid sequence encoded by the nucleic acid sequence set forth in either NCBI Ref. Seq ID No: NG_011906.1, NM_001313997.1 or NM_018733.2. In some embodiments, a SCN1A gene comprises an amino acid sequence that is 99% identical, 95% identical, 90% identical, 80% identical, 70% identical, 60% identical, or 50% identical to the sequence set forth in SEQ ID NO: 50. In some embodiments, a human SCN1A protein comprises the sequence set forth in NCBI Ref. Seq ID No: NP_001159435.1, NP_0011159436.1, NP_001189364.1, NP_001340877.1, NP_001340878.1, NP_001340879.1, NP_001340880.1, NP_001340881.1, NP_001340883.1, NP_001340884.1, NP_001340886.1, NP_001340887.1, NP_001340889.1, NP_001340890.1, NP_00851.3. In some embodiments, a SCN1A protein comprises an amino acid sequence that is 99% identical, 95% identical, 90% identical, 80% identical, 70% identical, 60% identical, or 50% identical to the amino acid sequence encoded by the nucleic acid sequence set forth in either NCBI Ref. Seq ID No: NG_011906.1, NM_001313997.1 or NM_018733.2. In some embodiments, a mouse SCN1A protein comprises the sequence set forth in NCBI Ref. Seq ID No: NP_001300926.1 or NP_061203.2. In some embodiments, a human SCN1A protein comprises an amino acid sequence that is 99% identical, 95% identical, 90% identical, 80% identical, 70% identical, 60% identical, or 50% identical to the nucleic acid sequence set forth in SEQ ID NO: 49.

The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise a region encoding, for example, a protein and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the disclosure. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein.

A region comprising a transgene (e.g., comprising a fusion protein, etc.) may be positioned at any suitable location of the isolated nucleic acid that will enable expression of the fusion protein.

It should be appreciated that in cases where a transgene encodes more than one polypeptide, each polypeptide may be positioned in any suitable location within the transgene. For example, a nucleic acid encoding a first polypeptide may be positioned in an intron of the transgene and a nucleic acid sequence encoding a second polypeptide may be positioned in another untranslated region (e.g., between the last codon of a protein coding sequence and the first base of the poly-A signal of the transgene).

A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polypro-tein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is a P2 promoter. In some embodiments, a promoter is a chicken β-actin (CBA) promoter. In some embodiments, a promoter is two CBA promoters. In some embodiments, a promoter is two CBA promoters separated by a CMV enhancer. In some embodiments, a promoter is a CAG promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, a transgene which encodes a fusion protein comprising a DBD and a transactivator is operably linked to a promoter. In some embodiments, the promoter is a constitutive promoter. In some embodiments, the promoter is an inducible promoter. In some embodiments, the promoter is a tissue-specific promoter. In some embodiments, the promoter is specific for nervous tissue. In some embodiments, the promoter is SST or NPY promoter.

Aspects of the disclosure relate to an isolated nucleic acid comprising more than one promoter (e.g., 2, 3, 4, 5, or more promoters). For example, in the context of a construct having a transgene comprising a first region encoding a protein and a second region encoding a protein it may be desirable to drive expression of the first protein coding region using a first promoter sequence (e.g., a first promoter sequence operably linked to the protein coding region), and to drive expression of the second protein coding region with a second promoter sequence (e.g., a second promoter sequence operably linked to the second protein coding region). Generally, the first promoter sequence and the second promoter sequence can be the same promoter sequence or different promoter sequences. In some embodiments, the first promoter sequence (e.g., the promoter driving expression of the protein coding region) is a RNA polymerase III (pol III) promoter sequence. Non-limiting examples of pol III promoter sequences include U6 and H1 promoter sequences. In some embodiments, the second promoter sequence (e.g., the promoter sequence driving expression of the second protein) is a RNA polymerase II (pol II) promoter sequence. Non-limiting examples of pol II promoter sequences include T7, T3, SP6, RSV, and cytomegalovirus promoter sequences. In some embodiments, a pol III promoter sequence drives expression of the first protein coding region. In some embodiments, a pol II promoter sequence drives expression of the second protein coding region.

Recombinant Adeno-Associated Viruses (rAAVs)

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV1, AAV2, AAV3, AAV4, AAV5, AAV6, AAV7, AAV8, AAVrh8, AAV9, AAV10, AAVrh10, and AAV.PHP.B. In some embodiments, an AAV capsid protein is of a serotype derived from a non-human primate, for example AAVrh8 serotype. In some embodiments, an AAV capsid protein is of a serotype derived for broad and efficient CNS transduction, for example AAV.PHP.B. In some embodiments, the capsid protein is of AAV serotype 9.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a transgene (e.g., a DNA binding domain fused to a transcriptional regulator domain). In some embodiments, the host cell is a mammalian cell, a yeast cell, a bacterial cell, an insect cell, a plant cell, or a fungal cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. In some embodiments, a host cell is a neuron, optionally a GABAergic neuron. A "GABAergic neuron", as used herein, is a neural cell that generates gamma aminobutyric acid (GABA). In mammals, GABA is a neurotransmitter that is widely distributed in the nervous system which binds and represses the neurons which it binds. As such, GABA is implicated in numerous disorders affecting the nervous system, including epilepsy, autism, and anxiety. Studies in SCN1A hemizygote and knock-out mice have observed a profound sodium current deficit in GABAergic neurons in the brain. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, useful vectors are contemplated to be those vectors in which the nucleic acid segment to be transcribed is positioned under the transcriptional control of a promoter.

A "promoter" refers to a DNA sequence recognized by the synthetic machinery of the cell, or introduced synthetic machinery, required to initiate the specific transcription of a gene. The phrases "operatively linked", "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product from a transcribed gene. The foregoing methods for packaging recombinant vectors in desired AAV capsids to produce the rAAVs of the disclosure are not meant to be limiting and other suitable methods will be apparent to the skilled artisan.

Methods for Regulating Target Gene Expression

Methods for regulating gene expression in a cell or subject are provided by the disclosure. The methods typically involve administering to a cell or a subject an isolated nucleic acid or rAAV comprising a transgene which encodes a fusion protein comprising a DNA binding domain (e.g., a ZFP domain) and a transactivation domain. In some embodiments, a fusion protein comprises ZFP and VP64 transactivator. In some embodiments, a fusion protein comprises ZFP and p65 transactivator. In some embodiments, a fusion protein comprises ZFP and RTA transactivator. In some embodiments, a fusion protein comprises ZFP and VPR transactivator. In some embodiments, the method involves administering to a cell or a subject a dCas9 protein and at least one guide nucleic acid that targets SCN1A (e.g., a guide nucleic acid comprising any one of SEQ ID NO: 83-94 or encoded by any one of SEQ ID NO: 83-94).

Administering an isolated nucleic acid or an rAAV encoding the fusion protein (e.g., a fusion protein comprising a transactivator) to a cell or subject, in some embodiments, results in increased expression of a target gene (e.g., SCN1A). Thus, in some embodiments, compositions and methods described by the disclosure are useful for treating conditions resulting from a haploinsufficiency of a target gene, such as Dravet syndrome which results from haploinsufficiency of SCN1A gene.

As used herein, a "haploinsufficiency" refers to a genetic condition wherein one copy of a gene (e.g., SCN1A) is inactivated, e.g., by genetic mutation, or deleted, and the remaining functional copy of the gene is not adequate to produce an amount of gene product sufficient to preserve normal function of the gene.

Dravet syndrome, also known as Severe Myoclonic Epilepsy of Infancy, is a rare, life-long form of epilepsy which typically manifests in the first three years of life. Dravet syndrome is characterized by prolonged and frequent seizures, behavioral and developmental delays, movement and balance issues, delayed language and speech issues, and disruptions of the autonomic nervous system. In some embodiments, a subject has a haploinsufficiency associated with Dravet syndrome, such as one copy of the SCN1A gene being mutated, resulting in reduced SCN1A protein in a cell or subject. The majority of Dravet syndrome patients carry SCN1A mutations which are translated into truncated proteins; other SCN1A mutations associated with Dravet syndrome include splice-site and missense mutations, as well as mutations randomly distributed throughout the SCN1A gene. In some embodiments, a fusion protein of the disclosure comprises a ZFP domain that specifically targets (e.g., binds to) a SCN1A gene and a transactivation domain. In some embodiments, a composition for targeting SCNA1 comprises (i) a fusion protein comprising a dCas protein and a transactivation domain, and (ii) a guide nucleic acid (e.g., a gRNA) that specifically targets (e.g., binds to) a SCN1A gene.

In some embodiments, a subject has a haploinsufficiency associated with MED13L haploinsufficiency syndrome, wherein the subject only has a single functional copy of the MED13L gene. Subjects suffering from MED13L haploinsufficiency syndrome typically have a mutation in their second, non-functional copy of the MED13L gene. MED13L haploinsufficiency syndrome is characterized by intellectual disability, speech problems, distinctive facial features, and developmental delay. In some embodiments, a fusion protein of the disclosure comprises a ZFP domain that specifically targets (e.g., binds to) a MED13L gene and a transactivation domain. In some embodiments, a composition for targeting MED13L comprises (i) a fusion protein comprising a dCas protein and a transactivation domain, and (ii) a guide nucleic acid (e.g., a gRNA) that specifically targets (e.g., binds to) a MED13L gene.

In some embodiments, a subject has a haploinsufficiency associated with myelodysplastic syndromes. Subjects suffering from a myelodysplastic syndrome typically have a mutation in one copy of the isocitrate dehydrogenase 1 (IDH1), isocitrate dehydrogenase 2 (IDH2), and/or GATA2 genes. Myelodysplastic syndrome are a group of cancers in which immature blood cells in the bone marrow do not mature into healthy blood cells. Occasionally, this syndrome can lead to acute myeloid leukemia. In some embodiments, a fusion protein of the disclosure comprises a ZFP domain that specifically targets (e.g., binds to) an IDH1 gene and a transactivation domain. In some embodiments, a composition for targeting IDH1 comprises (i) a fusion protein comprising a dCas protein and a transactivation domain, and (ii) a guide nucleic acid (e.g., a gRNA) that specifically targets (e.g., binds to) a IDH1 gene. In some embodiments, a fusion protein of the disclosure comprises a ZFP domain that specifically targets (e.g., binds to) an IDH2 gene and a transactivation domain. In some embodiments, a composition for targeting IDH2 comprises (i) a fusion protein comprising a dCas protein and a transactivation domain, and (ii) a guide nucleic acid (e.g., a gRNA) that specifically targets (e.g., binds to) a IDH2 gene. In some embodiments, a fusion protein of the disclosure comprises a ZFP domain that specifically targets (e.g., binds to) an GATA2 gene and a transactivation domain. In some embodiments, a composition for targeting GATA2 comprises (i) a fusion protein comprising a dCas protein and a transactivation domain, and (ii) a guide nucleic acid (e.g., a gRNA) that specifically targets (e.g., binds to) a GATA2 gene.

In some embodiments, a subject has a haploinsufficiency associated with DiGeorge syndrome. Subjects suffering from a DiGeorge syndrome typically have a deletion of 30 to 40 genes in the middle of chromosome 22 at a location known as 22q11.2. In particular, the disease may be characterized by haploinsufficiency of the TBX gene. DiGeorge syndrome is characterized by congenital heart problems, specific facial features, frequent infections, developmental delay, learning problems and cleft palate. In some embodiments, a fusion protein of the disclosure comprises a ZFP domain that specifically targets (e.g., binds to) a TBX gene and a transactivation domain. In some embodiments, a composition for targeting TBX comprises (i) a fusion protein comprising a dCas protein and a transactivation domain, and (ii) a guide nucleic acid (e.g., a gRNA) that specifically targets (e.g., binds to) a TBX gene.

In some embodiments, a subject has a haploinsufficiency associated with CHARGE syndrome. In a majority of cases, subjects suffering from CHARGE syndrome are haploinsufficient for the CHD7 gene. CHARGE syndrome is characterized by coloboma of the eye, heart defects, atresia of the nasal choanae, retardation of growth and/or development, genital and/or urinary abnormalities, and ear abnormalities and deafness. In some embodiments, a fusion protein of the disclosure comprises a ZFP domain that specifically targets (e.g., binds to) a CHD7 gene and a transactivation domain. In some embodiments, a composition for targeting CHD7 comprises (i) a fusion protein comprising a dCas protein and a transactivation domain, and (ii) a guide nucleic acid (e.g., a gRNA) that specifically targets (e.g., binds to) a CHD7 gene.

In some embodiments, a subject has a haploinsufficiency associated with Ehlers-Danlos syndrome. Subjects suffering from Ehlers-Danlos syndrome may be haploinsufficient for the COL1A1, COL1A2, COL3A1, COL5A1, COL5A2, TNXB, ADAMTS2, PLOD1, B4GALT7, DSE, and/or D4ST1/CHST14 genes. Ehlers-Danlos syndrome is characterized by skin hyperelasticity and may result in aortic dissection, scoliosis, and early-onset osteoarthritis. In some embodiments, a fusion protein of the disclosure comprises a ZFP domain that specifically targets (e.g., binds to) any one of COL1A1, COL1A2, COL3A1, COL5A1, COL5A2, TNXB, ADAMTS2, PLOD1, B4GALT7, DSE, or D4ST1/CHST14 genes and a transactivation domain. In some embodiments, a composition for targeting any one of COL1A1, COL1A2, COL3A1, COL5A1, COL5A2, TNXB, ADAMTS2, PLOD1, B4GALT7, DSE, or D4ST1/CHST14 comprises (i) a fusion protein comprising a dCas protein and a transactivation domain, and (ii) a guide nucleic acid (e.g., a gRNA) that specifically targets (e.g., binds to) any one of COL1A1, COL1A2, COL3A1, COL5A1, COL5A2, TNXB, ADAMTS2, PLOD1, B4GALT7, DSE, or D4ST1/CHST14 gene.

In some embodiments, a subject has a haploinsufficiency associated with frontotemporal dementias (FTD). Subjects suffering from FTD are haploinsufficient for the MAPT gene, which encodes Tau protein, and/or the GRN gene. FTD is characterized by memory loss, lack of social awareness, poor impulse control, and difficulties in speech. In some embodiments, a fusion protein of the disclosure comprises a ZFP domain that specifically targets (e.g., binds to) a MAPT gene and a transactivation domain. In some embodiments, a composition for targeting MAPT comprises (i) a fusion protein comprising a dCas protein and a transactivation domain, and (ii) a guide nucleic acid (e.g., a gRNA) that specifically targets (e.g., binds to) a MAPT gene. In some embodiments, a fusion protein of the disclosure comprises a ZFP domain that specifically targets (e.g., binds to) a GRN gene and a transactivation domain. In some embodiments, a composition for targeting GRN comprises (i) a fusion protein comprising a dCas protein and a transactivation domain, and (ii) a guide nucleic acid (e.g., a gRNA) that specifically targets (e.g., binds to) a GRN gene.

In some embodiments, a subject has a haploinsufficiency associated with Holt-Oram syndrome. Subjects suffering from Holt-Oram syndrome are haploinsufficient for the TBX5 gene. Holt-Oram syndrome is characterized by heart complications, including congenital heart defects and cardiac conduction disease. In some embodiments, a fusion protein of the disclosure comprises a ZFP domain that specifically targets (e.g., binds to) a TBX5 gene and a transactivation domain. In some embodiments, a composition for targeting TBX5 comprises (i) a fusion protein comprising a dCas protein and a transactivation domain, and (ii) a guide nucleic acid (e.g., a gRNA) that specifically targets (e.g., binds to) a TBX5 gene.

In some embodiments, a subject has a haploinsufficiency associated with Marfan syndrome. Subjects suffering from Marfan syndrome are typically haploinsufficient for the FBN1 gene, encoding fibrillin-1 protein. Marfan syndrome is characterized by disproportionate limb lengths, early-onset arthritis, heart complications, and/or dysfunction of the autonomic nervous system. In some embodiments, a fusion protein of the disclosure comprises a ZFP domain that specifically targets (e.g., binds to) a FBN1 gene and a transactivation domain. In some embodiments, a composition for targeting FBN1 comprises (i) a fusion protein comprising a dCas protein and a transactivation domain, and (ii) a guide nucleic acid (e.g., a gRNA) that specifically targets (e.g., binds to) a FBN1 gene.

The disclosure is based, in part, on methods of administering a fusion protein as described herein to a subject. In some embodiments, the fusion protein comprises a DBD and a transcriptional activator. In some embodiments, the DBD is a ZNF, a TALE, a dCas protein (e.g., dCas9 or dCas12a), or a homeodomain that binds to a SCN1A gene. In some embodiments, the transcriptional activator is VP64, p65, RTA, or a tripartite transcription activator comprising VP64-p65-RTA (VPR). In some embodiments, the fusion protein is flanked by AAV inverted terminal repeat (ITR) sequences. In some embodiments, the fusion protein is operably linked to a promoter. In some embodiments, the subject has or is suspected of having mutations in SCN1A that result in SCN1A protein haploinsufficiency. In some embodiments, the subject has or is suspected of having Dravet syndrome.

In some aspects, the disclosure provides methods of modulating (e.g., increasing, decreasing, etc.) expression of a target gene in a cell. In some embodiments, the disclosure provides methods of increasing expression of a target gene (e.g., SCN1A) in a cell. In some embodiments, a cell is a mammalian cell. In some embodiments, a cell is in a subject (e.g., in vivo). In some embodiments, a subject is a mammalian subject, for example a human. In some embodiments, a cell is a nervous system cell (central nervous system cell or peripheral nervous system cell), for example a neurons (e.g., GABAergic neurons, unipolar neurons, bipolar neurons, Basket cells, Betz cells, Lugaro cells, spiny neurons, Purkinje cells, Pyrimidal cells, Renshaw cells, Granule cells, motor neurons, spindle cells, etc.) or glial cells (e.g., astrocytes, oligodendrocytes, ependymal cells, radial glia, Schwann cells, Satellite cells, etc.).

In a "normal" cell or subject, the expression of a target gene (e.g., SCN1A) is sufficient such that cell or subject is not haploinsufficient with regard to the target gene (e.g., SCN1A). In some embodiments, "improved" or "increased" expression or activity of a transgene is measured relative to expression or activity of that transgene in a cell or subject who has not been administered one or more isolated nucleic acids, rAAVs, or compositions as described herein. In some embodiments, "improved" or "increased" expression or activity of a transgene is measured relative to expression or activity of that transgene in the subject after the subject has been administered (e.g., gene expression is measured pre- and post-administration of) one or more isolated nucleic acids, rAAVs, or compositions as described herein For example, in some embodiments, "improved" or "increased" expression of SCN1A in a cell or subject is measured relative to a cell or subject who has not been administered a transgene encoding a fusion ZFP-transactivator. In some embodiments, methods described by the disclosure result in SCN1A expression and/or activity in a subject that is increased between 2-fold and 100-fold (e.g., 2-fold, 5-fold, 10-fold, 50-fold, 100-fold, etc.) relative to the SCN1A expression and/or activity of a subject who has not been administered one or more compositions described by the disclosure.

As used herein, the terms "treatment", "treating", and "therapy" refer to therapeutic treatment and prophylactic or preventative manipulations. The terms further include ameliorating existing symptoms, preventing additional symptoms, ameliorating or preventing the underlying causes of symptoms, preventing or reversing causes of symptoms, for example, symptoms associated with a haploinsufficient gene, e.g., a haploinsufficent SCN1A gene. Thus, the terms denote that a beneficial result has been conferred on a subject with a disorder (e.g., a disease or condition associated with a haploinsufficient gene, e.g., Dravet syndrome), or with the potential to develop such a disorder. Furthermore, the term "treatment" also includes the application or administration of an agent (e.g., therapeutic agent or a therapeutic composition, e.g., an isolated nucleic acid or rAAV that targets or binds to a target gene or a regulatory region of a target gene) to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease.

Therapeutic agents or therapeutic compositions may include a compound in a pharmaceutically acceptable form that prevents and/or reduces the symptoms of a particular disease (e.g., a disease or condition associated with a haploinsufficient gene, e.g., Dravet syndrome). For example a therapeutic composition may be a pharmaceutical composition that prevents and/or reduces the symptoms of a disease or condition associated with a haploinsufficient gene, e.g., Dravet syndrome. It is contemplated that the therapeutic composition of the present invention will be provided in any suitable form. The form of the therapeutic composition will depend on a number of factors, including the mode of administration as described herein. The therapeutic composition may contain diluents, adjuvants and excipients, among other ingredients as described herein.

Modes of Administration

The isolated nucleic acids, rAAVs and compositions of the disclosure may be delivered to a subject in compositions according to any appropriate methods known in the art. For example, an rAAV, preferably suspended in a physiologically compatible carrier (e.g., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177, 403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), thalamus, spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat.

Genet. 3:219-223, 1993; and Alisky and Davidson, Hum. Gene Ther. 11:2315-2329, 2000). In some embodiments, an rAAV as described in the disclosure are administered by intravenous injection. In some embodiments, rAAVs are administered by intracerebral injection. In some embodiments, rAAVs are administered by intrathecal injection. In some embodiments, rAAVs are administered by intrastriatal injection. In some embodiments, rAAVs are delivered by intracranial injection. In some embodiments, rAAVs are delivered by cisterna magna injection. In some embodiments, the rAAV are delivered by cerebral lateral ventricle injection.

Aspects of the instant disclosure relate to compositions comprising a recombinant AAV comprising a capsid protein and a nucleic acid encoding a transgene, wherein the transgene comprises a nucleic acid sequence encoding one or more proteins. In some embodiments, the nucleic acid further comprises AAV ITRs. In some embodiments, a composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, parachlorophenol, and poloxamers (non-ionic surfactants) such as Pluronic® F-68. Suitable chemical stabilizers include gelatin and albumin.

The rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is administered to the subject during a pre-symptomatic stage of the lysosomal storage disease. In some embodiments, the pre-symptomatic stage of the lysosomal storage disease occurs between birth (e.g., perinatal) and 4-weeks of age.

In some embodiments, rAAV compositions are formulated to reduce aggregation of AAV particles in the composition, particularly where high rAAV concentrations are present (e.g., ~$10^3$ GC/mL or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host.

Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

EXAMPLES

Figure 1A:
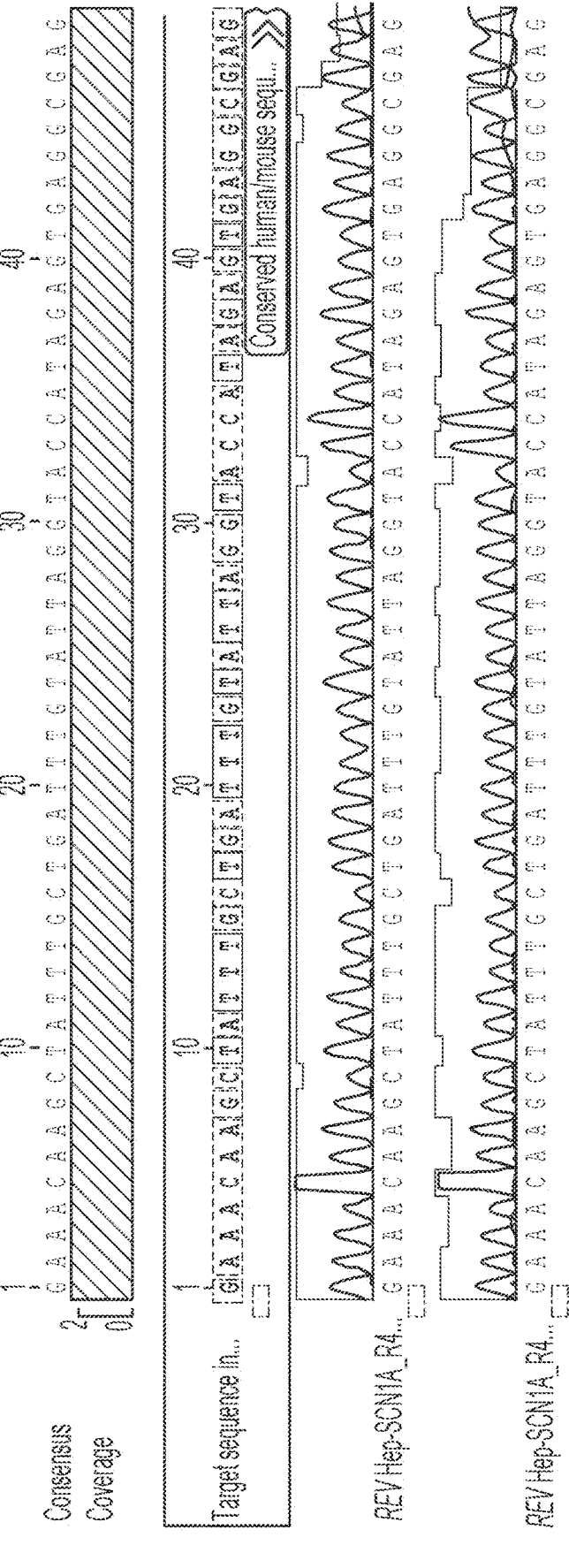
Figure 1B:
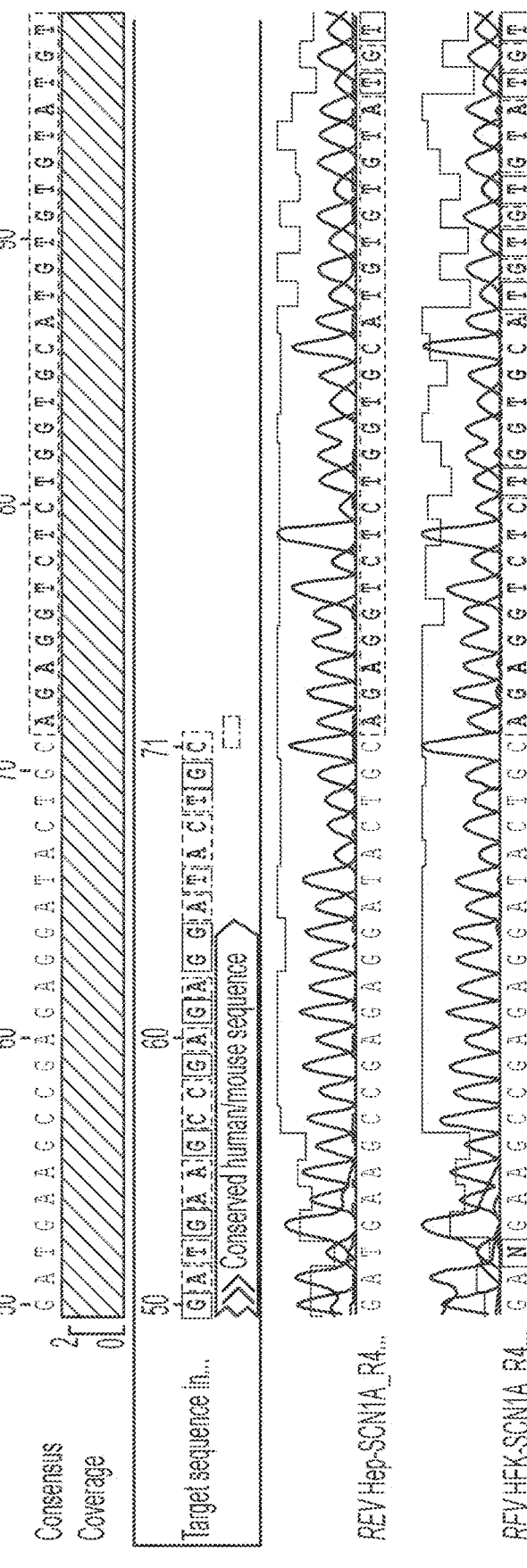

Example 1. Design of Zinc Finger Proteins to Upregulate SCN1A Gene Expression Homologous regions between the human (HEK293T cells) and mouse (HEPG2 cells) SCN1A promoter sequences were identified by alignment of sequences surrounding the two prominent transcription start sites identified in the RIKEN CAGE-seq data set for each species (FIGS. 1A-1C). A highly conserved sequence between human (HEK) and mouse (HEPG2) exists in the proximal promoter region of SCN1A (FIG. 2). Three ZFPs consisting of six fingers were designed to bind overlapping 15-22 nucleotide regions of homology in the proximal promoter region of SCN1A through the assembly of one and two-finger modules with pre-defined DNA-binding specificity (FIG. 3). Three ZFPs (ZFP1-ZFP3) consisting of six fingers each were designed to bind the overlapping highly conserved sequences identified in FIG. 3. Each finger is designed to bind a three base region (triplet) in the highly conserved region of the proximal promoter of SCN1A.

ZFP-1 recognizes individual three base regions (DNA triplets denoted in red separated by "•") within the proximal promoter region of the SCN1A gene (SEQ ID NO: 2), as shown in FIG. 4A. Each recognition helix (seven amino acids) of fingers 1 through 6 for ZFP-1 bind a three nucleotide sequences, as shown in FIG. 4B. The amino acid sequences of the six fingers of ZFP-1 (SEQ ID NOs: 17-22) are shown in FIG. 4C; the linkers between the fingers are highlighted to designate canonical (TGEKP) and non-canonical (TGSQKP) linker sequences. Nucleotide sequences of the six fingers of ZFP-1 (SEQ ID NOs: 11-16) are shown in FIG. 4D.

TABLE 1

| Recognition helices of ZFP-1 that targets SCN1A | | |
|---|---|---|
| | Amino Acid Sequence | Nucleotide Sequence |
| ZFP-1 Recognition Helix 1 | QRGNLVR (SEQ ID NO: 17) | CAGCGGGGAAACCTGGTGAGG (SEQ ID NO: 11) |
| ZFP-1 Recognition Helix 2 | LSFNLTR (SEQ ID NO: 18) | CTGAGCTTCAATCTAACCAGA (SEQ ID NO: 12) |
| ZFP-1 Recognition Helix 3 | RSDNLTR (SEQ ID NO: 19) | CGGAGTGACAACTTAACGCGG (SEQ ID NO: 13) |
| ZFP-1 Recognition Helix 4 | DRSHLAR (SEQ ID NO: 20) | GACCGGTCTCACCTTGCCCGA (SEQ ID NO: 14) |
| ZFP-1 Recognition Helix 5 | QKAHLTA (SEQ ID NO: 21) | CAGAAGGCCCATTTGACTGCC (SEQ ID NO: 15) |
| ZFP-1 Recognition Helix 6 | RSDNLTR (SEQ ID NO: 22) | CGGTCGGACAACCTCACACGC (SEQ ID NO: 16) |

ZFP-2 recognizes individual three base regions (DNA triplets denoted in red separated by "•") within the proximal promoter region of the SCN1A gene (SEQ ID NO: 3), as shown in FIG. 5A. Each recognition helix (seven amino acids) of fingers 1 through 6 for ZFP-2 bind a three nucleotide sequences, as shown in FIG. 5B. The amino acid sequences of the six fingers of ZFP-2 (SEQ ID NOs: 29-34) are shown in FIG. 5C; the linkers between the fingers are highlighted to designate canonical (TGEKP) and non-canonical (TGSQKP) linker sequences. Nucleotide sequences of the six fingers of ZFP-1 (SEQ ID NOs: 23-28) are shown in FIG. 5D.

TABLE 2

| Recognition helices of ZFP-2 that targets SCN1A | | |
| --- | --- | --- |
| | Amino Acid Sequence | Nucleotide Sequence |
| ZFP-2 Recognition Helix 1 | RSSNLTR (SEQ ID NO: 29) | CGAAGTTCCAACCTGACACGG (SEQ ID NO: 23) |
| ZFP-2 Recognition Helix 2 | DKRTLIR (SEQ ID NO: 30) | GACAAGCGGACCTTAATCCGC (SEQ ID NO: 24) |
| ZFP-2 Recognition Helix 3 | QRGNLVR (SEQ ID NO: 31) | CAGCGGGGAAATCTAGTGCGA (SEQ ID NO: 25) |
| ZFP-2 Recognition Helix 4 | LSFNLTR (SEQ ID NO: 32) | CTGAGCTTCAACTTGACTCGT (SEQ ID NO: 26) |
| ZFP-2 Recognition Helix 5 | RSDNLTR (SEQ ID NO: 33) | CGGAGTGACAATCTTACGAGA (SEQ ID NO: 27) |
| ZFP-2 Recognition Helix 6 | DRSHLAR (SEQ ID NO: 34) | GACCGGAGCCACTTAGCCAGG (SEQ ID NO: 28) |

ZFP-3 recognizes individual three base regions (DNA triplets denoted in red separated by "•") within the proximal promoter region of the SCN1A gene (SEQ ID NO: 4), as shown in FIG. 6A. Each recognition helix (seven amino acids) of fingers 1 through 6 for ZFP-3 bind a three nucleotide sequences, as shown in FIG. 6B. The amino acid sequences of the six fingers of ZFP-3 (SEQ ID NOs: 41-46) are shown in FIG. 6C; the linkers between the fingers are highlighted to designate canonical (TGEKP) and non-canonical (TGSQKP) linker sequences. Nucleotide sequences of the six fingers of ZFP-1 (SEQ ID NOs: 35-40) are shown in FIG. 6D.

TABLE 3

| Recognition helices of ZFP-3 that targets SCN1A | | |
| --- | --- | --- |
| | Amino Acid Sequence | Nucleotide Sequence |
| ZFP-3 Recognition Helix 1 | DRSALAR (SEQ ID NO: 41) | GACCGGAGCGCGCTGGCACGG (SEQ ID NO: 35) |
| ZFP-3 Recognition Helix 2 | RSDNLTR (SEQ ID NO: 42) | CGAAGTGACAACTTAACGCGC (SEQ ID NO: 36) |
| ZFP-3 Recognition Helix 3 | QSGDLTR (SEQ ID NO: 43) | CAGTCAGGGGACCTCACTCGT (SEQ ID NO: 37) |
| ZFP-3 Recognition Helix 4 | VRQTLKQ (SEQ ID NO: 44) | GTACGACAGACGCTTAAACAA (SEQ ID NO: 38) |
| ZFP-3 Recognition Helix 5 | AAGNLTR (SEQ ID NO: 45) | GCCGCTGGTAACTTGACACGA (SEQ ID NO: 39) |
| ZFP-3 Recognition Helix 6 | RSDNLTR (SEQ ID NO: 46) | AGATCTGATAATCTAACGCGT (SEQ ID NO: 40) |

Additional ZFPs designed to target sequences conserved in the proximal promoter region of the SCN1A gene will comprise five or six finger domains each and will bind to regions of 15-22 nucleotides that are highly conserved between human and mouse SCN1A.

TABLE 4

| | Zinc finger proteins that target SCN1A | |
| --- | --- | --- |
| | Amino Acid Sequence | Nucleotide Sequence |
| ZFP-1 | RPFQCRICMRNFSQRGNLV RHIRTHTGEKPFACDICGKK FALSFNLTRHTKIHTGSQKP FQCRICMRNFSRSDNLTRHI RTHTGEKPFACDICGKKFA DRSHLARHTKIHTGSQKPF QCRICMRNFSQKAHLTAHI RTHTGEKPFACDICGRKFA RSDNLTRHTKIHLRQKD (SEQ ID NO: 57) | CGACCATTCCAGTGTCGAATCTGCATGCGCAA CTTCAGCCAGCGGGGAAACCTGGTGAGGCAT ATCCGCACCCACACGGGAGAGAAGCCTTTTGC CTGCGATATTTGTGGAAAGAAGTTTGCTCTGA GCTTCAATCTAACCAGACACACCAAGATTCAT ACTGGGTCCCAGAAACCGTTCCAGTGTAGGAT ATGCATGAGGAATTTCTCTCGGAGTGACAACT TAACGCGGCATATAAGGACGCACACAGGTGA AAAACCATTTGCATGCGACATCTGTGGCAAAA AGTTTGCGGACCGGTCTCACCTTGCCCGACAC ACAAAAATCCATACCGGCAGTCAAAAGCCCTT TCAATGTCGCATTTGCATGCGAAACTTCTCAC AGAAGGCCCATTTGACTGCCCATATTCGTACT CATACTGGCGAGAAACCTTTCGCTTGCGATAT ATGTGGTCGTAAGTTTGCACGGTCGGACAACC TCACACGCCACACTAAGATACACCTGCGGCAG AAGGAC (SEQ ID NO: 58) |
| ZFP-2 | RPFQCRICMRNFSRSSNLTR HIRTHTGEKPFACDICGKKF ADKRTLIRHTKIHTGSQKPF QCRICMRNFSQRGNLVRHI RTHTGEKPFACDICGKKFA LSFNLTRHTKIHTGSQKPFQ CRICMRNFSRSDNLTRHIRT HTGEKPFACDICGRKFADR SHLARHTKIHLRQKD (SEQ ID NO: 59) | CGACCATTCCAGTGTCGAATCTGCATGCGCAA CTTCAGCCGAAGTTCCAACCTGACACGGCATA TCCGCACCCACACGGGAGAGAAGCCTTTTGCC TGCGATATTTGTGGAAAGAAGTTTGCTGACAA GCGGACCTTAATCCGCCACACCAAGATTCATA CTGGGTCCCAGAAACCGTTCCAGTGTAGGATA TGCATGAGGAATTTCTCTCAGCGGGGAAATCT AGTGCGACATATAAGGACGCACACAGGTGAA AAACCATTTGCATGCGACATCTGTGGCAAAAA GTTTGCGCTGAGCTTCAACTTGACTCGTCACA CAAAAATCCATACCGGCAGTCAAAAGCCCTTT CAATGTCGCATTTGCATGCGAAACTTCTCACG GAGTGACAATCTTACGAGACATATTCGTACTC ATACTGGCGAGAAACCTTTCGCTTGCGATATA TGTGGTCGTAAGTTTGCAGACCGGAGCCACTT AGCCAGGCACACTAAGATACACCTGCGGCAG AAGGAC (SEQ ID NO: 60) |
| ZFP-3 | RPFQCRICMRNFSDRSALAR HIRTHTGEKPFACDICGKKF ARSDNLTRHTKIHTGSQKPF QCRICMRNFSQSGDLTRHIR THTGEKPFACDICGKKFAV RQTLKQHTKIHTGSQKPFQ CRICMRNFSAAGNLTRHIRT HTGEKPFACDICGRKFARS DNLTRHTKIHLRQKD (SEQ ID NO: 61) | CGACCATTCCAGTGTCGAATCTGCATGCGCAA CTTCAGCGACCGGAGCGCGCTGGCACGGCAT ATCCGCACCCACACGGGAGAGAAGCCTTTTGC CTGCGATATTTGTGGAAAGAAGTTTGCTCGAA GTGACAACTTAACGCGCCACACCAAGATTCAT ACTGGGTCCCAGAAACCGTTCCAGTGTAGGAT ATGCATGAGGAATTTCTCTCAGTCAGGGGACC TCACTCGTCATATAAGGACGCACACAGGTGAA AAACCATTTGCATGCGACATCTGTGGCAAAAA GTTTGCGGTACGACAGACGCTTAAACAACACA CAAAAATCCATACCGGCAGTCAAAAGCCCTTT CAATGTCGCATTTGCATGCGAAACTTCTCAGC CGCTGGTAACTTGACACGACATATTCGTACTC ATACTGGCGAGAAACCTTTCGCTTGCGATATA TGTGGTCGTAAGTTTGCAAGATCTGATAATCT AACGCGTCACACTAAGATACACCTGCGGCAG AAGGAC (SEQ ID NO: 62) |

Example 2. ZFPs Increase SCN1A Gene Expression in Human Cells

To examine the ability of ZFP1-ZFP3 to upregulate transcription of SCN1A, the ZFP1-ZFP3 DNA binding domains were fused to a hybrid VP64, p53, and RTA (VPR) tripartite strong transcriptional activator domain to form a chimeric transactivator. The VPR fusion activator domain acts to recruit transcriptional regulatory complexes and increase chromatin accessibility and helps to achieve high levels of gene expression. Thus, the ZFP domain will target the VPR activator to the highly conserved sequence in the proximal promoter region to increase SCN1A gene expression.

Figure 7:
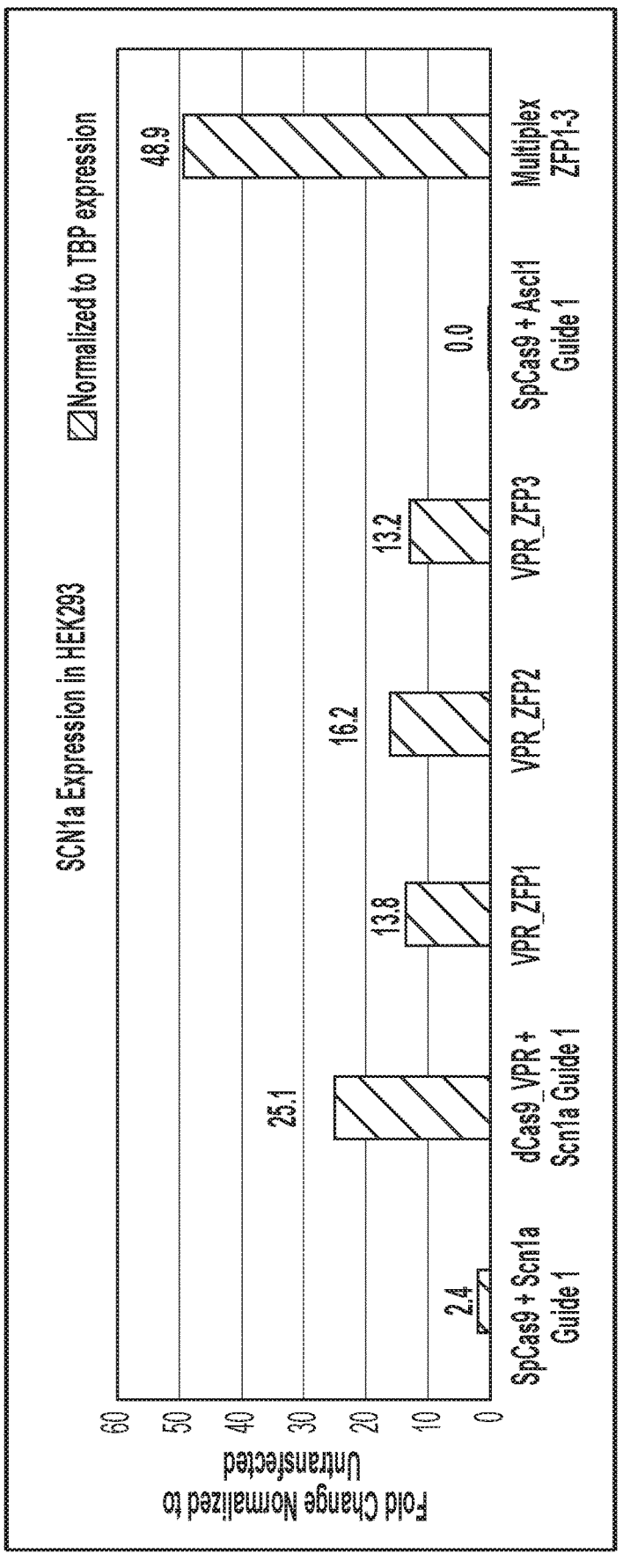
FIG. 7 shows data indicating that the SCN1A-binding ZFPs described in FIGS. 4-6 increase SCN1A gene expression in HEK293T cells, as measured by quantitative real-time polymerase chain reaction (qRT-PCR). These expression constructs were delivered to the cells via transient transfection of expression plasmids encoding the following transcriptional regulators: *Streptococcus pyogenes* Cas9+ SCN1A guide RNA (SpCas9+Scn1a); Cas9 without endonuclease activity (dCas9); VPR activation domain+SCN1A guide RNA (dCas9_VPR+Scn1a); VPR activation domain+ ZFP1 (VPR_ZFP1); VPR activation domain+ZPF2 (VPR_ZFP2); VPR activation domain+ZFP3 (VPR_ZFP3); SpCas9+ASCL1 guide RNA (SpCas9+Ascl1); three VPR_ZFPs (VPR_ZFP1+VPR_ZFP2+VPR_ZFP3).

Expression plasmids encoding VPR-ZFP1, VPR-ZFP2, and/or VPR-ZFP3 fusion proteins were transfected via transient transfection into HEK293 cells and SCN1A gene expression was measured by qRT-PCR (using TBP expression as a reference for normalization). The VPR-ZFP fusions comprise ZFP1, ZFP2, and/or ZFP3 fused to VPR. Transfection of three constructs for multiplex regulation, which contained ZFP1, ZFP2, and ZFP3 DNA binding domains each fused to VPR, resulted in 45-fold increased SCN1A gene expression relative to untransfected cells, indicating that the VPR-ZFP chimeric transactivators are able to increase SCN1A gene expression by binding in the promoter proximal region of the gene (FIG. 7).

VPR-[ZFP1-ZFP3] fusion proteins, as well as VPR-ZFP fusion proteins in which the ZFP DNA binding domain is currently being designed, are being transfected in HeLa and HEPG2 cells, both of which have low levels of SCN1A expression. The VPR-ZFP fusion proteins contain single as well as combinations of multiple ZFP DNA binding domains fused to VPR transactivator. SCN1A gene expression is measured by qRT-PCR to determine if these VPR-ZFP fusions are able to increase gene expression. The most promising VPR-ZFP fusion candidates are tested in primary mouse cortical neurons following adeno-associated virus (AAV) delivery of the fusion proteins for the ability to increase SCN1A expression.

The specificity of the ZFP domains is being further optimized using a bacterial one-hybrid selection system (see, e.g., Meng, et al., "Targeted gene inactivation in zebrafish using engineered zinc-finger nucleases," *Nat Biotechnol*, 2008) to identify ideal ZFPs from a randomized library in which residues important in DNA binding are varied. The newly-selected ZFPs will be fused to VPR transactivator domains, both individually as well as in combinations of multiple ZFPs and transfected in HEK293, HeLa, and HEPG2 cells, as well as primary mouse cortical neurons to identify the candidate ZFP domains which increase SCN1A gene expression the most following qRT-PCR analysis.

Example 3. Generate ZFP$^{SCN1A}$ Transactivator Series with Varying Potencies The most effective ZFPs in upregulating SCN1A gene expression from Example 2 is fused to a series of human transactivation domains (e.g., Rta, p65, Hsf1, etc.) with a gradient of anticipated potencies to identify an assembly that achieves 2-fold upregulation of SCN1A gene expression over a range of AAV multiplicities of infection (MOIs). Mouse primary cortical neurons from normal and SCN1A$^{+/-}$ mice are infected with AAV vectors expressing ZFP$^{SCN1A}$ fusion transactivators. Expression levels of the Na$_V$1.1 protein are assessed by Western blot using and qPCR. Primary neurons treated for 8 hours with TGF-$\alpha$ are used as a positive control because this treatment increases Na$_V$1.1 protein expression by ~6 to 8-fold (Chen et al., 2015, *Neuroinflammation* 12: 126). Changes in the expression levels of other Nav alpha subunit genes are also assessed to demonstrate the specification of ZFP$^{SCN1A}$ transactivation. Immunofluorescence is used to determine whether Na$_V$1.1 expression remains restricted to GABAergic interneurons through double immunofluorescence staining with antibodies to ZFP$^{SCN1A}$ (HA tag) and markers specific for GABAergic neurons (e.g., parvalbumin$^+$ or somatostatin$^+$) or universal neuronal markers (e.g., NeuN, TUBIII, and/or Map2). The specificity of ZFP$^{SCN1A}$ for transactivation of the SCN1A gene is also assessed by ChIP-Seq and RNA-Seq to map genome binding sites and the resulting transcriptomic prolife generated upon gene transfer.

Example 4. Histone Organization and Epigenomic Landscape of the SCN1A Promoter in GABAergic Inhibitors to Guide the Design of Promoter Activity Dependent SCN1A-ZFP Transactivators The ability of ZFPs to bind genomic targets depends upon the accessibility of the target sequence (e.g., presence of a nucleosome-free region). This requirement for DNA accessibility is exploited to design ZFP transactivators that are only functional in a subset of cell types based on the presence of DNA target sequence accessibility. Additional restriction in cell type activity is achieved through the use of tissue-specific promoters for ZFP transactivator expression. Small promoters from pufferfish (*Takifugu rubripes*) somatostatin and neuropeptide Y genes have been shown to drive highly specific transgene expression in cortical and hippocampal inhibitory interneurons in the context of both AAV vectors and lentiviruses. In some embodiments, the combination of AAV-based transcriptional restriction of SCN1A-specific ZFPs that are sensitive to DNA accessibility results in highly specific up-regulation of Na$_V$1.1 protein expression in inhibitory interneurons throughout the brain. This dual regulatory approach will minimize side effects that may result from the ectopic expression of Na$_V$1.1 protein in cells where it is not normally expressed.

The nucleosome structure and epigenetic landscape of the SCN1A promoter is analyzed in both mouse and human GABAergic inhibitory and glutamergic excitatory neurons. This information is used to design GABAergic inhibitory neuron restricted ZFP transactivators through the targeting of sequences that are only accessible around the SCN1A locus in this cell type.

GABAergic inhibitory neurons from transgenic mice expressing TdTomato under a GAD67 promoter and GFP-positive glutamateric excitatory neurons generated by crossing Emx1-IRES-Cre with ROSA26/stop/EGFP mice are isolated using fluorescence activated cell sorting (FACS). Human GABAergic and excitatory neurons are generated from induced pluripotent stem cells (iPS) cells and confirmed using both immunostaining and RT-PCR for markers specific for these cell types, as well as electophysiological activity. Accessible genomic regions around the SCN1A promoter in mouse and human neuronal populations are characterized using Assay for Transposase-Accessible Chromatin (ATAC-Seq).

ZFP$^{SCN1A}$ transactivators that recognize sequences accessible only in GABAergic neurons are being designed based on differential chromatin accessibility of genomic regions around the SCN1A promoter in inhibitory and excitatory neurons. A series of candidate ZFP-VPR transactivator fusions is being generated to target different SCN1A accessible regions wherein the binding of the transactivators is expected to potently upregulate Na$_V$1.1 expression in inhibitory regions, as well as reveal any undesired induced expression of Na$_V$1.1 expression in excitatory neurons.

Expression studies are conducted in cultured human iPS-derived neuron and mouse SCN1A$^{+/-}$ primary neurons which model Dravet syndrome to determine if ZFP$^{SCN1A}$ transactivators designed to recognize DNA sequences which are only accessible in inhibitory neurons provide the necessary specificity when expressed from AAV vectors under a pan-neuronal human synapsin-1 or inhibitory interneuron-specific promoter. Na$_V$1.1 expression levels are measured by qRT-PCR, Western blot, and double immunofluorescence with neuronal-type specific markers for inhibitory GABAergic (e.g., GABA$^+$, GAD65/67$^+$, somatostatin, and/or parvalbumin) and excitatory glutamatergic (e.g., Cux1+, FoxG1,+, GABA$_A$ receptors, GABA$^-$) neurons. The cell-type specificity of ZFP$^{SCN1A}$ transactivators are being designed to target different sequences in the mouse and human SCN1A promoter as chromatin structure and DNA sequence within syntenic regions differs between species. Controls in these experiments include neuronal cultures infected with similar AAV vectors encoding GFP, ZFPs without transactivation domains, or transactivators without ZFP DNA-binding domains.

MicroRNA (miRNA) binding sites are being incorporated within the 3' untranslated region (3' UTR) of the ZFP$^{SCN1A}$ transactivators that are restricted to cell types wherein undesired expression is occurring (e.g., glutamatergic excitatory neurons). This approach was previously utilized to restrict expression of AAV-delivered transgenes (Xie, et al., "MicroRNA-regulated, systematically delivered rAAV9: a step closer to CNS-restricted transgene expression," *Mol. Ther.* 2011). Differences in the miRNA expression profile of GABAergic inhibitory neurons and other cell types is being determined by small RNA sequencing.

Example 5. Evaluate the Potential of AAV-ZFP$^{SCN1A}$ Gene Therapy to Correct Sodium Current Deficits in Patient-Derived iPS-Generated GABAergic Interneurons A critical step towards the development of a ZFP$^{SCN1A}$ transactivator(s) for Dravet syndrome is to demonstrate that these artificial transactivators have the desired function in human neurons. For this purpose, iPS cells from Dravet patients (n=4-6) and non-Dravet patients (n=4) are being obtained. A non-Dravet genetic background is represented within these cells, obviating the need to artificially manipulate gene expression, and thus iPS cells have emerged as the state-of-the-art cell line for biomedical research. CRISPR-Cas9 genome editing technology is being utilized to create isogenic cell lines by repairing the genetic mutation in SCN1A to the wild-type sequence, or by introducing a Dravet-associated mutation into a normal allele within a control cell line. Isogenic lines thereby eliminate the natural variability that arises from comparing cell lines from different human subjects and are thus valuable for confirming and augmenting disease-specific phenotypes. An established inhibitory neuron differentiation protocol and validation pipeline is being used to differentiate the iPS cell lines into forebrain GABAergic inhibitor interneurons.

Inhibitory neurons derived from Dravet patients exhibit reduced sodium currents and impaired action potential firing as determined by whole cell patch clamp electrophysiology measurements. Similar measurements are being performed to confirm that the Dravet-derived neurons described herein recapitulate these disease-associated phenotypes. Sodium current defects occur in inhibitor, but not excitatory neurons in Dravet patients (Sun et al) and thus only inhibitory neurons are being utilized in the current disclosure. Mutation-induced sodium channel defects in Dravet patient-derived inhibitory neurons can be rescued by ectopic expression of wild-type SCN1A (ref 20). Therefore, the methods described in the current disclosure are suitable for testing the efficacy of the ZFP$^{SCN1A}$ transactivators in restoring wild-type sodium channel function and physiology in the context of Dravet syndrome.

GABAergic inhibitory neuronal cultures are being infected with AAV vectors encoding ZFP$^{SCN1A}$ transactivators under universal neuronal or inhibitory neuron-specific promoters. Changes in Na$_V$1.1 expression levels are being assessed by western blot. The restoration of functional sodium currents in inhibitory neurons is being assessed through whole cell patch clamping of untransfected compared with transfected cells. The binding of ZFP$^{SCN1A}$ transactivators across the genome in all patient-derived inhibitory neurons is being analyzed by ChIP-seq and correlated with any identified transcriptome changes detected by RNA-seq. Controls in these experiments are neuronal cultures infected with similar AAV vectors encoding GFP, ZFPs without VPR transactivator domains, and VPR transactivator domains without ZFP DNA binding domains.

Example 6. Assessing the Therapeutic Potential of AAV-ZFP$^{SCN1A}$ Intervention at Different Ages and Delivery Routes in SCN1A Mice The broad tropism of AAV is a critical property for gene therapy applications for broadly expressed genes, but can become a significant challenge when a transgene of interest is expressed in a cell-type specific manner. This has been largely solved for major tissues in the body such as liver, muscle, and heart through the use of tissue specific promoters such as the thyroxin binding protein (TBP), Creatine Kinase and Troponin T, respectively. An additional level of control can be superimposed on tissue specific promoters to achieve a higher degree of de-targeting from specific tissues by incorporation of multiple copies of binding sites for microRNAs highly abundant in those tissues, such as miR-122 in liver and miR-1 in skeletal muscle. The recently described AAV-PHP.B serotype is exceptionally efficient for CNS gene transfer after systemic delivery, where it transduces a broad range of cell types. Moreover its tropism to peripheral tissues is for the most part as broad as that for AAV9. The goal of a gene therapy approach for Dravet syndrome is to restore Na$_V$1.1 expression in GABAergic inhibitory interneurons exclusively while preventing deleterious effects from ectopic expression in other neurons and elsewhere. AAV and lentivirus vectors encoding GFP under small promoters (<2.8 kb) derived from the pufferfish (*Takifugu rubripes*) somatostatin (fSST), and neuropeptide Y (fNPY) genes have been shown to drive inhibitory neuron specific expression in the mouse brain upon intracranial injection. AAV-PHP.B vectors carrying these promoters driving GFP expression are being compared to control vectors where transgene expression is driven by the ubiquitous strong CAG promoter and the minimal relatively weak mouse MeCP2 promoter. The specificity of AAV-PHP.B-GFP vectors with fSST and fNYP promoters for GABAergic inhibitory interneurons is being studied upon delivery to the CNS by systemic administration in 6 week-old (tail vein) and post-natal day 1 (retro-orbital) mice, CSF delivery in neonates, and lastly unilateral injections targeting the dentate gyrus (DG) (Table 5). The efficiency of CNS gene transfer varies considerably with delivery route and because Scn1a$^{+/-}$ mice at different ages are being treated, a broad analysis is being conducted to establish the baseline of neuronal transduction efficacy and promoter specificity to GABAergic inhibitory interneurons throughout the CNS for each delivery route. AAV vectors driving GFP expression from the short fSST and fNYP promoters have previously been shown to be highly specific for inhibitory interneurons in the hippocampus after direct injection. The AAV-PHP.B vectors of the current disclosure are being validated in the same manner as in subsequent studies, wherein the therapeutic impact of restoring Na$_V$1.1 expression in inhibitory neurons in the hippocampal formation of Scn1a$^{+/-}$ mice, specifically located in the dentate gyrus and the inner lining of the granular cell layer is being assessed (rationale articulated below). Experiments are being conducted in 129SvJ/ C57BL/6 mice generated at UMMS by mating 129SvJ with C57BL/6 mice obtained from Jackson Laboratories (Bar Harbor, ME). Mice are being euthanized at one month post-injection and the brain and spinal cord are being collected for histological analysis of transduction efficiency and specificity using double immunofluorescence with antibodies for cell specific markers and GFP. The gene transfer efficiency and specificity for GABAergic inhibitory interneurons is being assessed throughout the brain and spinal cord by double immunofluorescence staining with antibodies to glutamic acid decarboxylase (GAD; marker for GABAergic neurons) and GFP. In addition the preferential specificity of promoters and/or AAV-PHP.B for subsets of inhibitory interneurons expressing somatostatin (SST), parvalbumin (PV), calretinin (CR), vasoactive intestinal peptide (VIP) or neuropeptide Y (NPY) using antibodies specific for those proteins and GFP is assessed. Liver, heart and skeletal muscle are collected from mice treated by systemic and ICV administration to assess GFP expression histologically and western blots are being utilized to determine the possibility of ectopic expression in peripheral tissues.

TABLE 5

| Experimental groups | | | | |
|---|---|---|---|---|
| | Number of mice per cohort Delivery route | | | |
| | Systemic | ICV | IC | |
| | Age | | | |
| Dose (vg) | 6 weeks* $2 \times 10^{12}$ | PND1 # $4 \times 10^{11}$ | PND1 # $4 \times 10^{10}$ | 8 weeks* $1 \times 10^{10}$ |
| AAV-fSST-GFP | 6 | 6-8 | 6-8 | 4 |
| AAV-fNYP-GFP | 6 | 6-8 | 6-8 | 4 |
| AAV-CAG-GFP | 6 | 6-8 | 6-8 | 4 |
| AAV-MeCP2-GFP | 6 | 6-8 | 6-8 | — |
| Vehicle (PBS) | 2 | — | — | |

*Groups are composed of equal number of mice from both sexes.
One litter injected per vector
Abbreviations:
ICV—Intracerebroventricular injection;
IC—Intracranial injection;
PND1—Post-natal day 1

Six week-old Scn1a$^{+/-}$ mice are administered bilateral injections into the dentate gyrus of AAV-PHP.B vectors encoding different ZFP$^{Scn1a}$ transactivator proteins, a construct with the ZFP$^{Scn1a}$ activation domain but without the DNA-binding domain to control for the impact of the activator alone, or the same volume of phosphate buffered saline (PBS) (n=3 males+3 females/group). The single-stranded AAV vectors used in these experiments also carry an IRES-GFP cassette downstream of the ZFP$^{Scn1a}$ cDNA to facilitate identification of transduced cells. At least two ZFP$^{Scn1a}$ transactivators are tested, which may have broader activation in a variety of neurons, as well as the two most promising GABAergic inhibitory neuron restricted ZFP$^{SCN1A}$ transactivators described above. One month post-injection, the brain is harvested and the 35 hippocampus from the one brain hemisphere is dissected to assess expression levels of ZFP$^{Scn1a}$, Na$_V$1.1, Na$_V$1.3, GAD65, GAD67 proteins by western blot using beta-actin or tubulin as loading controls. The other brain hemisphere is examined by histological studies using serial brain sections (10 μm) to analyze % transduced inhibitory interneurons in the dentate gyrus and inner leaflet of the granule cell layer by double immunofluorescence staining with antibodies to GAD and GFP, or GAD and an epitope tag included in all ZFP$^{Scn1a}$ proteins (HA or myc tag). Also, the percentage of GAD-positive neurons that express Na$_V$1.1 and Na$_V$1.3 is being determined to demonstrate restoration of the normal patterns of sodium channel expression. In addition to immunofluorescence detection of Na$_V$1.1 and Na$_V$1.3 protein expression, changes in mRNA levels in GABAergic interneurons are assessed using RNAscope probes for Na$_V$1.1, Na$_V$1.3, ZFP$^{Scn1a}$ and GAD. RNAScope is a highly sensitive in situ hybridization technique to analyze mRNAs levels in neurons in the brain. The combination of these two approaches to assess changes in Na$_V$1.1 levels resulting from ZFP$^{Scn1a}$ expression provides a comprehensive understanding of how changes in interneurons are being achieved by the gene therapy approach of the current disclosure.

The therapeutic efficacy of AAV-PHP.B-ZFP$^{Scn1a}$ gene therapy is analyzed in Scn1a$^{+/-}$ mice of both sexes initiated at post-natal day1, or 6 weeks of age via the tail vein. Controls include mice treated with an AAV vector encoding a ZFP-like protein without the ZFP DNA-binding domain, as well as age matched untreated Scn1a$^{+/-}$ mice and wild type littermates (n=15 males and 15 females per group). A subset of mice in each group (n=3 males and 3 females) is being euthanized at 12 weeks of age to assess gene transfer efficiency to GABAergic interneurons using western blot as well as immunofluorescence with antibodies to GAD (and other neuronal type specific markers, e.g., GAD65, GAD67) and the ZFP, and restoration of Na$_V$1.1 expression in those cells throughout the brain and spinal cord. Moreover, ectopic expression of ZFP is assessed, along with Na$_V$1.1 expression in peripheral tissues. The other subset of animals in each group (n=24) is being used to study impact on survival (up to 1 year of age), motor performance and behavior, which is being tested every two months from 2-12 months of age. Motor function and coordination is assessed using the accelerating rotarod and beam crossing tests, as Scn1a$^{+/-}$ mice display impaired coordination of forelimbs and hindlimbs by PND21. In addition, behavior tests are being utilized in which Scn1a$^{+/-}$ mice show impaired performance, including: open field, elevated plus maze, nest building, marble burying, and Barnes maze to test spatial learning and memory that appears to be severely compromised in Scn1a$^{+/-}$ mice. The spontaneous seizures characteristic of Dravet syndrome patients are also apparent in Scn1a$^{+/-}$ mice and the frequency increases with age and body temperature. Moreover premature sudden death of Scn1a$^{+/-}$ mice occurs immediately after tonic-clonic seizures. Therefore continuous video monitoring is being utilized for 24 hrs at 2, 6 and 12 months of age to assess seizure frequency and duration. Social interaction studies using chamber preference readouts in response to new objects, smells and mice is being considered if a significant change is detected in primary outcomes measured in the tests described above. Brain, spinal cord and peripheral organs are being collected and assessed at the experimental for humane endpoints to perform the molecular and histological analyses outlined above.

Example 7. ZFPs and dCas9 Systems Increase SCN1A Gene Expression in Human Cells

To examine the ability of ZFP1-ZFP3 to upregulate transcription of SCN1A, the ZFP1-ZFP3 DNA binding domains were fused to a hybrid VP64, p53, and RTA (VPR) tripartite strong transcriptional activator domain to form a chimeric transactivator. The VPR fusion activator domain acts to recruit transcriptional regulatory complexes and increase chromatin accessibility and helps to achieve high levels of gene expression. Thus, the ZFP domain will target the VPR activator to the highly conserved sequence in the proximal promoter region to increase SCN1A gene expression.

Further, to examine the ability of dCas9 systems that target SCN1A to upregulate transcription of SCN1A, three guide RNAs targeting SCN1A were complexed with dCas9 protein.

HEK293T cells were transiently transfected with one of the following experimental conditions—(1) a VPR-ZFP1 construct; (2) a VPR-ZFP2 construct; (3) a VPR-ZFP3 construct; (4) all three of the VPR-ZFP1, VPR-ZFP2, and VPR-ZFP3 constructs; (5) a dCas9-VPR construct and SCN1A guide RNA 1; (6) a dCas9-VPR construct and SCN1A guide RNA 2; (7) a dCas9-VPR construct and SCN1A guide RNA 3; (8) a dCas9-VPR construct and all three of SCN1A guide RNA 1, SCN1A guide RNA 2, and SCN1A guide RNA 3; and (9) a dCas9-VPR construct without any guide RNA (control). SCN1A gene expression was measured by qRT-PCR. Fold activation of SCN1A was normalized to the control experiment (dCas9-VPR construct without any guide RNA).

All tested experimental conditions produced increases in gene activation of SCN1A relative to the control experiment (FIG. 8). These data demonstrate that the zinc finger proteins described in this Example and throughout the present disclosure are capable of targeting SCN1A to influence gene expression. These data further demonstrate that the guide RNA sequences of this Example (SEQ ID NOs: 83-94) are capable of targeting dCas9 to SCN1A in order to influence gene expression.

TABLE 6

| Guide nucleic acids that target SCN1A (spacer sequence in bold) | | |
|---|---|---|
| | Nucleotide sequence (DNA) | Nucleotide sequence (RNA) |
| SCN1A guide 1 | GAGGTACCATAGAGTGAGGCG GTTTTAGAGCTAGAAATAGCAA GTTAAAATAAGGCTAGTCCGTTA TCAACTTGAAAAAGTGGCACCG AGTCGGTGC (SEQ ID NO: 83) | GAGGUACCAUAGAGUGAGGCGGUU UUAGAGCUAGAAAUAGCAAGUUAA AAUAAGGCUAGUCCGUUAUCAACUU GAAAAAGUGGCACCGAGUCGGUGC (SEQ ID NO: 84) |
| SCN1A guide 2 | ACCGAGGCGAGGATGAAGCCG AGGTTTTAGAGCTAGAAATAGC AAGTTAAAATAAGGCTAGTCCGT TATCAACTTGAAAAAGTGGCACC GAGTCGGTGC (SEQ ID NO: 87) | ACCGAGGCGAGGAUGAAGCCGAGG UUUUAGAGCUAGAAAUAGCAAGUU AAAAUAAGGCUAGUCCGUUAUCAAC UUGAAAAAGUGGCACCGAGUCGGUG C (SEQ ID NO: 88) |
| SCN1A guide 3 | ACCGAAGCCGAGAGGATACTG CAGGTTTTAGAGCTAGAAATAG CAAGTTAAAATAAGGCTAGTCC GTTATCAACTTGAAAAAGTGGCA CCGAGTCGGTGC (SEQ ID NO: 91) | ACCGAAGCCGAGAGGAUACUGCAG GUUUUAGAGCUAGAAAUAGCAAGU UAAAAUAAGGCUAGUCCGUUAUCAA CUUGAAAAAGUGGCACCGAGUCGGU GC (SEQ ID NO: 92) |

What is claimed is:

1. An isolated nucleic acid comprising a transgene configured to express at least one DNA binding domain fused to at least one transcriptional regulator domain, wherein the DNA binding domain binds to a target gene or a regulatory region of a target gene, wherein the target gene encodes a voltage-gated sodium channel, and wherein the at least one transcriptional regulator domain is encoded by the nucleic acid sequence set forth in SEQ ID NO: 47 and/or the at least one transcriptional regulator domain is encoded by the amino acid sequence set forth in SEQ ID NO: 48.

2. The isolated nucleic acid of claim 1, wherein the at least one DNA binding domain binds (i) to an untranslated region of the target gene and/or (ii) between 2-2000 bp upstream or between 2-2000 bp downstream of a regulatory region of the target gene.

3. The isolated nucleic acid of claim 1, wherein the at least one DNA binding domain encodes a zinc finger protein (ZFP), transcription-activator like effectors (TALE), a dCas protein, and/or a homeodomain.

4. The isolated nucleic acid of claim 1, wherein the at least one DNA binding domain binds to a nucleic acid sequence set forth in any one of SEQ ID NOs: 5-7.

5. The isolated nucleic acid of claim 1, wherein the at least one DNA binding domain is a zinc finger protein comprising a recognition helix encoded by a nucleic acid having a sequence set forth in any one of SEQ ID NOs: 11-16, 23-28, or 35-40.

6. The isolated nucleic acid of claim 1, wherein the at least one DNA binding domain is a zinc finger protein comprising the amino acid sequence set forth in any one of SEQ ID NOs: 17-22, 29-34, or 41-46.

7. The isolated nucleic acid of claim 1, wherein the at least one DNA binding domain is a dCas protein, and wherein the isolated nucleic acid further comprises at least one guide nucleic acid.

8. The isolated nucleic acid of claim 7, wherein the guide nucleic acid comprises a spacer sequence that targets SCN1A.

9. The isolated nucleic acid of claim 7, wherein the guide nucleic acid comprises a spacer sequence having a nucleotide sequence of any one of SEQ ID NO: 85, 86, 89, 90, 93, or 94.

10. The isolated nucleic acid of claim 7, wherein the guide nucleic acid comprises a nucleotide sequence of any one of SEQ ID NO: 83-94.

11. The isolated nucleic acid of claim 1, wherein the transgene encodes (i) 1 DNA binding domain, 2 DNA binding domains, 3 DNA binding domains, 4 DNA binding domains, 5 DNA binding domains, 6 DNA binding domains, 7 DNA binding domains, 8 DNA binding domains, 9 DNA binding domains, or 10 DNA binding domains; and/or (ii) 1 transcriptional regulator domain, 2 transcriptional regulator domains, 3 transcriptional regulator domains, 4 transcriptional regulator domains, 5 transcriptional regulator domains, 6 transcriptional regulator domains, 7 transcriptional regulator domains, 8 transcriptional regulator domains, 9 transcriptional regulator domains, or 10 transcriptional regulator domains.

12. A recombinant AAV (rAAV) comprising:
    (i) the isolated nucleic acid of claim 1, and
    (ii) at least one capsid protein.

13. A composition comprising the isolated nucleic acid of claim 1 and a pharmaceutically acceptable carrier.

14. A kit comprising:
    a container housing the isolated nucleic acid of claim 1.

15. A host cell comprising the isolated nucleic acid of claim 1.

*    *    *    *    *